United States Patent
Reed et al.

(10) Patent No.: US 8,497,134 B2
(45) Date of Patent: *Jul. 30, 2013

(54) FLUORESCENT DETECTOR SYSTEMS FOR THE DETECTION OF CHEMICAL PERTURBATIONS IN STERILE STORAGE DEVICES

(75) Inventors: Michael W. Reed, Lake Forest Park, WA (US); Steven J. Geelhood, Seattle, WA (US); Paul C. Harris, Bothell, WA (US); Lynn M. Barker, Edmonds, WA (US); Perry Hargrave, Lynnwood, WA (US); Oliver Nanassy, Edmonds, WA (US)

(73) Assignee: Blood Cell Storage, Inc., Seattle, WA (US)

( * ) Notice: Subject to any disclaimer, the term of this patent is extended or adjusted under 35 U.S.C. 154(b) by 69 days.

This patent is subject to a terminal disclaimer.

(21) Appl. No.: 11/789,431

(22) Filed: Apr. 23, 2007

(65) Prior Publication Data
US 2007/0251337 A1    Nov. 1, 2007

Related U.S. Application Data

(63) Continuation-in-part of application No. 11/207,580, filed on Aug. 19, 2005, now Pat. No. 7,608,460.

(60) Provisional application No. 60/794,193, filed on Apr. 21, 2006, provisional application No. 60/602,684, filed on Aug. 19, 2004, provisional application No. 60/674,393, filed on Apr. 22, 2005.

(51) Int. Cl.
*G01N 31/16* (2006.01)
*G01N 31/22* (2006.01)

(52) U.S. Cl.
USPC ............ 436/163; 73/866; 436/164; 436/172; 422/50; 422/82.08

(58) Field of Classification Search
None
See application file for complete search history.

(56) References Cited

U.S. PATENT DOCUMENTS

| 2,136,236 A | 11/1938 | Draper |
| 2,856,885 A | 10/1958 | Huyck et al. |
| 2,856,930 A | 10/1958 | Huyck et al. |
| 2,890,177 A | 6/1959 | Kilmer |

(Continued)

FOREIGN PATENT DOCUMENTS

| DE | 41 08 808 A1 | 9/1992 |
| EP | 0 073 558 A2 | 3/1983 |

(Continued)

OTHER PUBLICATIONS

Aizawa, M., et al., "Molecular Assembling Technology for Electrochemical and Optical Enzyme-Sensing Films," *Proceedings of the International Conference on Solid State Sensors and Actuators*, Digest of Technical Papers, Transducers '91, IEEE, San Francisco, California, Jun. 24-27, 1991, pp. 68-73.

(Continued)

*Primary Examiner* — Dirk Bass
(74) *Attorney, Agent, or Firm* — Christensen O'Connor Johnson Kindness PLLC

(57) ABSTRACT

System and method for detecting and measuring chemical perturbations in a sample. The system and method are useful for non-invasive pH monitoring of blood or blood products sealed in storage bags.

19 Claims, 44 Drawing Sheets

U.S. PATENT DOCUMENTS

| | | | |
|---|---|---|---|
| 3,068,073 | A | 12/1962 | Stanford |
| 3,754,867 | A | 8/1973 | Guenther |
| 4,116,336 | A | 9/1978 | Sorensen et al. |
| 4,200,110 | A | 4/1980 | Peterson et al. |
| 4,655,763 | A | 4/1987 | Malcolm et al. |
| 4,666,672 | A | 5/1987 | Miller et al. |
| 4,691,701 | A | 9/1987 | Williams |
| 4,728,499 | A | 3/1988 | Fehder |
| 4,743,629 | A | 5/1988 | Karakelle et al. |
| 4,746,751 | A | 5/1988 | Oviatt, Jr. et al. |
| 4,785,814 | A | 11/1988 | Kane |
| 4,861,130 | A | 8/1989 | Katsuyama et al. |
| 4,892,383 | A | 1/1990 | Klainer |
| 4,917,491 | A | 4/1990 | Ring et al. |
| 4,945,060 | A | 7/1990 | Turner et al. |
| 4,945,171 | A | 7/1990 | Haugland et al. |
| 5,094,955 | A | 3/1992 | Calandra et al. |
| 5,114,864 | A | 5/1992 | Walt |
| 5,162,229 | A | 11/1992 | Thorpe et al. |
| 5,164,796 | A | 11/1992 | Di Guiseppi et al. |
| 5,217,876 | A | 6/1993 | Turner et al. |
| 5,223,224 | A | 6/1993 | Dremel et al. |
| 5,238,809 | A | 8/1993 | Wolfbeis |
| 5,401,376 | A | 3/1995 | Foos et al. |
| 5,408,999 | A | 4/1995 | Singh et al. |
| 5,489,536 | A | 2/1996 | Ekechukwu |
| 5,495,850 | A | 3/1996 | Zuckerman |
| 5,515,864 | A | 5/1996 | Zuckerman |
| 5,518,895 | A | 5/1996 | Thorpe et al. |
| 5,595,187 | A | 1/1997 | Davis |
| 5,605,809 | A | 2/1997 | Komoriya et al. |
| 5,607,644 | A | 3/1997 | Olstein et al. |
| 5,770,705 | A | 6/1998 | Shanbrom |
| 5,795,773 | A | 8/1998 | Read et al. |
| 5,814,524 | A * | 9/1998 | Walt et al. ............ 436/518 |
| 5,856,175 | A | 1/1999 | Thorpe et al. |
| 5,858,769 | A | 1/1999 | DiGuiseppi et al. |
| 5,900,215 | A | 5/1999 | Seifert et al. |
| 6,204,067 | B1 | 3/2001 | Simon et al. |
| 6,210,910 | B1 | 4/2001 | Walt et al. |
| 6,266,459 | B1 | 7/2001 | Walt et al. |
| 6,268,910 | B1 | 7/2001 | Samsoondar et al. |
| 6,271,039 | B1 | 8/2001 | Palmer et al. |
| 6,285,807 | B1 | 9/2001 | Walt |
| 6,315,767 | B1 | 11/2001 | Dumont et al. |
| 6,377,721 | B1 | 4/2002 | Walt et al. |
| 6,391,626 | B1 | 5/2002 | Adams et al. |
| 6,544,727 | B1 | 4/2003 | Hei |
| 6,558,546 | B2 | 5/2003 | Allcock et al. |
| 6,602,716 | B1 | 8/2003 | Klimant |
| 6,636,652 | B1 | 10/2003 | Kopelman et al. |
| 6,667,159 | B1 | 12/2003 | Walt et al. |
| 6,673,532 | B2 | 1/2004 | Rao |
| 6,684,680 | B2 | 2/2004 | Pierskalla et al. |
| 6,694,157 | B1 | 2/2004 | Stone et al. |
| 6,726,671 | B2 | 4/2004 | Dumont et al. |
| 6,727,356 | B1 | 4/2004 | Reed et al. |
| 6,738,651 | B1 | 5/2004 | Jackson |
| 6,777,226 | B2 | 8/2004 | Jeffrey et al. |
| 6,790,672 | B2 | 9/2004 | Balkus, Jr. et al. |
| 6,800,765 | B2 | 10/2004 | Diwu et al. |
| 6,859,570 | B2 | 2/2005 | Walt et al. |
| 6,861,954 | B2 | 3/2005 | Levin |
| 2001/0018217 | A1 | 8/2001 | Barnard et al. |
| 2001/0024800 | A1 | 9/2001 | Garcia-Rubio et al. |
| 2002/0012923 | A1 | 1/2002 | Barenholz et al. |
| 2002/0040216 | A1 | 4/2002 | Dumont et al. |
| 2002/0076819 | A1* | 6/2002 | Bowman et al. ............ 436/56 |
| 2002/0186363 | A1 | 12/2002 | Samsoondar et al. |
| 2003/0221477 | A1 | 12/2003 | Pierskalla et al. |
| 2004/0013569 | A1 | 1/2004 | Balkus, Jr. et al. |
| 2004/0044326 | A1 | 3/2004 | Kranz et al. |
| 2004/0047769 | A1 | 3/2004 | Tanaami |
| 2004/0058453 | A1 | 3/2004 | Free et al. |
| 2004/0166024 | A1 | 8/2004 | Klimant |
| 2004/0166583 | A1 | 8/2004 | De Gaulle et al. |
| 2004/0175836 | A1 | 9/2004 | Klimant |
| 2004/0206658 | A1 | 10/2004 | Hammerstedt et al. |
| 2004/0230337 | A1 | 11/2004 | De Gaulle et al. |
| 2005/0090014 | A1 | 4/2005 | Rao et al. |
| 2005/0176066 | A1 | 8/2005 | Lukhtanov et al. |
| 2006/0204990 | A1 | 9/2006 | Lukhtanov et al. |

FOREIGN PATENT DOCUMENTS

| | | |
|---|---|---|
| EP | 0 354 719 A1 | 2/1990 |
| EP | 0 570 938 A2 | 11/1993 |
| EP | 0 601 816 A2 | 11/1993 |
| EP | 1 122 535 A2 | 8/2001 |
| FR | 2 825 637 A1 | 12/2002 |
| JP | 01227964 A | 9/1989 |
| JP | 2001194304 A | 7/2001 |
| WO | 92/19150 A1 | 11/1992 |
| WO | 98/40469 A1 | 9/1998 |
| WO | 98/58215 A1 | 12/1998 |
| WO | 02/054969 A1 | 7/2002 |
| WO | 2004/037308 A1 | 5/2004 |
| WO | 2006/023725 A2 | 3/2006 |

OTHER PUBLICATIONS

Andersson, R.M., et al., "Characterization of Probe Binding and Comparison of Its Influence on Fluorescence Lifetime of Two pH-Sensitive Benzo[c]xanthene Dyes Using Intensity-Modulated Multi-Wavelength Scanning Technique," *Analytical Biochemistry* 283:104-110, 2000.

Baker, G.A., et al., "Assessment of One- and Two-Photon Excited Luminescence for Directly Measuring $0_2$, pH, $Na^+$, $Mg^{2+}$, or $Ca^{2+}$ in Optically Dense and Biologically Relevant Samples," *Applied Spectroscopy* 56(4):455-463, 2002.

Berthois, Y., et al., "Estradiol Membrane Binding Sites on Human Breast Cancer Cell Lines. Use of a Fluorescent Estradiol Conjugate to Demonstrate Plasma Membrane Binding Systems," *Journal of Steroid Chemistry* 25(6):963-972, 1986.

Haugland, R.P., Ph.D., *Handbook of Fluorescent Probes and Research Product*, 9th ed., Molecular Probes, Jay Gregory, Ph.D. et al. (ed.), Chapter 21, "Overview of pH Indicators," pp. 827-848, (2002).

Hirshfield, K.M., et al., Steady-State and Time-Resolved Fluorescence Measurements for Studying Molecular Interactions: Interaction of a Calcium-Binding Probe With Proteins,: *Biophysical Chemistry* 62:25-38, 1996.

Jiang, D., et al., "A Novel Fiber Optic Glucose Biosensor Based on Fluorescence Quenching," *Proceedings of the SPIE—The International Society for Optical Engineering USA* 4902:205-212, 2002.

Lee, L.G., et al., "Vita Blue: A New 633-nm Excitable Fluorescent Dye for Cell Analysis," *Cytometry* 10:151-164, 1989.

Matsumoto, H., et al., "Interaction of Proteins With Weak Amphoteric Charged Membrane Surfaces: Effect of pH," *Journal of Colloid and Interface Science* 264:82-88, 2003.

Nullmeyer, K.D., et al., "Extending the Range of Intracellular pH Measurements Using Fluorescent Probe Combinations," *FASEB Journal* 6(5):A797, Mar. 22, 2002 (Abstract).

Patel, P.D., "(Bio)sensors for Measurement of Analytes Implicated in Food Safety: A Review," *Trends in Analytical Chemistry* 21(2):96-115, 2002.

Rao, J.K., et al., "Implantable Controlled Delivery System for Proteins Based on Collagen—pHEMA Hydrogels," *Biomaterials* 15(5):383-389, 1994.

Reichert, U., et al., "Visualising Protein Adsorption to Ion-Exchange Membranes by Confocal Microscopy," *Journal of Membrane Science* 199:161-166, 2002.

Sinaasappel, M., and C. Ince, "Calibration of Pd-Porphyrin Phosphorescence for Oxygen Concentration Measurements In Vivo," *The American Physiological Society* 0161:2297-2303, 1996.

Slavik, J., et al., "Measurement of Individual Intracellular pH and Membrane Potential Values in Living Cells," *Proceedings of SPIE—The International Society for Optical Engineering*, Society of Photo-Optical Instrumentation Engineers, San Jose, California, Jan. 27-28, 1999, vol. 2600, pp. 76-83.

Srivastava, A., and G. Krisnamoorthy, "Time-Resolved Fluorescence Microscopy Could Correct for Probe Binding While Estimating Intracellular pH," *Analytical Biochemistry* 249:140-146, 1997.

Turner P., et al., "Measuring the Heterogeneity of Protein Loading in PLG Microspheres Using Flow Cytometry," *Journal of Controlled Release* 96:193-205, 2004.

Ulbricht, M., and Marco M. Riedel, "Ultrafiltration Membrane Surfaces With Grafted Polymer 'Tentacles': Preparation, Characterization and Application for Covalent Protein Binding," *Biomaterials* 19:1229-1237, 1998.

Wetzel, C.H.R., et al., "Functional Antagonism of Gonadal Steroids at the 5-Hydroxytryptamine Type 3 Receptor," *Molecular Endocrinology* 12(9):1441-1451, 1998.

Whitaker, J.E., et al., "Seminaphtho-Fluoresceins and -Rhodafluors: Dual Florescence pH Indicators," *Biophysical Journal* 53:197a, 1988 (Abstract).

Whitaker, J.E. et al., "Spectral and Photophysical Studies of Benzo[c]xanthene Dyes: Dual Emission pH Sensors," *Analytical Biochemistry* 194:330-344, 1991.

Wolfbeis, O.S. et al., "LED-Compatible Fluorosensor for Measurement of Near-Neutral pH Values," *Mikrochimica Acta* 108:133-141, 1992.

Xu, Z., et al., "A Novel Fiber-Optic pH Sensor Incorporating Carboxy SNAFL-2 and Fluorescent Wavelength-Ratiometric Detection," *Journal of Biomedical Materials Research* 39(1):9-15, 1998.

\* cited by examiner

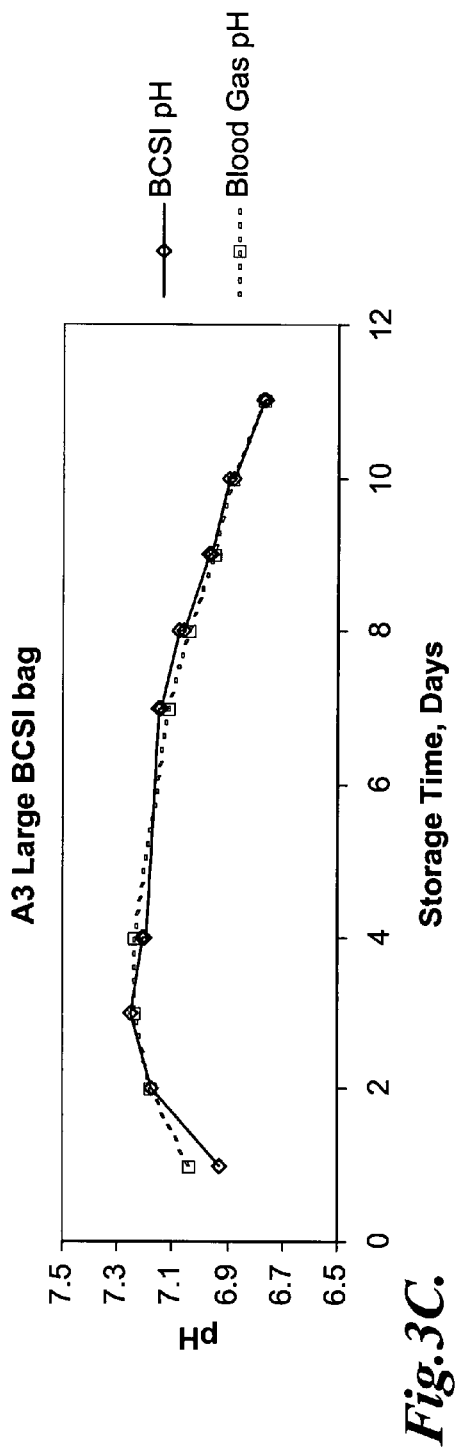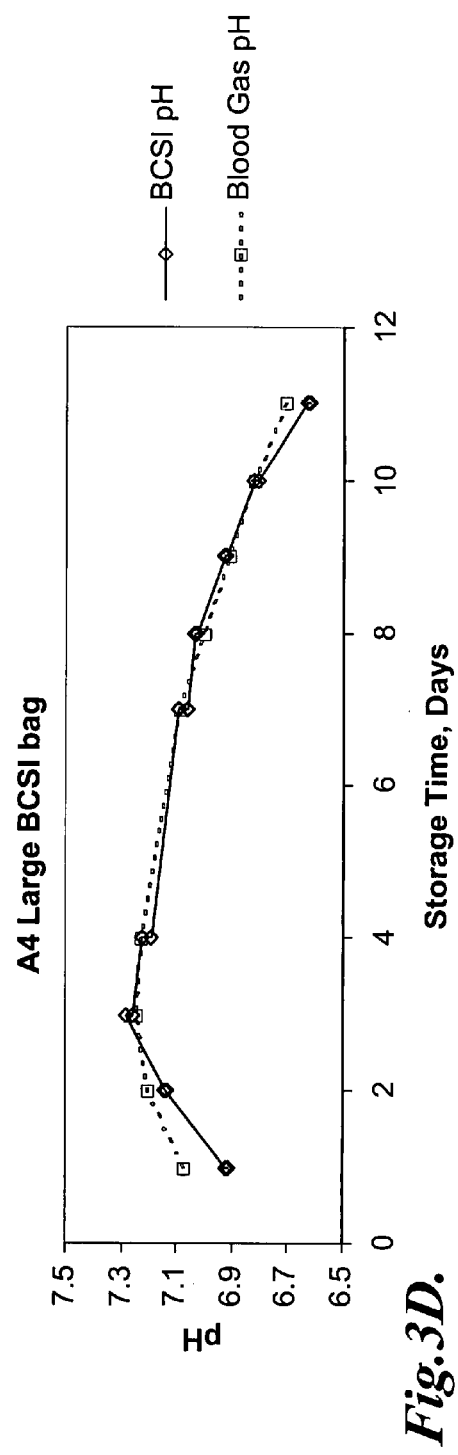
Fig.3C.
Fig.3D.

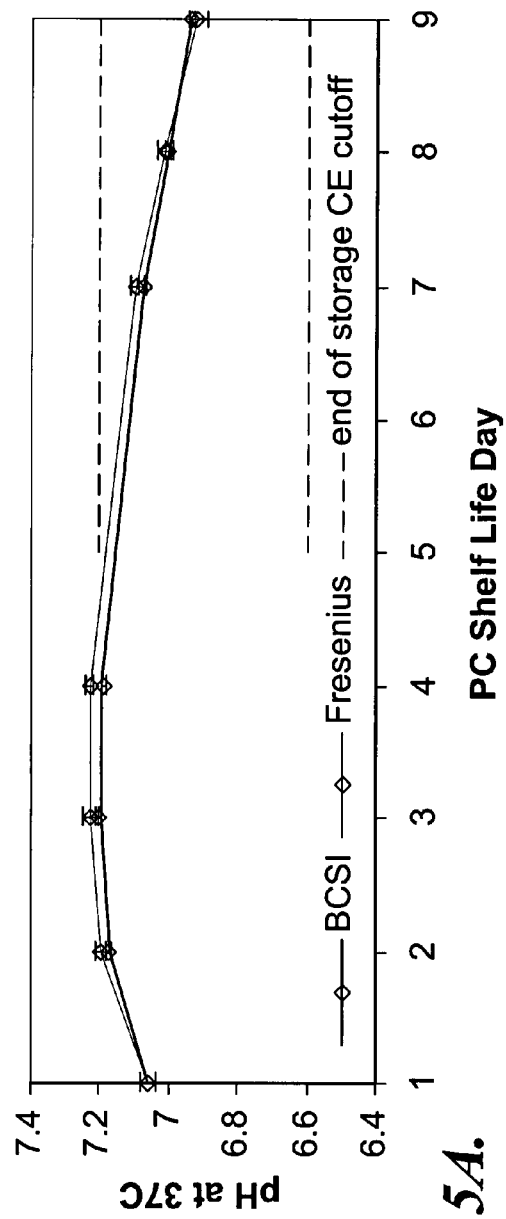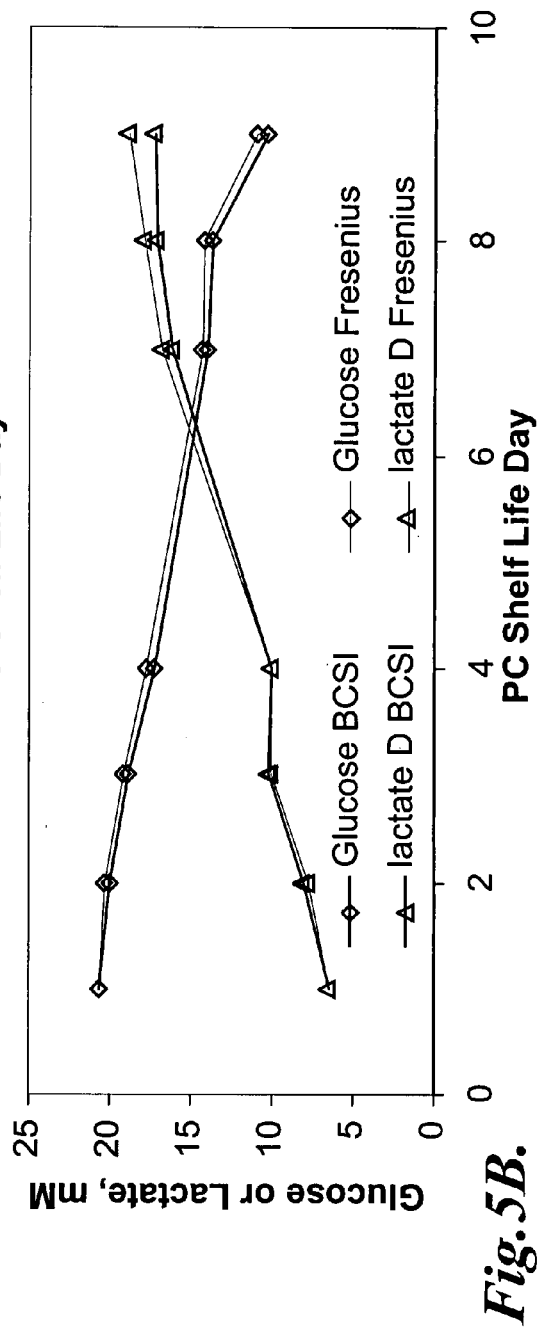
Fig. 5A.
Fig. 5B.

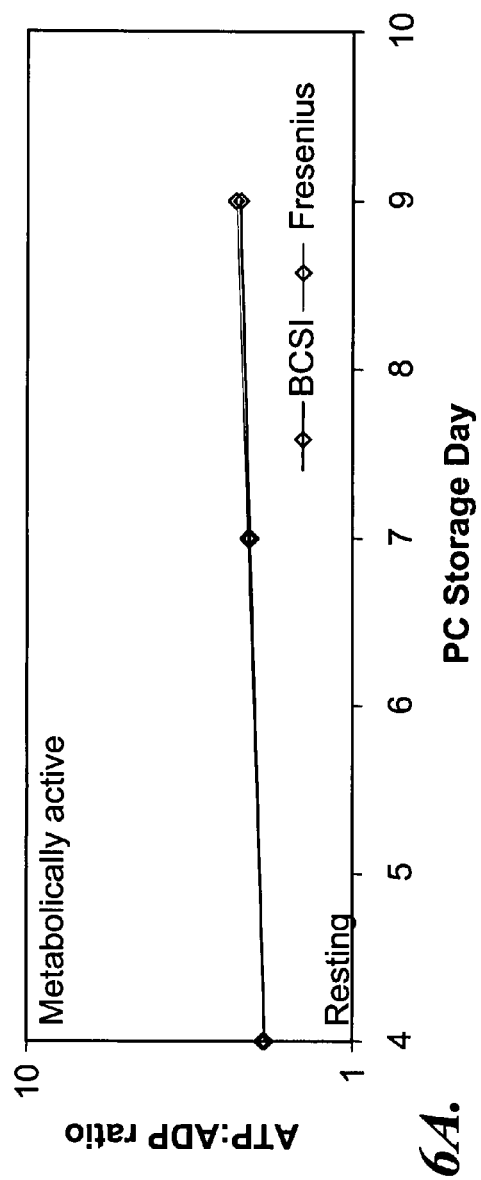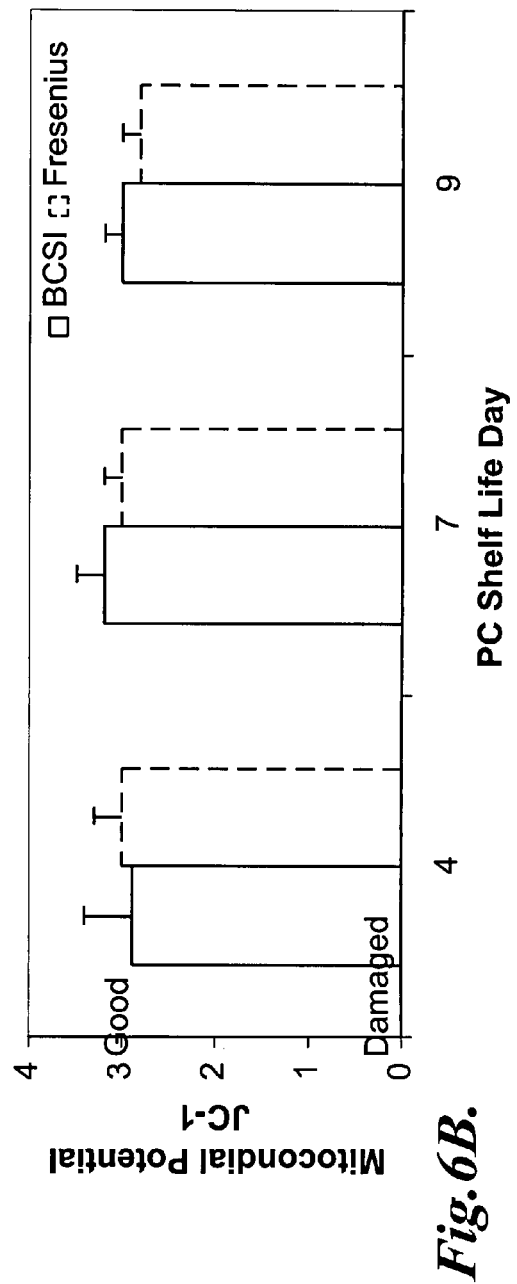
*Fig. 6A.*
*Fig. 6B.*

SNAFL-1

SNAFL-2

EBIO-1

EBIO-2

EBIO-3

FLUORESCENT DETECTOR SYSTEMS FOR THE DETECTION OF CHEMICAL PERTURBATIONS IN STERILE STORAGE DEVICES

CROSS-REFERENCE TO RELATED APPLICATIONS

This application claims the benefit of U.S. Patent Application No. 60/794,193, filed Apr. 21, 2006; and is a continuation-in-part of U.S. patent application Ser. No. 11/207,580, filed Aug. 19, 2005, which claims the benefit of U.S. Provisional Application No. 60/602,684, filed Aug. 19, 2004, and U.S. Provisional Application No. 60/674,393, filed Apr. 22, 2005, each of which is expressly incorporated herein by reference in its entirety.

BACKGROUND OF THE INVENTION

Platelets are a component of blood comprised of anucleate megakaryocyte fragments that circulate in the blood for about 10 days (van der Meer, Pietersz et al. 2001; Dijkstra-Tiekstra 2004). As they age in the circulatory system platelets are known to undergo biochemical changes that eventually leads to their clearance in the spleen and liver. When separated as a component of whole blood, platelets are routinely concentrated, resuspended in plasma and/or platelet additive solutions, leukoreduced by passage through a filtration device and stored in platelet storage bags which are kept on flatbed agitators for 5 to 7 days at a temperature of 22° C.

The measurement of pH and other parameters during preparation and storage of blood components are necessary in order to provide a safe and effective product. For example the storage of platelets at 22° C. requires testing for the presence of microbiological contamination to prevent undesired side effects such as sepsis as a result of infusion into the patient. Under the American Association of Blood Banks (A.A.B.B.) standard 5.1.5.1, blood banks or transfusion services are instructed to have methods to limit and detect bacterial contamination in all platelets. The growth of bacteria in platelet concentrates (PCs) can be monitored by utilizing reagent dipsticks for pH and glucose however the time of detection following inoculation with a low dose of organisms (e.g. 50 colony forming units/mL) varies from organism to organism, limiting this method's sensitivity and specificity given the shelf life of the product (Brecher, Hogan et al. 1994). Even in light of these limitations many centers have moved to time of issue tests utilizing the measurement of pH and glucose with a handheld device, pH paper, or in combination on a multi-reagent dipstick as surrogate markers for bacterial contamination (Burstain, Brecher et al. 1997; Yazer and Triulzi 2005).

In one method of non-invasive bacterial detection, changes in pH or the production of $CO_2$ was detected in clinical specimens by culturing the specimens with a sterile liquid growth medium in a transparent sealed container (Calandra et al., U.S. Pat. No. 5,094,955). The main disadvantage of this method is the requirement for sampling of a clinical specimen and introduction of the sample into a separate culture vessel at one point in time. The sampling is disadvantageous because the contaminating organisms may not be included in the sample volume, resulting in a false negative test. A similar method employed a sensor to detect microbial organisms growing in a liquid environment with the microbial colonies immediately available for further testing by virtue of the design of the culture vessel (Jeffrey et al., U.S. Pat. No. 5,976,827). This general method by which culture-based bacterial detection systems function is currently used for detection of microorganisms in PCs (Brecher, Means et al. 2001; McDonald, Pearce et al. 2005). A device for measuring the pH of PCs non-invasively by a fluorescence-based interrogation of the bag contents has been described in the WO 2006/023725 (PCT/US2005/029559), expressly incorporated herein by reference in its entirety.

Additional important reasons to measure pH in the quality control of PCs include its correlation with in vivo viability following transfusion into patients (Moroff, Friedman et al. 1982; Solberg, Holme et al. 1986; Holme 1998; Rinder, Snyder et al. 2003). pH Values below 6.2 in PCs have been correlated with poor in vivo recovery in transfusion studies (Murphy and Gardner 1971; Slichter and Harker 1976; Murphy 1985), while loss of recovery in vivo at pH values above 7.2 has been shown (Murphy and Gardner 1975). The platelet yield in PCs is also an important quality control parameter because it establishes the therapeutic dosage of the product and may influence the levels of metabolic activity measured within the storage bags. There have been several studies showing maintenance of pH values indicative of good platelet function up to 7 or 8 days in PCs stored in mixtures of additive solutions and plasma (Klinger 1996), provided that the platelet content was $<4\times10^{11}$ (de Wildt-Eggen, Schrijver et al. 1998). These latter studies showed that a more rapid decline in pH in a PC may correlate with higher platelet concentrations. A similar correlation of a more rapid decline in pH over the five day storage period was inferred in apheresis derived PCs obtained from machines that consistently produce product with higher platelet counts (Tudisco, Jett et al. 2005).

The storage of platelets in BTHC (n-butyryl, tri-n-hexyl citrate) PVC containers presents a number of advantages with respect to platelet health. These containers have several desirable characteristics for this medical application including low toxicity and permeability to water, $O_2$, and $CO_2$ in the desired ranges. The BTHC plasticized PVC material also has high permeability for $CO_2$, excess of which in some cases leads to difficulties storing PCs which have high platelet counts. Depending on storage conditions the pH of PCs can change rapidly due to off-gassing of dissolved $CO_2$. The Council of Europe guidelines for platelet storage conditions require the pH to be in the range of 6.4-7.4 at 37° C. (6.6-7.6 at 22° C.).

Optical sensors (optrodes) for measuring pH are well known. Certain aromatic organic compounds (like phenolphthalein) change color with pH and can be immobilized on solid supports to form "pH paper." These visual indicators are easy to use, but do not provide a quantitative reading. The color changes can be difficult to distinguish accurately, and can be masked by colored analyte. Fluorescent indicators have also been used as optical sensors. pH Sensitive fluorescent dyes can be immobilized on solid supports and generally are more sensitive in comparison to the simple calorimetric (absorbance or reflectance based) indicators. The improved sensitivity of fluorescent indicators allows the solid support to be miniaturized, and this has been used to advantage in development of fiber optic sensor devices for measuring pH, $CO_2$, and $O_2$ parameters in blood.

A specific need in the medical industry exists for accurate pH measurement of blood and blood products. The pH of blood or other bodily fluids (pleural effusions) can be associated with certain physiologic responses associated with pathology. Blood gas analyzers are common critical care instruments. Depending on storage conditions, the pH of separated blood components (plasma, platelets) can change rapidly due to off-gassing of dissolved $CO_2$ from the enriched venous blood that is collected from a donor. Platelets in particular are metabolically active, and generate lactic acid during storage at 20° C. to 22° C. European quality guidelines for platelets prepared by the "buffycoat method" require pH of stored platelets to be pH 6.8-7.4 at 37° C. (7.0-7.6 at 22° C.).

Seminaphthofluorescein (SNAFL) compounds and the related seminaphthorhodafluor (SNARF) compounds are commercially available ratiometric fluors (Molecular Probes, Inc., Eugene, Oreg.; see, for example, U.S. Pat. No. 4,945,171) and their synthesis and spectral properties have been described. These compounds have advantages including long wavelength absorbance that can be efficiently excited with LED light sources. Relevant acid/base equilibria and associated spectral properties are shown below.

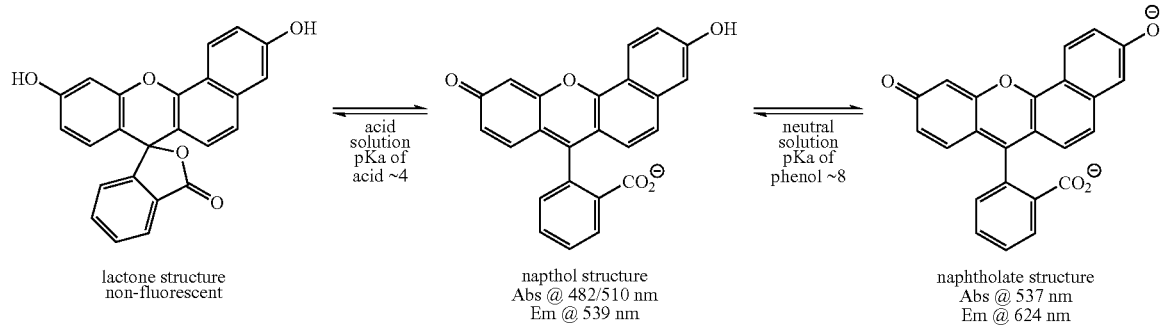

lactone structure
non-fluorescent napthol structure
Abs @ 482/510 nm
Em @ 539 nm naphtholate structure
Abs @ 537 nm
Em @ 624 nm Deprotonation of the naphthol structure of SNAFL dyes gives a naphtholate molecule with longer wavelength fluorescence emission. The pKa is the pH value where the two molecular species form in equal amounts. SNAFL compounds with reactive linker groups that allow their conjugation to other molecules of interest are also commercially available.

Various methods have been used to immobilize "ratiometric" dyes to solid supports for use in fiber optic pH detectors. Carboxynaphthofluorescein (CNF) has been conjugated to aminoethyl-cellulose and this material was glued to polyester (Mylar) films to make sensing membranes for optrodes. The pKa of this material was determined to be 7.41, slightly lower than the free CNF (pKa 7.62). The use of tetraethoxysilane to trap CNF in a sol-gel glass that was formed on glass cover slips has also been reported. The pKa of this material was determined to be 7.46. A 9-chloro substituted SNAFL analog (SNAFL-2) has been reacted with polyvinylamine and the residual amino groups crosslinked with a photocrosslinker to form a gel-like coating on acrylic fibers. The pKa of this fiber-optic sensor was determined to be 7.14, significantly lower than the published pKa of the free SNAFL compound (pKa ~7.7). This shows that molecular environment and linker structure surrounding the immobilized dye can alter the performance of a pH detector.

Despite the advances made in the detection of pH noted above, there exists a need for improved methods and devices for monitoring the chemical environment in a sealed sterile container, such as a platelet storage device, continually or at discrete time intervals, in order to better understand the types and levels of metabolic activities within the storage device, as well as their origin. The present invention seeks to fulfill this need and provides further related advantages.

SUMMARY OF THE INVENTION

The present invention provides a system and method for detecting and measuring chemical perturbations in a sample.

In one aspect, the invention provides a fluorescence method for monitoring a parameter in a sample. In one embodiment, the method includes:

(a) irradiating a fluorescent species having an emission that is dependent on a parameter with excitation light emanating from a probe physically isolated from the fluorescent species to provide a fluorescent emission, wherein the fluorescent species is in liquid communication with a sample contained in a vessel;

(b) measuring the emission to determine a first parameter reading of the sample; and (c) repeating step (a) after a pre-determined time and measuring the emission to determine a second parameter reading of the sample.

In one embodiment, step (c) is repeated to provide multiple parameter readings over time to monitor the parameter of the sample. In one embodiment, the parameter is pH. In another embodiment, the parameter is $CO_2$.

In one embodiment, the method further includes writing parameter data to the vessel containing the sample, the vessel having a means for receiving the parameter data that further allows the data to be read from the vessel at a later time.

In another aspect of the invention, a system for monitoring a parameter is provided. In one embodiment, the system includes:

(a) a light source for exciting a fluorescent species having an emission that is dependent on the parameter, wherein the fluorescent species is in liquid communication with a sample contained in a vessel;

(b) an emission detector for measuring emission from the fluorescent species and creating emission data;

(c) an excitation lightguide for transmitting excitation light from the light source to the fluorescent species, wherein the lightguide comprises a first terminus proximate to the light source and a second terminus distal to the light source;

(d) an emission lightguide for transmitting emission from the fluorescent species to the emission detector, wherein the lightguide comprises a first terminus proximate to the detector and a second terminus distal to the detector;

(e) a probe housing the distal termini of the excitation lightguide and the emission light guide;

(f) a housing for receiving the probe, wherein the housing is adapted for receiving the probe at a first end and terminating with a window at the second end, the window being transparent to the excitation and the emission light, and wherein the window physically isolates the probe from the fluorescent species;

(g) a memory device for storing emission data; and (h) a processor device for converting the emission data to profile of the parameter over time.

In one embodiment, the system further includes a means for writing parameter data to the vessel containing the sample, the vessel having a means for receiving the parameter data that further allows the data to be read from the vessel at a later time.

In another aspect, the present invention provides a fluorescence method for monitoring the pH of a sample. In one embodiment, the method includes:

(a) irradiating a fluorescent species in liquid communication with a sample contained in a vessel with excitation light emanating from a probe physically isolated from the fluorescent species, wherein the excitation light has a wavelength sufficient to effect fluorescent emission from the fluorescent species, wherein the fluorescent species exhibits a first emission intensity at a first emission wavelength and a second emission intensity at a second emission wavelength, the ratio of the first and second emission intensities being dependent on pH;

(b) measuring the first and second emission intensities to determine the pH of the sample; and (c) repeating step (a) after a pre-determined time and measuring the first and second emission intensities to determine the second pH of the sample.

In one embodiment, step (c) is repeated to provide multiple pH determinations to monitor the pH of the sample over time.

In one embodiment, the method further includes writing pH data to the vessel containing the sample. The vessel having a means for receiving the pH data that further allows the data to be read from the vessel at a later time.

In another aspect of the invention, a system for monitoring pH is provided. In one embodiment, the system includes:

(a) a light source for exciting a fluorescent species, wherein the fluorescent species has a first emission intensity at a first emission wavelength and a second emission intensity at a second emission wavelength;

(b) a first emission detector for measuring the first emission intensity;

(c) a second emission detector for measuring the second emission intensity;

(d) an excitation lightguide for transmitting excitation light from the light source to the fluorescent species, wherein the lightguide comprises a first terminus proximate to the light source and a second terminus distal to the light source;

(e) a first emission lightguide for transmitting emission from the fluorescent species to the first emission detector, wherein the lightguide comprises a first terminus proximate to the detector and a second terminus distal to the detector;

(f) a second emission lightguide for transmitting emission from the fluorescent species to the second emission detector, wherein the lightguide comprises a first terminus proximate to the detector and a second terminus distal to the detector;

(g) a probe housing the distal termini of the excitation lightguide, first emission lightguide, and second emission light guide; and (h) a housing for receiving the probe, wherein the housing is adapted for receiving the probe at a first end and terminating with a window at the second end, the window being transparent to the excitation and the emission light, and wherein the window physically isolates the probe from the fluorescent species.

In one embodiment, the system further includes a means for writing pH data to the vessel containing the sample, the vessel having a means for receiving the pH data that further allows the data to be read from the vessel at a later time.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 3A-3D are graphs comparing pH profiles from different pH measurement systems for PC samples stored in representative platelet storage bags;

FIG. 5A is a graph comparing pH profiles of platelets stored in representative and control platelet storage bags;

FIG. 5B is a graph comparing glucose and lactate concentration profiles of platelets stored in representative and control platelet storage bags;

FIG. 6A is a graph comparing ATP:ADP ratio profiles for platelets stored in representative and control platelet storage bags;

FIG. 6B is a graph comparing mitochondrial potential profiles for platelets stored in representative and control platelet storage bags;

DETAILED DESCRIPTION OF THE INVENTION

Figure 1:
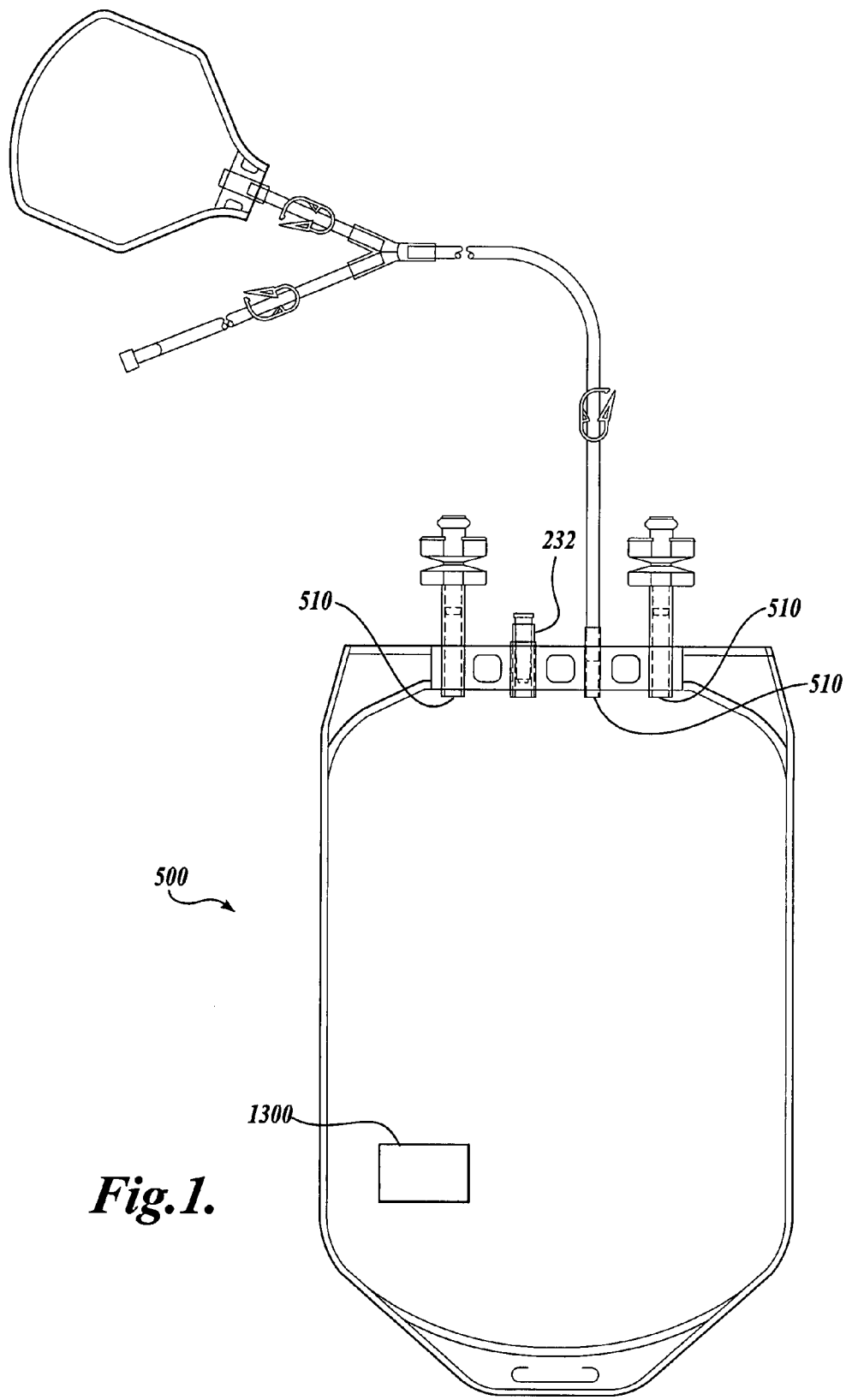
FIG. 1 illustrates a representative large platelet storage bag incorporating a pH reading insert useful in the method and system of the invention.

The present invention provides a system and method for detecting and measuring chemical perturbations in a sample. Perturbations in a sample are detected and measured by monitoring the sample for changes in a parameter measurable by the system and method. Parameters measurable by the system and method include pH and carbon dioxide ($CO_2$) level. The system and method of the invention are useful for measuring perturbations in a blood sample or a blood product sample contained in a sealed vessel.

In one aspect, the invention provides a fluorescence method for monitoring a parameter in a sample. In one embodiment, the method includes the steps of:

(a) irradiating a fluorescent species having an emission that is dependent on a parameter with excitation light emanating from a probe physically isolated from the fluorescent species to provide a fluorescent emission, wherein the fluorescent species is in liquid communication with a sample contained in a vessel;

(b) measuring the emission to determine a first parameter reading of the sample; and (c) repeating step (a) after a predetermined time and measuring the emission intensity to determine a second parameter reading of the sample.

In one embodiment, step (c) is repeated to provide multiple parameter readings over time to monitor the parameter of the sample. In one embodiment, the parameter is pH. In another embodiment, the parameter is $CO_2$.

In one embodiment, the method further includes writing parameter data to the vessel containing the sample, the vessel having a means for receiving the parameter data that further allows the data to be read from the vessel at a later time.

In another aspect of the invention, a system for monitoring a parameter is provided. In one embodiment, the system includes:

(a) a light source for exciting a fluorescent species having an emission that is dependent on the parameter, wherein the fluorescent species is in liquid communication with a sample contained in a vessel;

(b) an emission detector for measuring emission from the fluorescent species and creating emission data;

(c) an excitation lightguide for transmitting excitation light from the light source to the fluorescent species, wherein the lightguide comprises a first terminus proximate to the light source and a second terminus distal to the light source;

(d) an emission lightguide for transmitting emission from the fluorescent species to the emission detector, wherein the lightguide comprises a first terminus proximate to the detector and a second terminus distal to the detector;

(e) a probe housing the distal termini of the excitation lightguide and the emission light guide;

(f) a housing for receiving the probe, wherein the housing is adapted for receiving the probe at a first end and terminating with a window at the second end, the window being transparent to the excitation and the emission light, and wherein the window physically isolates the probe from the fluorescent species;

(g) a memory device for storing emission data; and (h) a processor device for converting the emission data to profile of the parameter over time.

In one embodiment, the system further includes a means for writing parameter data to the vessel containing the sample, the vessel having a means for receiving the parameter data that further allows the data to be read from the vessel at a later time.

In another aspect, the present invention provides a fluorescence method for monitoring the pH of a sample. In one embodiment, the method includes the steps of:

(a) irradiating a fluorescent species in liquid communication with a sample contained in a vessel with excitation light emanating from a probe physically isolated from the fluorescent species, wherein the excitation light has a wavelength sufficient to effect fluorescent emission from the fluorescent species, wherein the fluorescent species exhibits a first emission intensity at a first emission wavelength and a second emission intensity at a second emission wavelength, the ratio of the first and second emission intensities being dependent on pH;

(b) measuring the first and second emission intensities to determine the pH of the sample; and (c) repeating step (a) after a pre-determined time and measuring the first and second emission intensities to determine the second pH of the sample.

In one embodiment, step (c) is repeated to provide multiple pH determinations to monitor the pH of the sample over time.

In one embodiment, the method further includes writing pH data to the vessel containing the sample, the vessel having a means for receiving the parameter data that further allows the data to be read from the vessel at a later time.

In the above methods, the parameter profile or pH profile is made by multiple parameter or pH measurements. The multiple measurements are made over time and establish the profile. When the interval of time between measurements is sufficiently small, the profile reveals perturbations, if any, in the sample over the time period of the profile. In the methods of the invention, the interval of time between measurements is pre-determined. The pre-determined times are set to reveal perturbations in the sample.

In one embodiment, the pre-determined time is a variable time period from 1 minute to 1 day. In one embodiment, the pre-determined time is from between 1 hour to 12 hours.

In the methods, the multiple parameter or pH determinations over time provide a parameter or pH profile of a sample. The parameter or pH profile of the sample can be used to determine a quality of the sample.

Figures 20, 21:
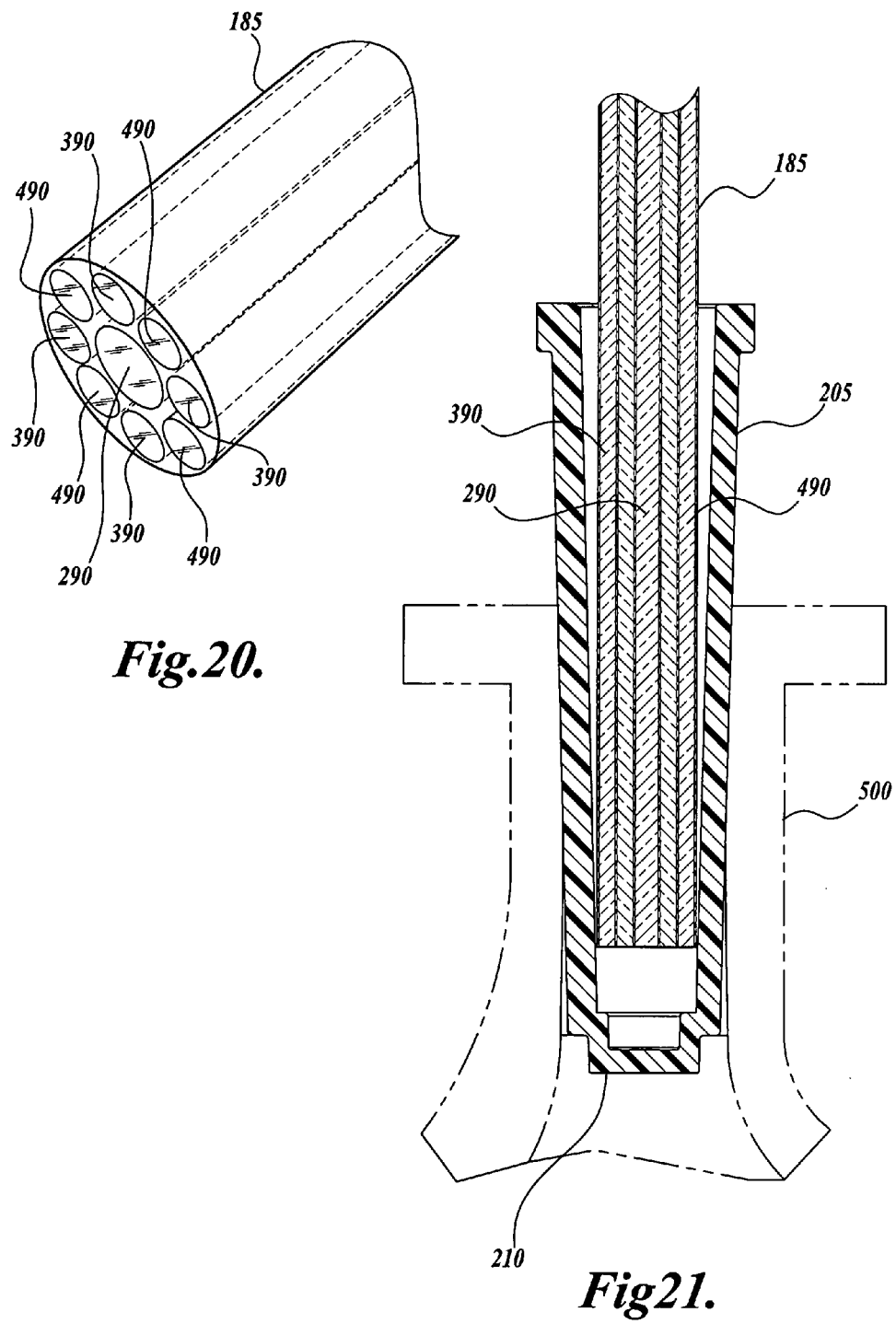
FIG. 20 is a schematic illustration of a representative housing for excitation and emission light guides useful in the system of the invention.
FIG. 21 illustrates the relationship between the excitation/emission optical fiber housing and the sealed vessel port.

In the above methods, the probe is physically isolated from the fluorescent species. As used herein, the term "physically isolated" refers to the physical isolation of the probe from the sample being interrogated. The probe providing excitation light and receiving emission light does contact the sample being interrogated. In the methods, the sample is in contact (i.e., liquid communication) with the fluorescent species (e.g., substrate-immobilized fluorescent species). The probe is isolated from and does not come not physical contact with the sample. The isolation of the probe from the sample is illustrated in FIG. 21. The probe is isolated from the fluorescent species by a window transparent to the excitation light and the fluorescent emission.

In another aspect of the invention, a system for monitoring pH is provided. In one embodiment, the system includes:

(a) a light source for exciting a fluorescent species, wherein the fluorescent species has a first emission intensity at a first emission wavelength and a second emission intensity at a second emission wavelength;

(b) a first emission detector for measuring the first emission intensity;

(c) a second emission detector for measuring the second emission intensity;

(d) an excitation lightguide for transmitting excitation light from the light source to the fluorescent species, wherein the lightguide comprises a first terminus proximate to the light source and a second terminus distal to the light source;

(e) a first emission lightguide for transmitting emission from the fluorescent species to the first emission detector, wherein the lightguide comprises a first terminus proximate to the detector and a second terminus distal to the detector;

(f) a second emission lightguide for transmitting emission from the fluorescent species to the second emission detector, wherein the lightguide comprises a first terminus proximate to the detector and a second terminus distal to the detector;

(g) a probe housing the distal termini of the excitation lightguide, first emission lightguide, and second emission light guide; and (h) a housing for receiving the probe, wherein the housing is adapted for receiving the probe at a first end and terminating with a window at the second end, the window being transparent to the excitation and the emission light, and wherein the window physically isolates the probe from the fluorescent species.

In one embodiment, the system further includes a means for writing pH data to the vessel containing the sample, the vessel having a means for receiving the pH data that further allows the data to be read from the vessel at a later time.

In one embodiment, the first and second detectors are the same. In one embodiment, the first and second detectors are different. In one embodiment, the first and second detectors are photodiodes.

In one embodiment, the first emission lightguide and the second emission lightguide are the same. In one embodiment, the first emission lightguide and the second emission lightguide are different. In one embodiment, the excitation lightguide, the first emission lightguide, and the second emission lightguide are optical fibers.

There are five basic optical chemical sensing techniques: measuring absorbance, fluorescence intensity, ratiometric fluorescence, fluorescence lifetime, and fluorescence polarization. Sample parameters, such as pH, can be measured using any of the five techniques. The systems and methods of the invention utilize fluorescence sensing and can be used to monitor sample parameters that produce changes in fluorescence intensity, ratiometric fluorescence, fluorescence lifetime, and fluorescence polarization characteristics of a fluorescent species in liquid contact with the sample to be monitored.

In one embodiment, the method is a fluorescent wavelength ratiometric method. As used herein, the term "fluorescent wavelength-ratiometric" refers to a method by which the first and second fluorescent emission intensities of a fluorescent species are measured at first and second emission wavelengths, respectively, and are ratioed to provide pH information. In this embodiment, the fluorescent species has emission intensities that vary as a function of pH.

Figure 23A:
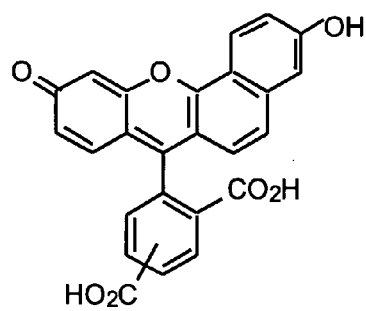
FIGS. 23A-23E illustrate the structures of representative seminaphthofluorescein compounds useful in the method and system of the invention.
Figure 23B:
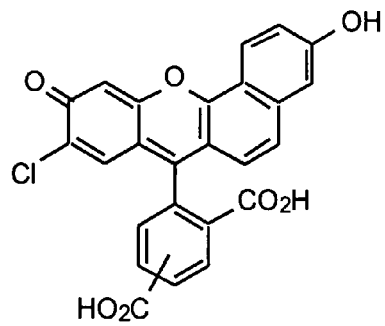
Figure 23C:
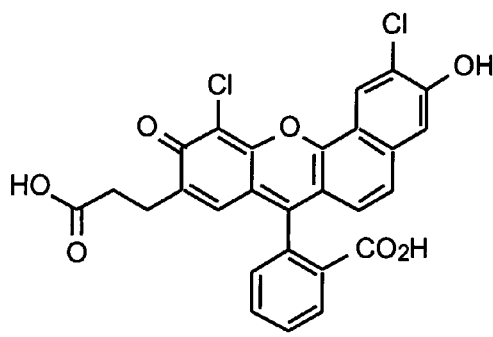
Figure 23D:
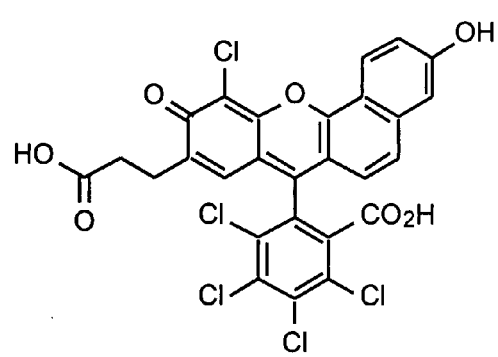
Figure 23E:
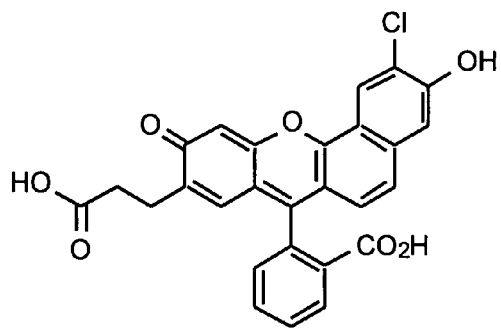

In one embodiment of the method, the fluorescent species is a ratiometric fluorescent species. In one embodiment, the fluorescent species is selected from a naphthofluorescein compound and a seminaphthorhodamine compound. In one embodiment, the naphthofluorescein compound is selected from a seminaphthofluorescein compound and a carboxynaphthofluorescein compound. In one embodiment, the seminaphthofluorescein compound is selected from 5' (and 6')-carboxy-3,10-dihydroxy-spiro[7H-benzo[c]xanthene-7, 1'(3'H)-isobenzofuran]-3'-one (also referred to herein as "SNAFL-1", see FIG. 23A) and 2-(2-chloro-3-hydroxy-9-carboxyethyl-10-oxo-10H-benzo[c]xanthen-7-yl)benzoic acid (also referred to herein as "EBIO-3", see FIG. 23E).

In one embodiment, the fluorescent species is immobilized on a substrate and comprises a conjugate of a fluorescent species and a macromolecule. In one embodiment, the macromolecule is an albumin. In one embodiment, the macromolecule is a serum albumin. In one embodiment, the macromolecule is a human serum albumin. In one embodiment, the macromolecule is a recombinant human serum albumin. In one embodiment, the fluorescent species immobilized on a substrate comprises a naphthofluorescein/serum albumin conjugate. In one embodiment, the fluorescent species immobilized on a substrate comprises a seminaphthofluorescein/human serum albumin conjugate.

As noted above, the method is suitable for measuring the pH of blood or blood products contained in a sealed vessel. In one embodiment, the fluorescent species (e.g., substrate-immobilized fluorescent species) is introduced into a sealed vessel during the vessel's manufacture and before the sample is introduced to the vessel. In one embodiment, the fluorescent species is introduced into a sealed vessel by a means that preserves the vessel's seal.

The present invention provides a method and system for monitoring a parameter of a sample. The method and system are useful in monitoring the pH or $CO_2$ of blood or blood products. The method and system are suited to monitor the pH of a sample contained in a sealed vessel.

The presence of microorganisms growing in PCs causes dynamic changes in various parameters in the mixture, such as pH, $CO_2$, $O_2$, and glucose concentrations. These parameters can be analyzed as surrogate markers for the presence of microbiological contamination. A non-invasive "in-the-bag" sensor, used to measure chemical parameters such as pH, $CO_2$ levels, $O_2$ levels, or glucose concentrations provides greater sensitivity for detecting perturbations in the bag environment caused by the growth of microorganisms due to the elimination of sampling artifacts and the ability to carry out multiple measurements over time within a closed system. The systems and methods of the invention can detect subtle changes in pH or $CO_2$ within the closed system or the bag environment, and can be monitored continuously or periodically over time without direct sampling.

In one embodiment, the invention provides a method of monitoring pH of a sealed sterile platelet storage device over time and analyzing the changes to predict the quality of the platelet rich plasma and/or platelet rich plasma additive solution formulations. The non-invasive methods described herein enable this "real-time" analysis of platelet quality. Previously, samples had to be physically withdrawn from the platelet storage bag and analyzed on a blood gas analyzer or a separate instrument. After puncturing the bag, the PC must be used within 4 hours due to risk of contamination. Preserving the unit required laborious sampling of bag contents via a long plastic tube attached to the bag (pigtail) using a sterile sealer device to remove portions thereof.

The data were presented herein was obtained using a small platelet storage bag with a 14 mL storage volume having a built-in pH reading insert. A larger storage bag for a transfusible unit is designed to hold 300 mL of pooled platelet concentrate. This larger bag could be used for platelets recovered from a single donor by apheresis or for storage of a pre-storage pooled platelet concentrate unit.

Figure 2:
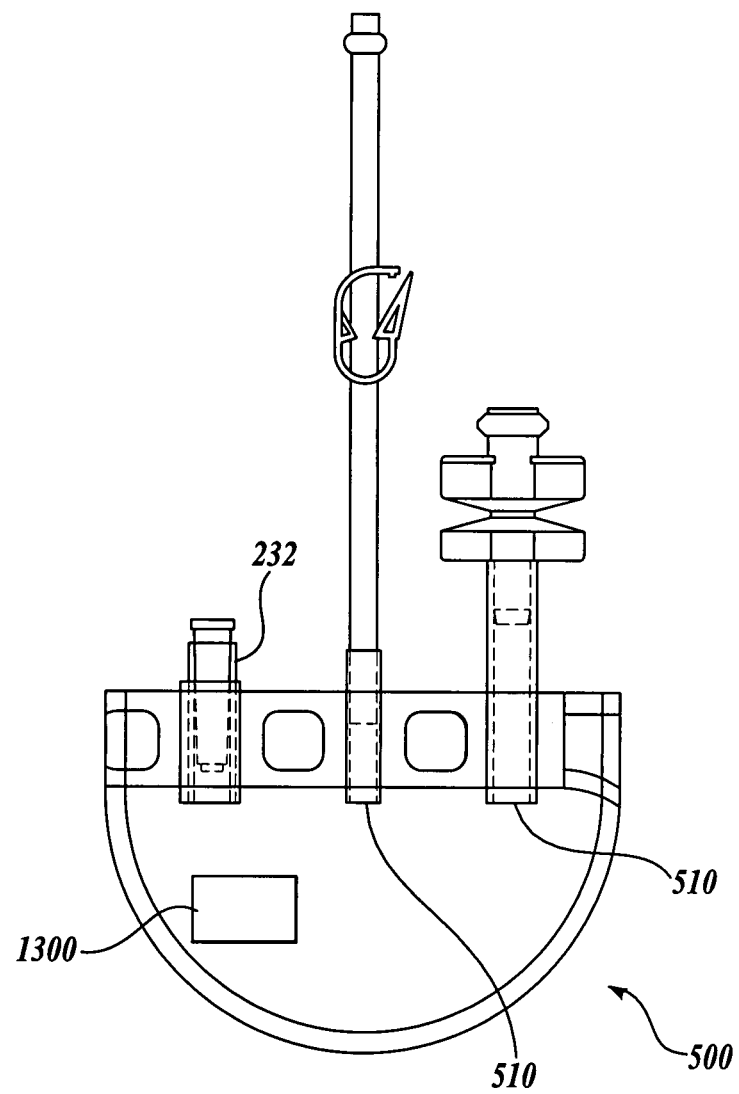
FIG. 2 illustrates a representative small platelet storage bag incorporating a pH reading insert useful in the method and system of the invention.
Figure 3A:
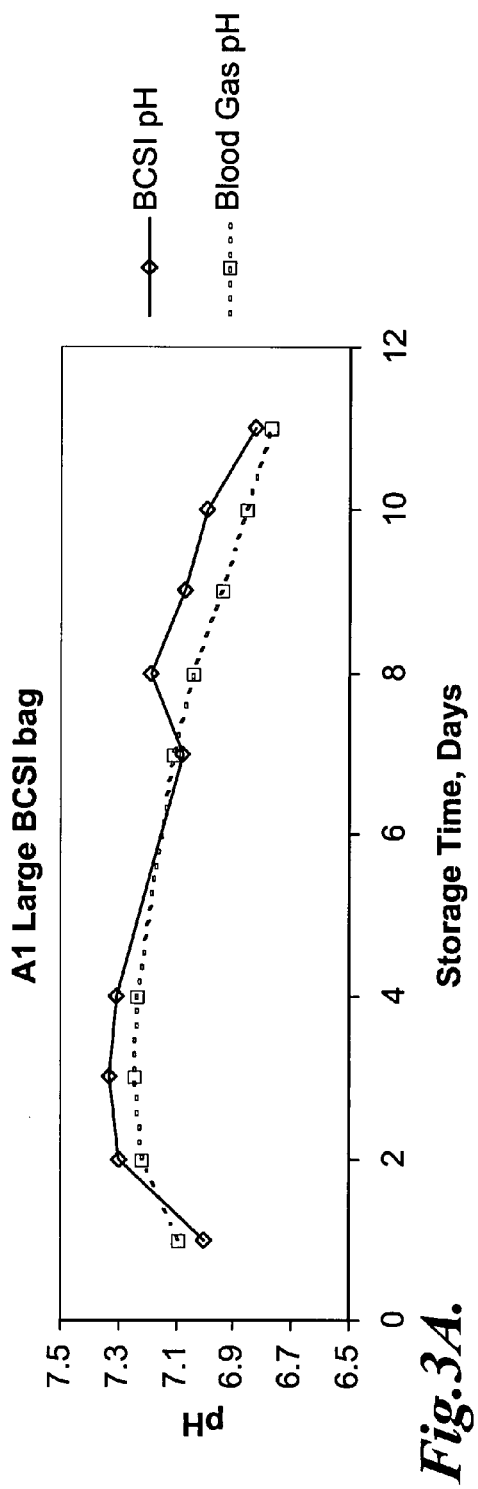
Figure 3B:
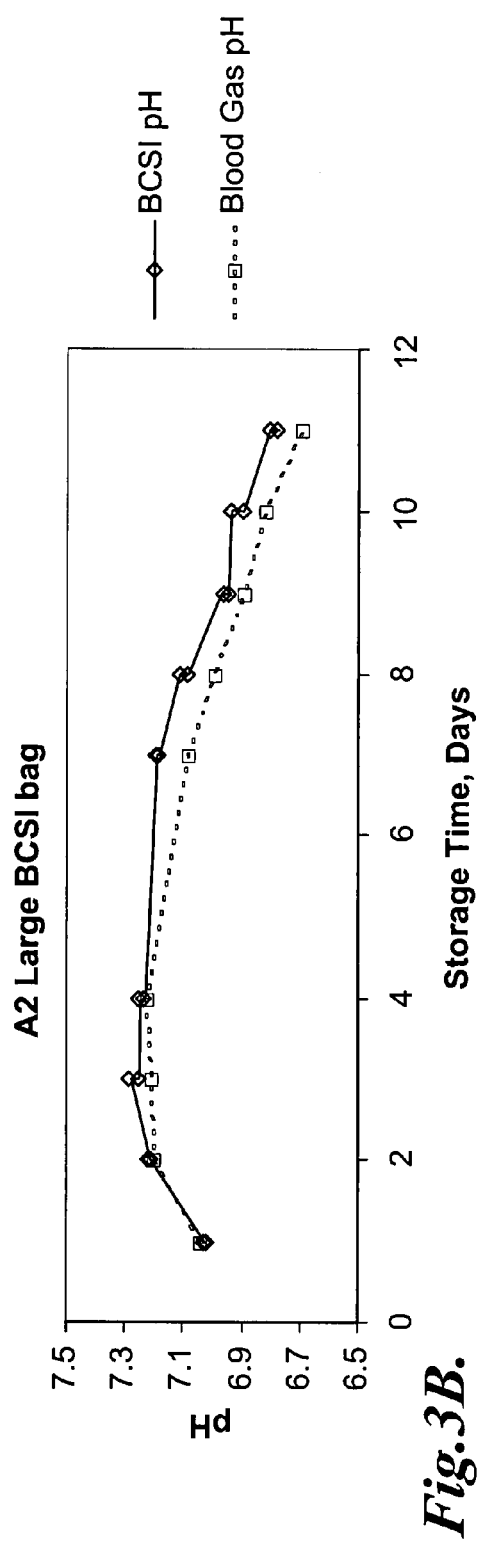

Large and small platelet storage bags with built-in inserts are shown in FIGS. 1 and 2, respectively. Referring to FIG. 1, large storage bag 500 includes a plurality of vessel ports 510 and port assembly 232. Port assembly 232 is further described in FIG. 22. Storage bag 500 also includes label 1300, into which a memory device can be integrated (not shown). By integrating a memory device into label 1300, parameter readings can be written to and stored on storage bag 500 that contains the sample.

Referring to FIG. 2, small storage bag 500 includes a plurality of vessel ports 510 and port assembly 232. Port assembly 232 is further described in FIG. 22. Storage bag 500 also includes label 1300, into which a memory device can be integrated (not shown). By integrating a memory device into label 1300, parameter readings can be written to and stored on storage bag 500 that contains the sample.

The pH reading accuracy of the non-invasive platelet bag inserts and measuring system described herein have been tested. FIGS. 3A-3D are graphs showing pH profiles of four individual PC samples. The PCs were stored in representative large sterile storage bags containing 300 mL of pooled platelet concentrates per bag. These platelets were leukoreduced prior to storage in the bags, and the four bags tested all showed good platelet health parameters over the 11 days of storage. The bags were spiked in an aseptic manner with sample site adaptors (Codan) via the twist off ports incorporated on the bags to allow samples to be withdrawn for analysis on a blood gas analyzer.

Referring to FIGS. 3A-3D, two pH profiles are shown for each sample. The pH profiles for each sample were generated from two pH measurement systems, namely, a non-invasive fluorescent pH reading and an invasive blood gas pH reading. In each figure, the pH profile generated from fluorescent pH readings is designated "BCSI pH" and shown as a solid line. The pH profile generated from blood gas pH readings is designated "Blood Gas pH" and shown as a dashed line. The data show similar pH profiles for these "normal" platelet concentrates over 11 days of storage. This demonstrates that the bags with inserts can be ethylene oxide sterilized without compromising pH reading performance. This also demonstrates that the accuracy of the two pH measurement systems (non-invasive fluorescent reading vs. invasive blood gas reading) was consistent. The mean difference from average pH determined by both methods was 0.045 (n=32, SD 0.058). This is the first demonstration of a system for measuring the metabolic activity in the contents of a platelet storage bag in a non-invasive manner over time.

To determine the suitability of the representative manufactured bags for storage of platelet concentrates, the four sterile representative bags described above were compared with similar sized control sterile platelet storage bags from Fresenius (The Netherlands). Two 300 mL pooled platelet rich plasma units were leukoreduced, combined and distributed to the paired storage bags. The bags were spiked in an aseptic manner with sample site adaptors (Codan) via the twist off ports incorporated on the bags to allow samples to be withdrawn for analysis on a blood gas analyzer. The results, shown in FIGS. 4-7, demonstrate virtually identical platelet storage parameters for the paired representative ("BCSI") and control ("Fresenius") bags.

Figure 4A:
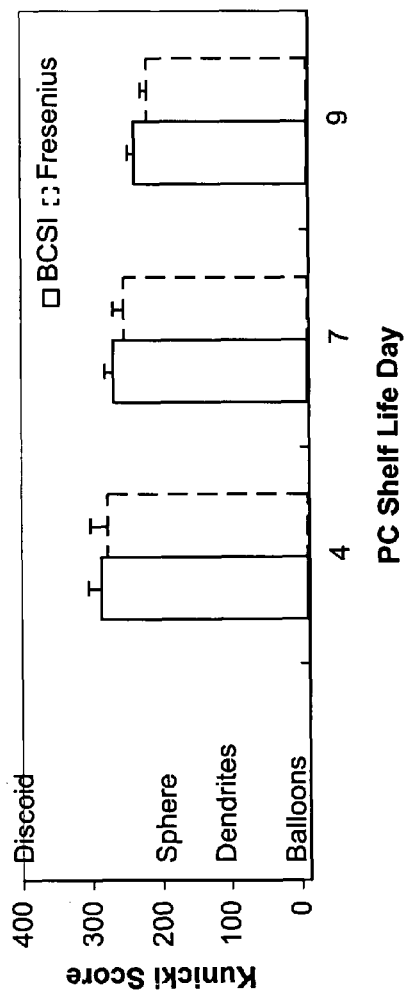
FIG. 4A is a graph comparing Kunicki Scores for platelets stored in representative and control platelet storage bags over a period of time.
Figure 4B:
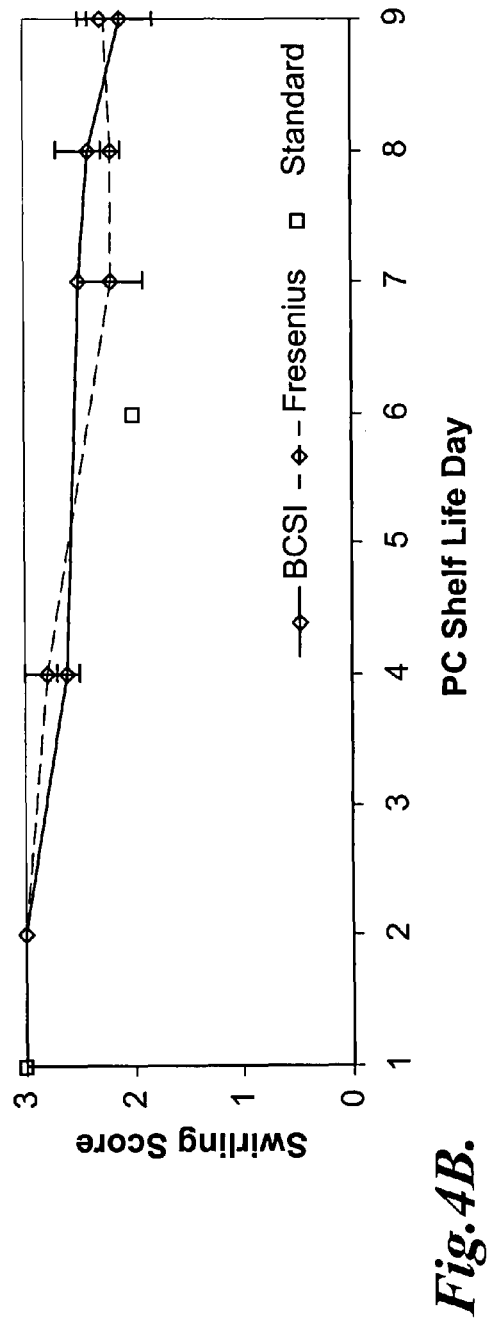
FIG. 4B is a graph comparing Swirling Scores for platelets stored in representative and control platelet storage bags over a period of time.

Referring to FIGS. 4A and 4B, platelet shape parameters for PCs stored in representative and control platelet storage bags were evaluated. FIG. 4A is a graph comparing Kunicki Scores of PCs stored in representative and control platelet storage bags for 9 days. The Kunicki Scores in FIG. 4A range in value from 0 to 400. A Kunicki Score of 0 indicates balloon-shaped, or dead platelets; 100 indicates dendrites, or an activated platelets; 200 indicates spheres, or spherical platelets; and 400 indicates discoid platelets. The results show virtually identical storage parameters for the paired representative and control bags.

FIG. 4B is a graph comparing Swirling Scores for platelets stored in representative and control platelet storage bags for 9 days. The Swirling Scores in FIG. 4B range in value from 0 to 3. A Swirling Score of 0 indicates dead platelets; a score of 2 is the standard value for platelets at 6 days of storage; and a score of 3 indicates very good platelets. The results show virtually identical storage parameters for the paired representative and control bags.

Referring to FIGS. 5A and 5B, the pH, glucose, and lactate profiles for PCs stored in representative and control platelet storage bags were determined. FIG. 5A is a graph comparing pH profiles of platelets stored in representative and control platelet storage bags for 9 days. The results show virtually identical storage parameters for the paired representative and control bags.

FIG. 5B is a graph comparing glucose and lactate concentration profiles of platelets stored in representative and control platelet storage bags for 9 days. The glucose concentrations are depicted with diamond-shaped points and range from approximately 20 mM at storage day 1 to approximately 10 mM at day 9. The lactate concentrations are depicted with triangle-shaped points and range from approximately 6 mM at storage day 1 to approximately 17 mM at day 9. The results show virtually identical storage parameters for the paired representative and control bags.

Referring to FIGS. 6A and 6B, the metabolic function of platelets stored in representative and control bags was determined. FIG. 6A is a graph comparing ATP:ADP ratio profiles for platelets stored in representative and control platelet storage bags for 9 days. The ATP:ADP ratio is measured on a scale of 1 to 10. An ATP:ADP ratio of 1 indicates a resting sample, and a ratio of 10 indicates a metabolically active sample. The results show a typical ATP:ADP response for the paired representative and control bags.

FIG. 6B is a graph comparing mitochondrial potential profiles for platelets stored in representative and control platelet storage bags for 9 days. The mitochondrial potential is measured on a scale of 0 to 4. A mitochondrial potential reading of 0 indicates damaged platelets, and a mitochondrial potential reading of 3 indicates good platelets. The results show good mitochondrial potential throughout the test period for the paired representative and control bags.

Figure 7:
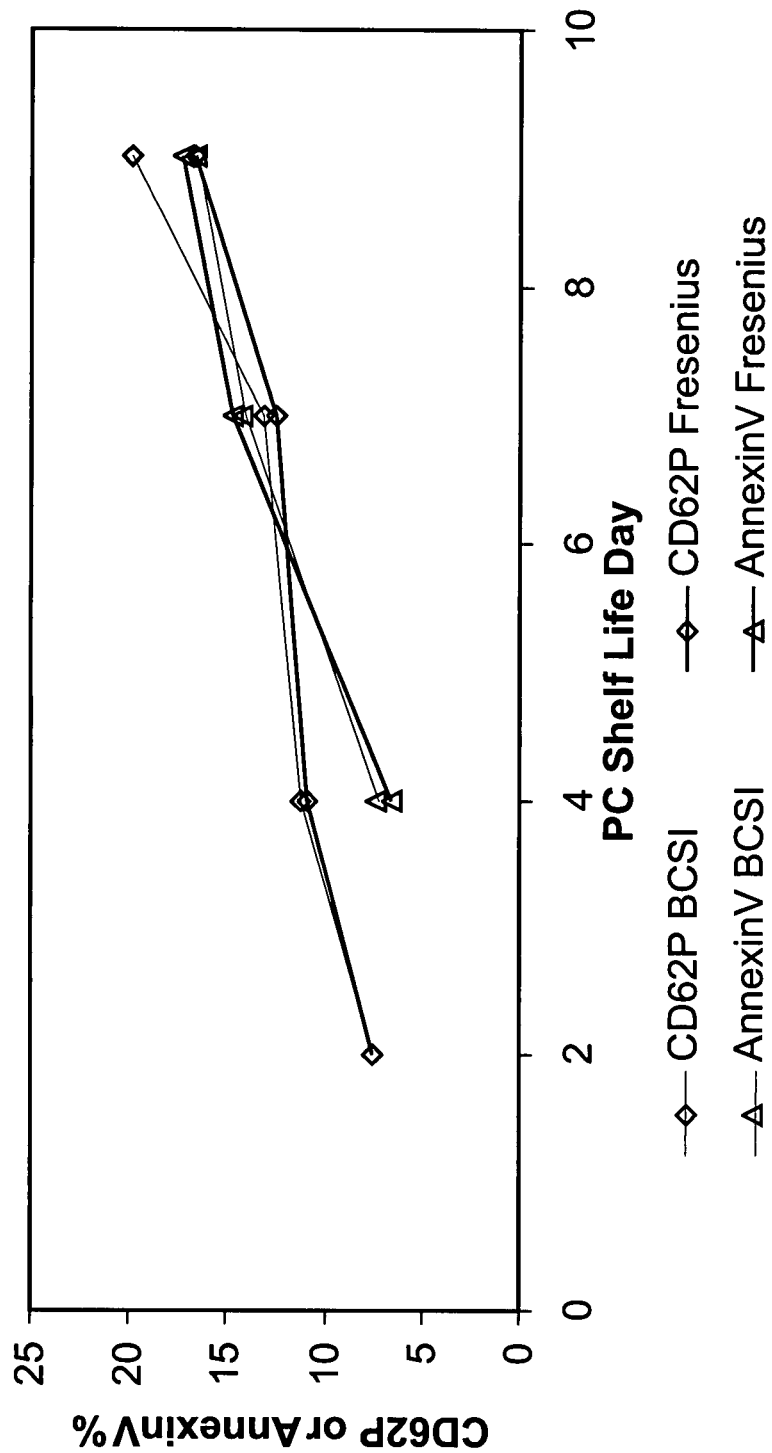
FIG. 7 is a graph comparing the level of platelet activation measured by CD62P and Annexin V percentages for platelets stored in representative and control platelet storage bags.

Referring to FIG. 7, platelet activation levels were measured for PCs in representative and control platelet storage bags for 9 days. FIG. 7 is a graph comparing the level of platelet activation measured by CD62P and Annexin V percentages. The CD62P percentages are depicted with the diamond-shaped points and range from approximately 5% at storage day 2 to approximately 17% at day 9. The Annexin V percentages are depicted with triangle-shaped points and range from approximately 5% at storage day 4 to approximately 16% at day 9. The results are consistent with moderate platelet activation in paired representative and control bags.

Figure 8:
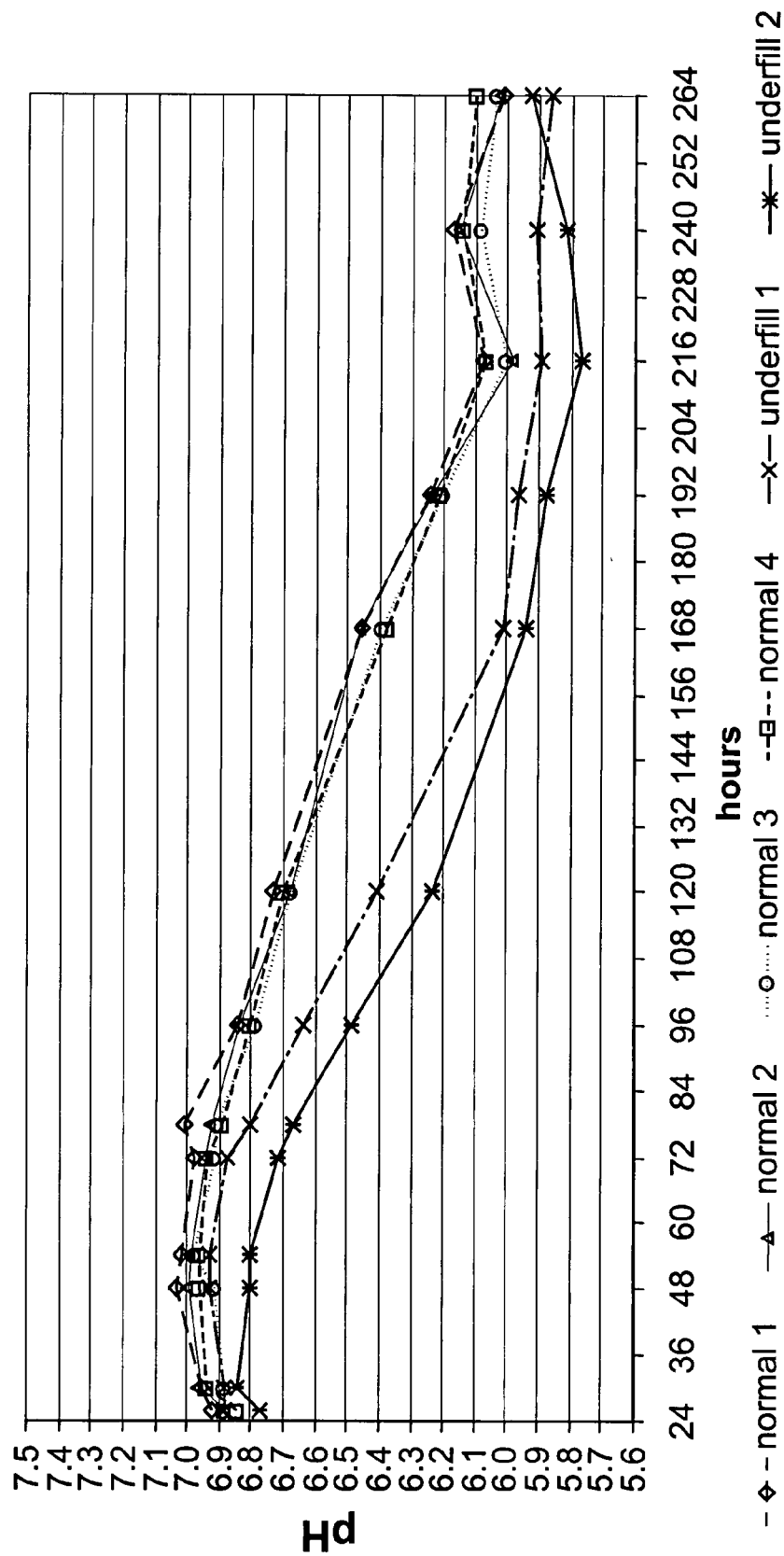
FIG. 8 is a graph comparing pH profiles for under-filled and normal-filled representative platelet storage bags.

To further demonstrate the utility of the invention, pH over time for platelets stored in representative small platelet storage bags was examined. Referring to FIG. 8, pH profiles were generated using the method and system of the invention for normal and under-filled small platelet storage bags. The normal bags contained 14 mL of apheresis platelets. The under-filled bags contained 7 mL of apheresis platelets from the same unit as the normal bags. The best storage conditions used 14 mL of PC per bag, and reproducible curves were obtained for these "normal" storage conditions. As shown in FIG. 8, if the bags are under-filled (7 mL of PC per bag), then the pH profile changes such that the pH drops more rapidly. This is the first demonstration that the non-invasive system for measuring the metabolic activity in the contents of a platelet storage bag over time can be used to find "abnormal" units. Other storage parameters such as abnormal leukocyte count or abnormal platelet concentration or novel parameters that influence platelet storage may also be detected using the non-invasive method of the invention. It is recognized that platelets recovered from some donors rapidly lose function and it is likely that these units can be discovered using a non-invasive system.

Figure 9A:
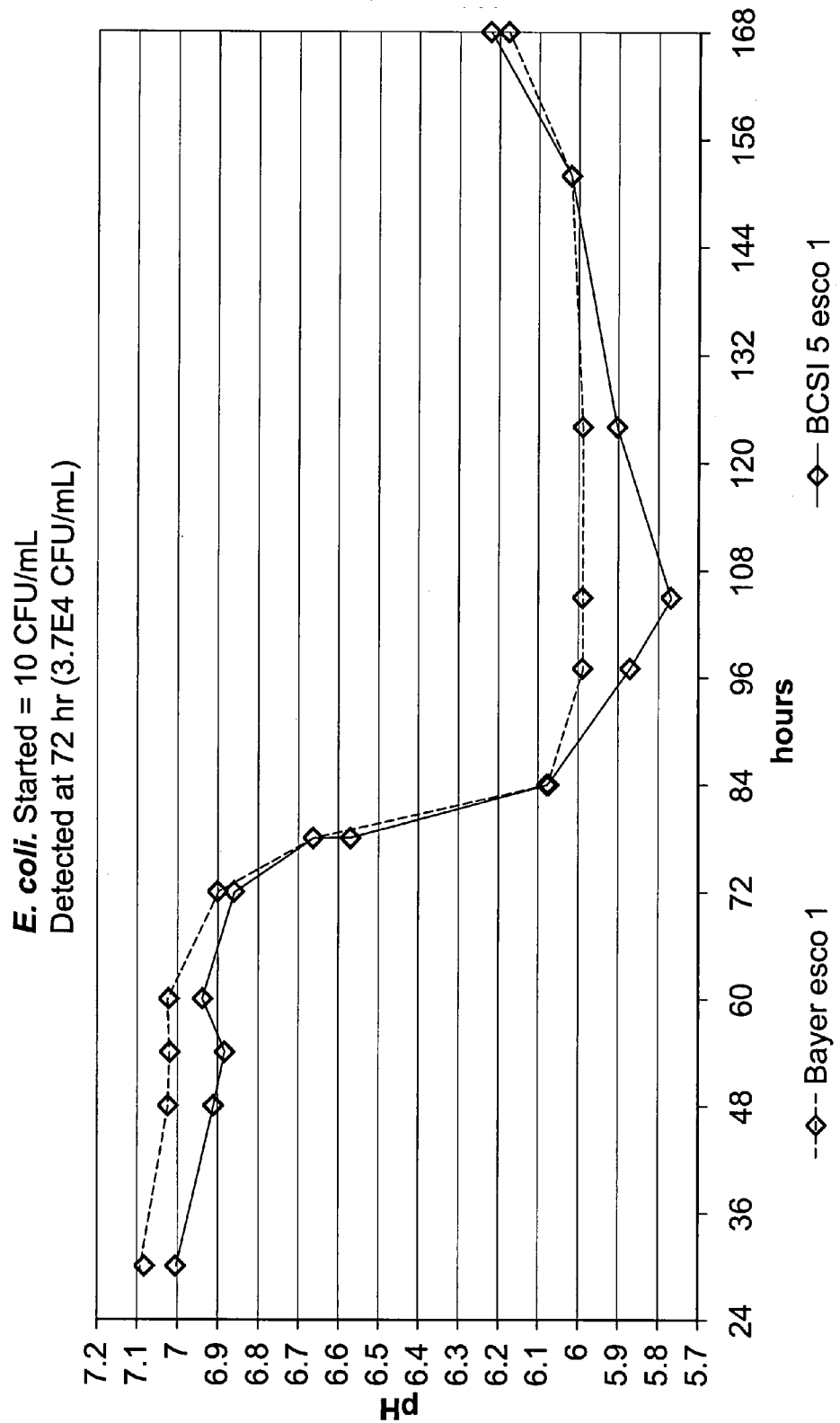
FIGS. 9A-9D are graphs illustrating pH profiles for platelet samples contaminated with different types of bacteria.
Figure 9B:
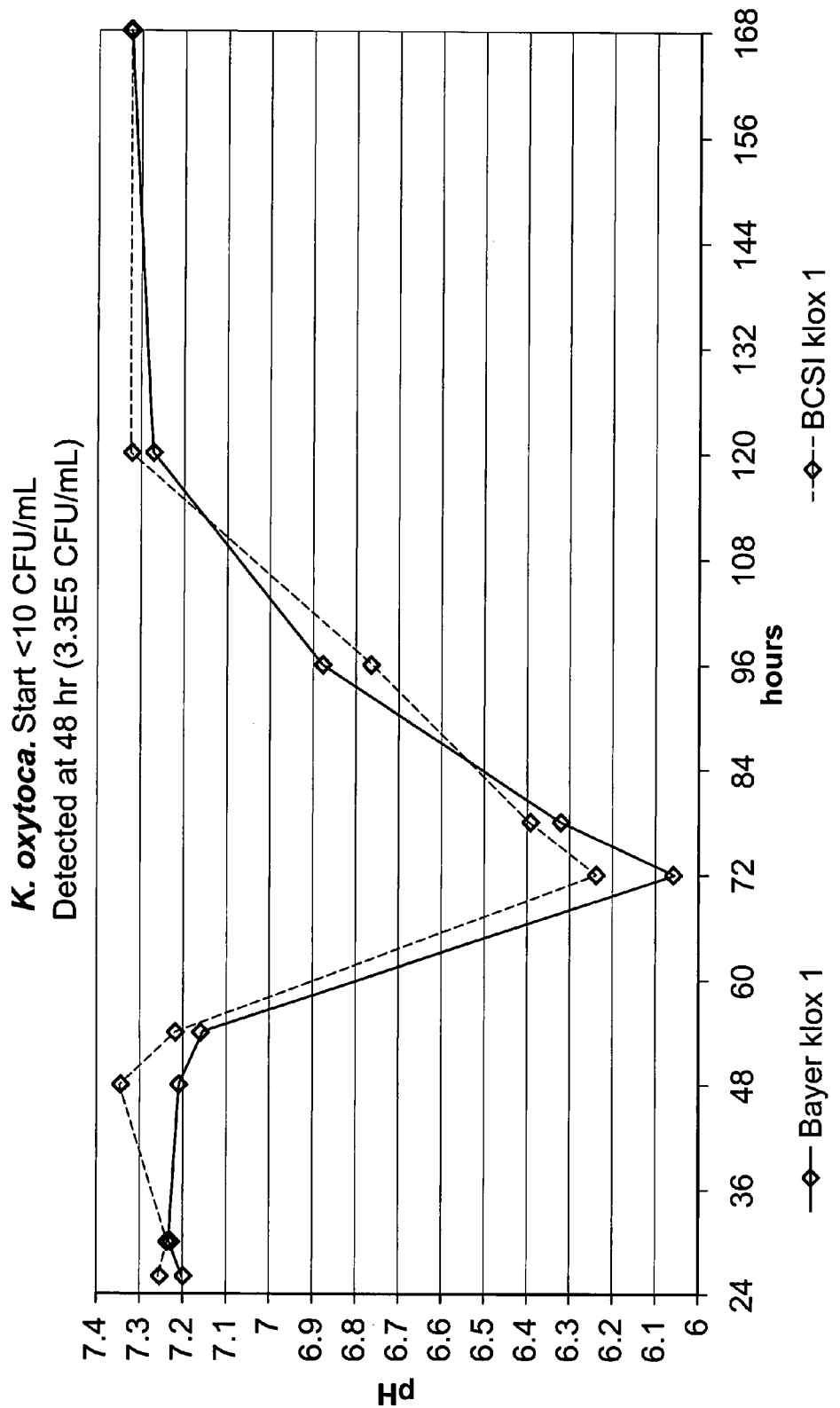
Figure 9C:
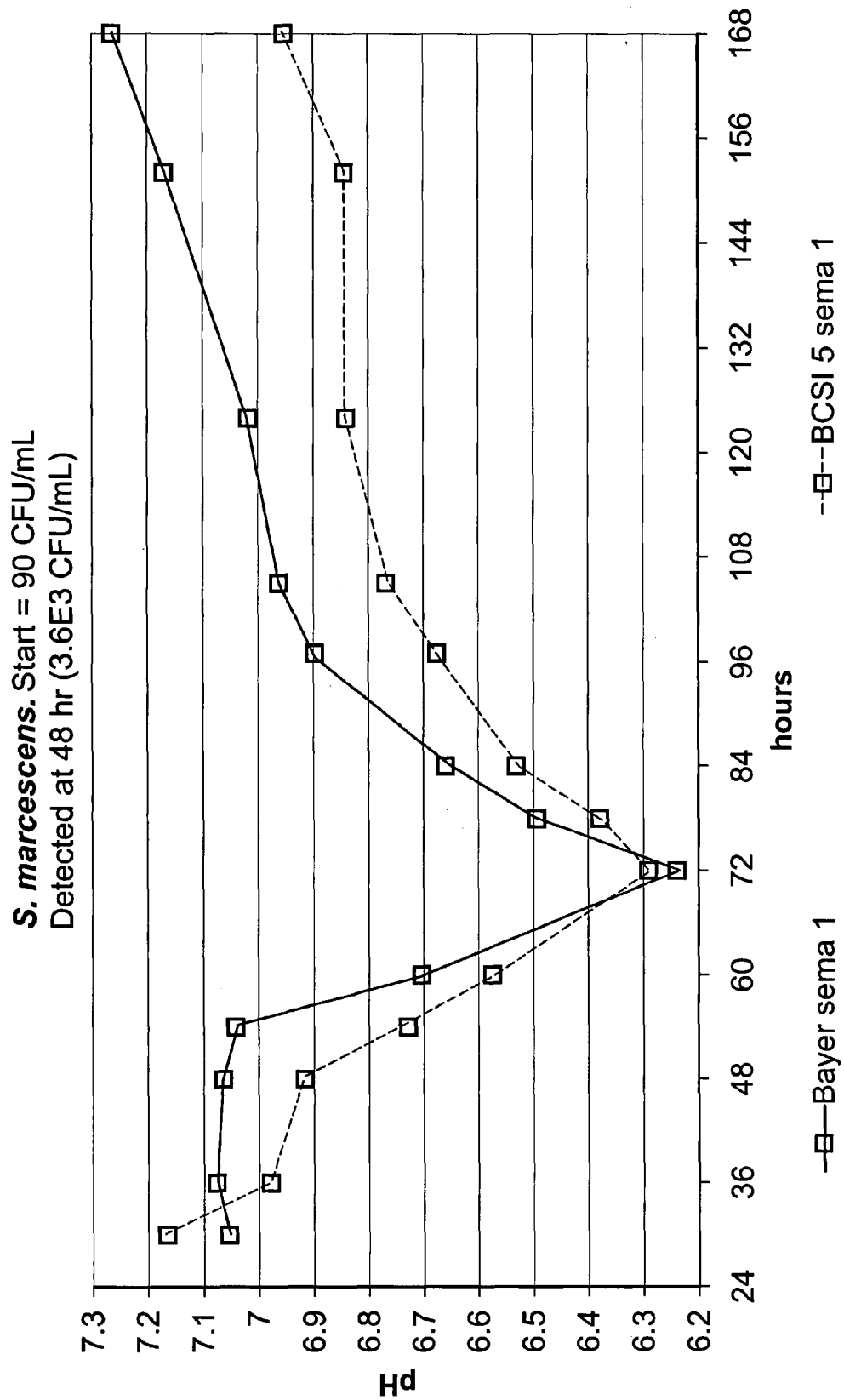
Figure 9D:
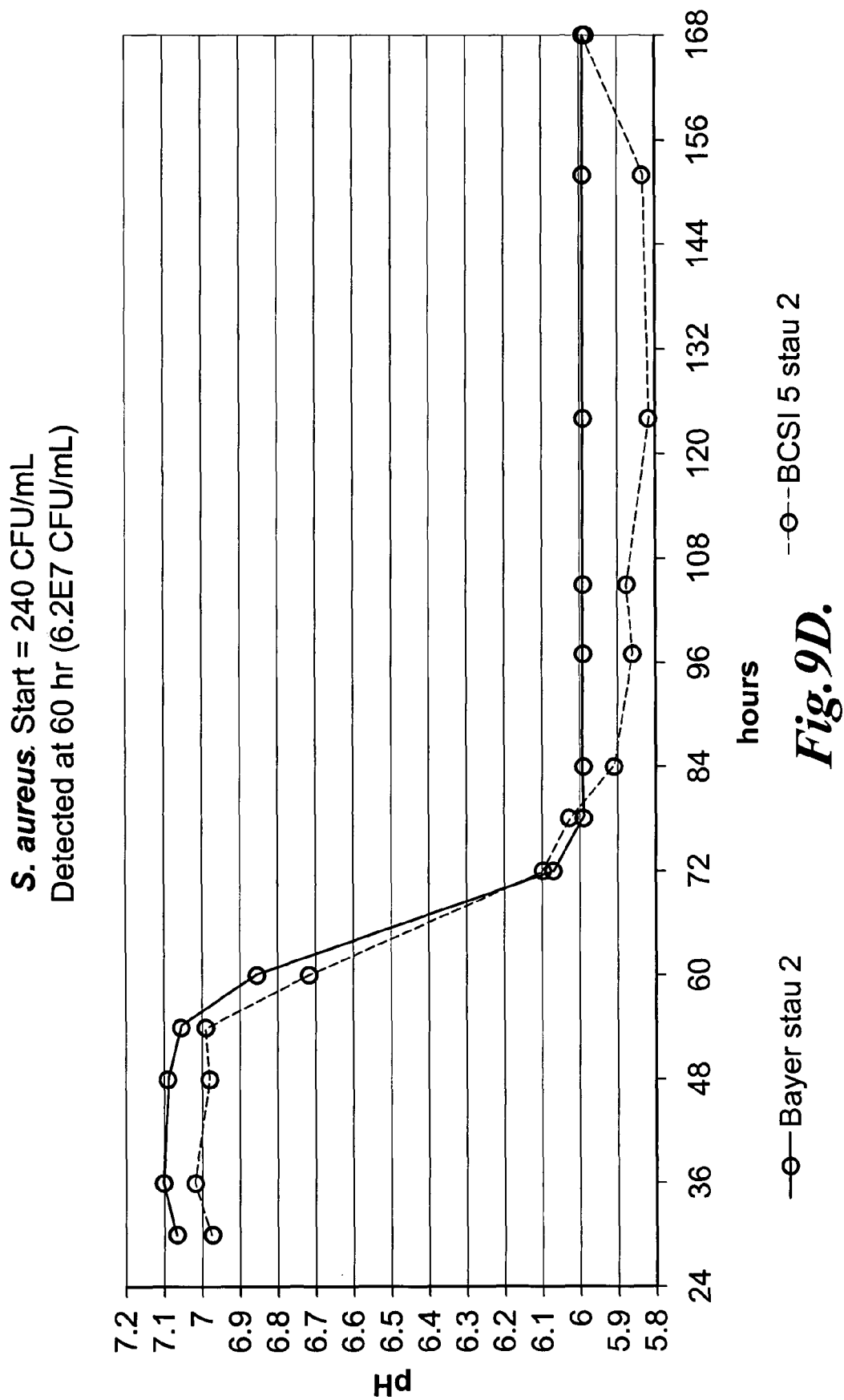

Bacterial contamination of platelets is a common problem, and the most life threatening of all blood transfusion events. Results of non-invasive pH measurements of small platelet bags inoculated with four common bacterial contaminants are shown in FIGS. 9A-9D. The bags were inoculated at 26 hours and detected at the inflection time point shown in each graph. All bags were incubated at 22° C. FIG. 9A represents a PC sample inoculated with 10 CFU/mL (Colony Forming Units/mL) of $E. coli$. The sample at 72 hours contained 3.7E4 CFU/mL bacteria. FIG. 9B represents a PC sample inoculated with 10 CFU/mL of $K. oxytoca$. The sample at 48 hours contained 3.3E5 CFU/mL of bacteria. FIG. 9C represents a PC sample inoculated with 90 CFU/mL $S. marcescens$. The sample at 48 hours contained 3.6E3 CFU/mL of bacteria. FIG. 9D represents a PC sample inoculated with 240 CFU/mL $S. aureus$. The sample at 60 hours contained 6.2E7 CFU/mL of bacteria.

Referring to FIGS. 9A-9D, pH was measured using a Bayer blood gas analyzer and a representative system and method of the present invention. All organisms tested in this cohort show a dramatic decrease in pH with ongoing bacterial growth. Concomitant invasive sampling with the blood gas analyzer confirmed the accuracy of the non-invasive pH measurement system. The "detection point" shown in FIGS. 9A-9D can be correlated with bacterial count upon examination of the rate of change in pH per unit of time over the course of the bag tracking pH measurements. The "detection point" can also be correlated with other chemical parameters or numerical ratios thereof as measured using various methods in these experiments. More frequent sampling would likely detect the bacteria at lower CFU.

Figure 10A:
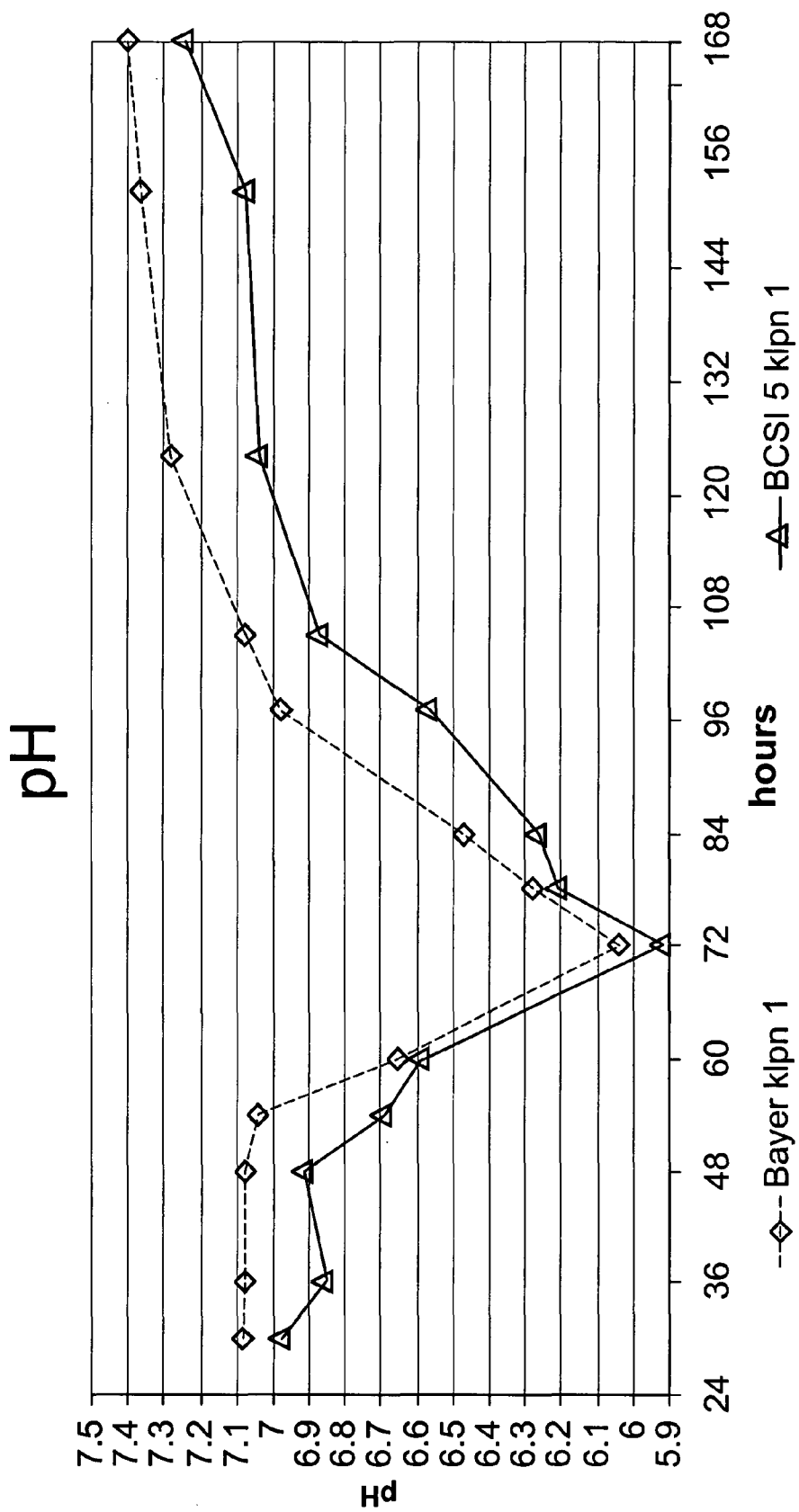
FIGS. 10A-10D are graphs illustrating the pH, glucose, $pO_2$, and $pCO_2$ profiles, respectively, of platelet samples contaminated with bacteria.
Figure 10B:
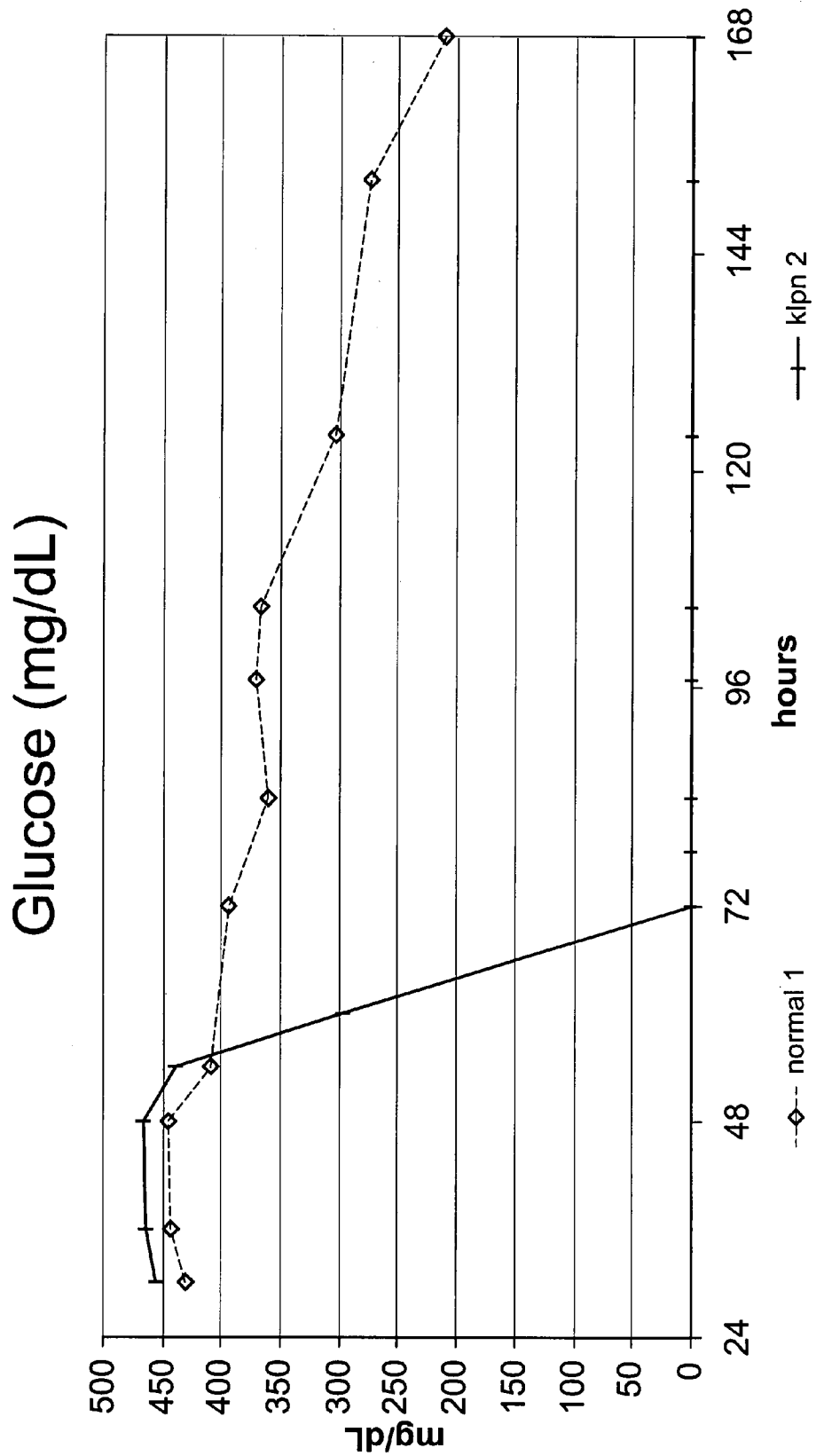
Figure 10C:
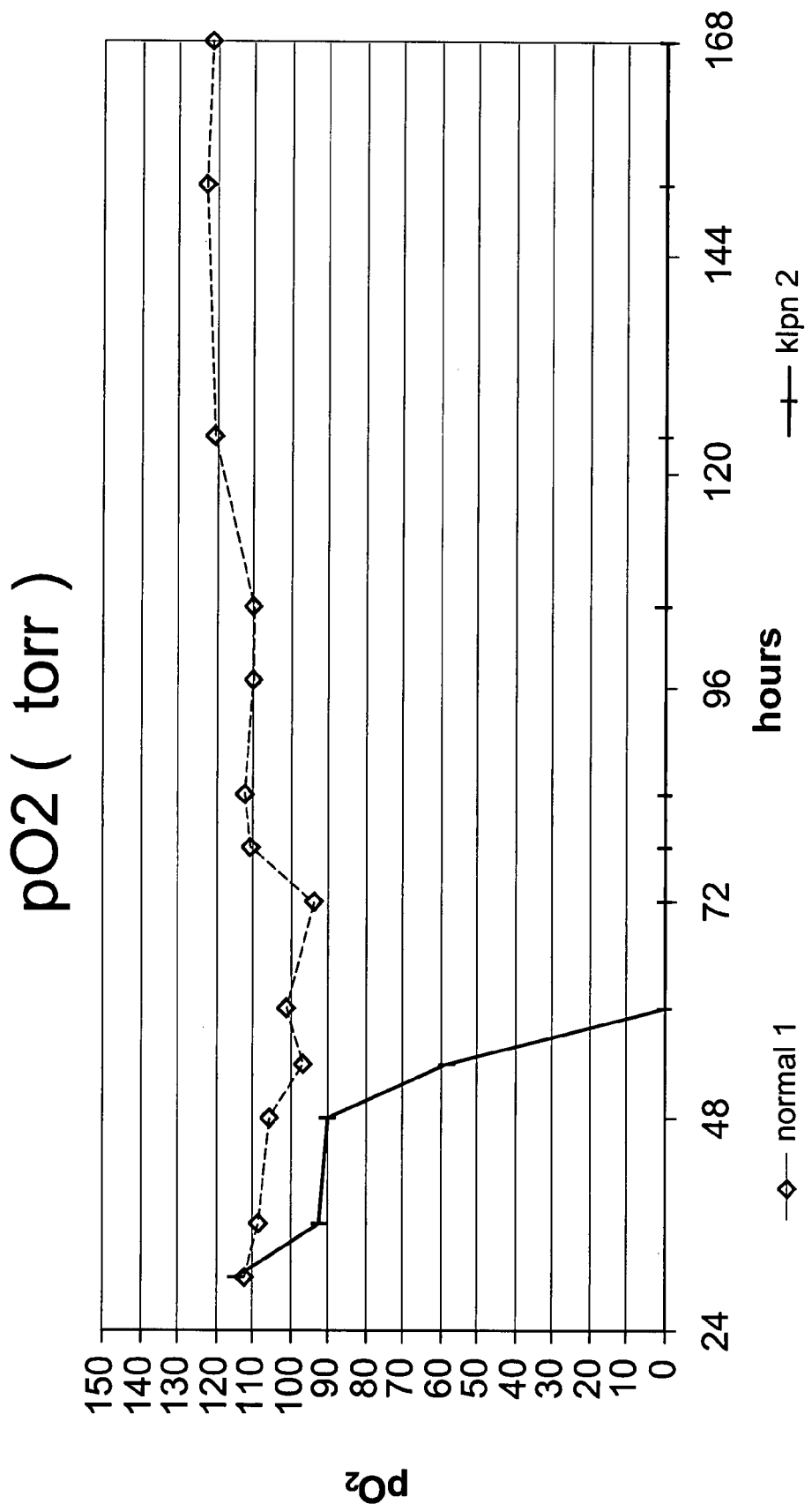
Figure 10D:
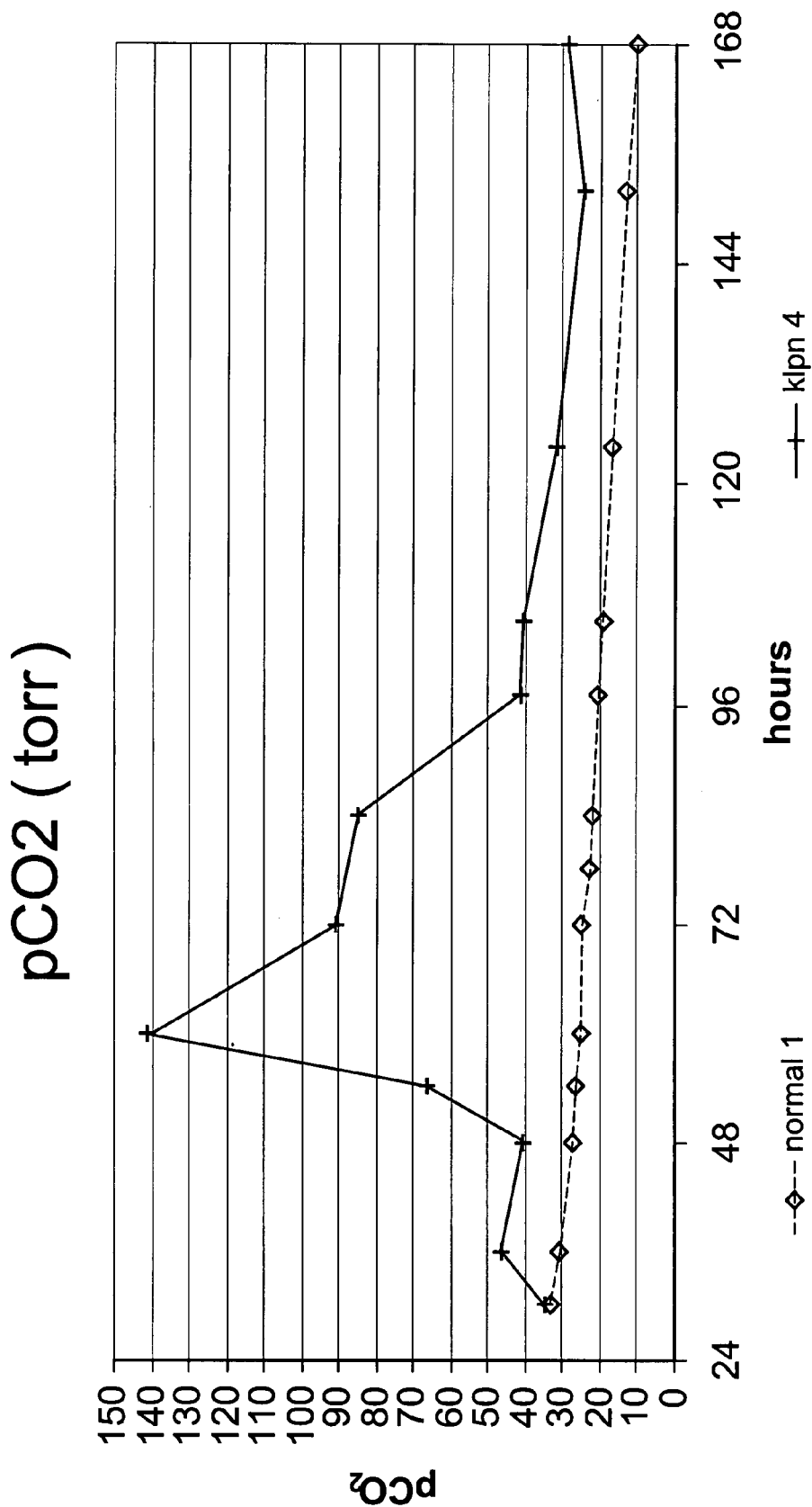

The value of measuring other analytes associated with metabolizing platelets in storage bags is shown in FIGS. 10A-10D. Small storage bags were inoculated with 10 CFU/mL of $K. pneumoniae$. Partial pressures of oxygen and carbon dioxide were measured on a blood gas analyzer at various timepoints. Glucose concentrations were measured using a commercial dipstick method at the same timepoints. The pH measurements in FIG. 10A show paired blood gas and pH readings for a single inoculated bag. The $O_2$, $CO_2$, and glucose graphs in FIGS. 10C, 10D, and 10B, respectively, compare inoculated and "normal" platelet concentrates. Bacterial contamination of the platelet concentrates can also be correlated with these other chemical parameters, or numerical ratios thereof, as measured using various methods in these experiments as shown in FIGS. 10A-10D.

Figure 11:
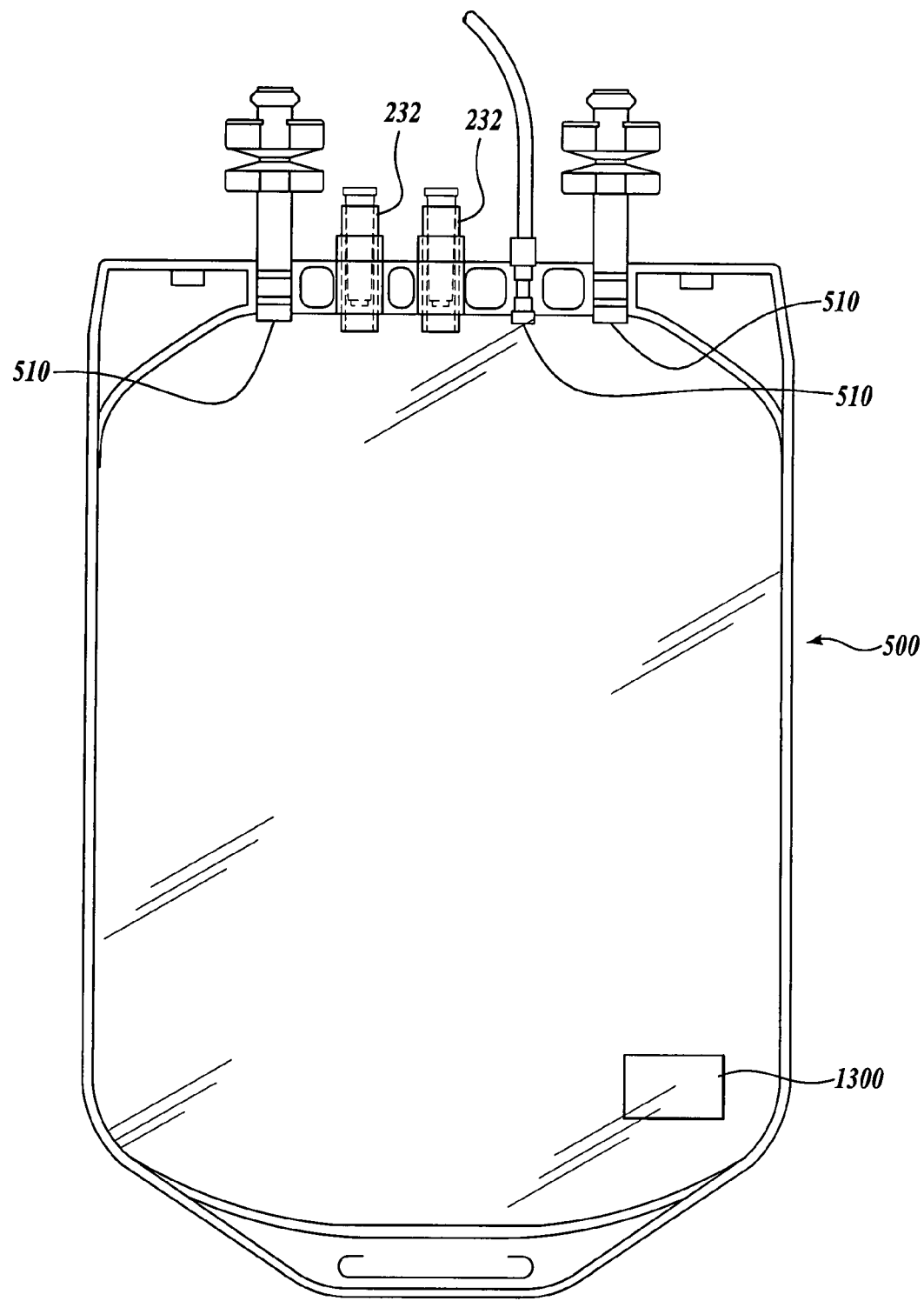
FIG. 11 illustrates a representative multi-probe platelet storage bag useful in the method and system of the invention.

FIG. 11 illustrates a representative multi-probe platelet storage bag with two inserts, one for measuring pH and the other for measuring $CO_2$. Referring to FIG. 11, storage bag 500 includes a plurality of vessel ports 510, port assembly 232, and port assembly 232. Storage bag 500 includes label 1300, into which a memory device can be integrated (not shown). By integrating a memory device into label 1300, parameter readings can be written to and stored on storage bag 500 that contains the sample.

Thus, in one embodiment, the invention provides a method of monitoring (e.g., measuring and recording) at least two chemical parameters in a sealed sterile platelet storage device. In the method, the parameters monitored indicate platelet healthiness (e.g., low pH) or microbial contamination (e.g., $CO_2$ spike).

Storage of the platelet units at 22° C. in a shaking incubator is standard in all blood banks worldwide. Although fluorescence readers can be used to rapidly measure pH, it still requires individual handling of every bag at each time point. To alleviate this problem, in one embodiment, the invention provides an incubator that facilitates automated reading.

Figure 12:
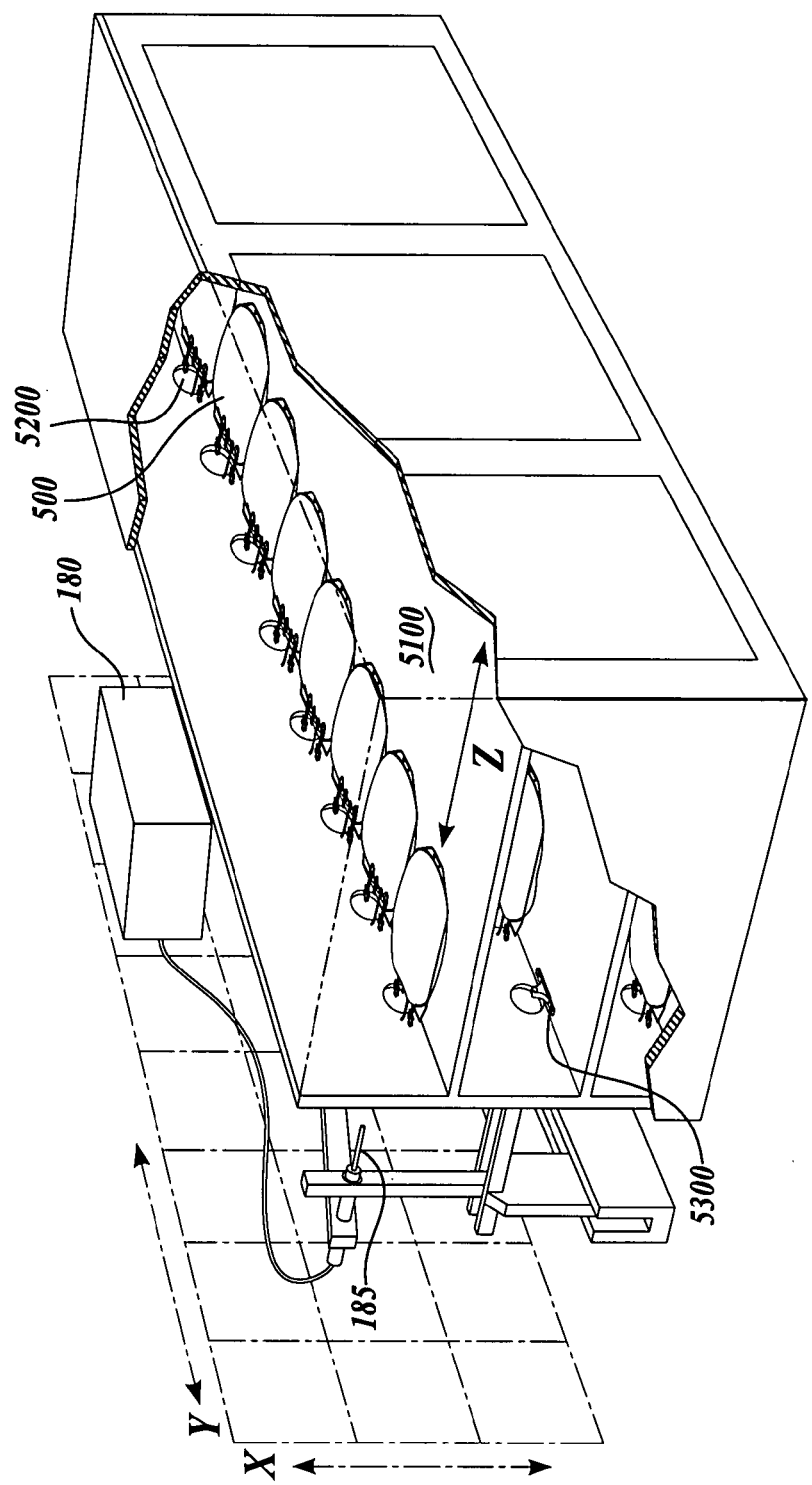
FIG. 12 is a schematic illustration of an automated single reader.

In one embodiment, a single reader incubator with a flexible probe is provided. The probe is mechanically moved to different positions on the back of the incubator using an x,y,z robot. Referring to FIG. 12, an optical platform 180 is located proximate to a shelving unit that is configured to receive platelet storage bags 500. The optical platform 180 is more fully described below (see FIG. 19). Platelet storage bags 500 are placed on shelves 5100 by a user. A plurality of apertures 5200 are disposed towards the distal end of each shelf. Clamps 5300 are located at each aperture 5200. Each bag 500 may be secured through an aperture 5200 using clamp 5300. A probe 185 is connected by optical fibers (light guides) to optical platform 180. Probe 185 is enabled to maneuver within an x,y,z grid. The z dimension involves reversible insertion of the probe 185 into the clamped insert for each bag 500 at a specified x,y position. Any number of bags may be placed in the incubator provided there are sufficient apertures 5200 to receive them.

Figure 13:
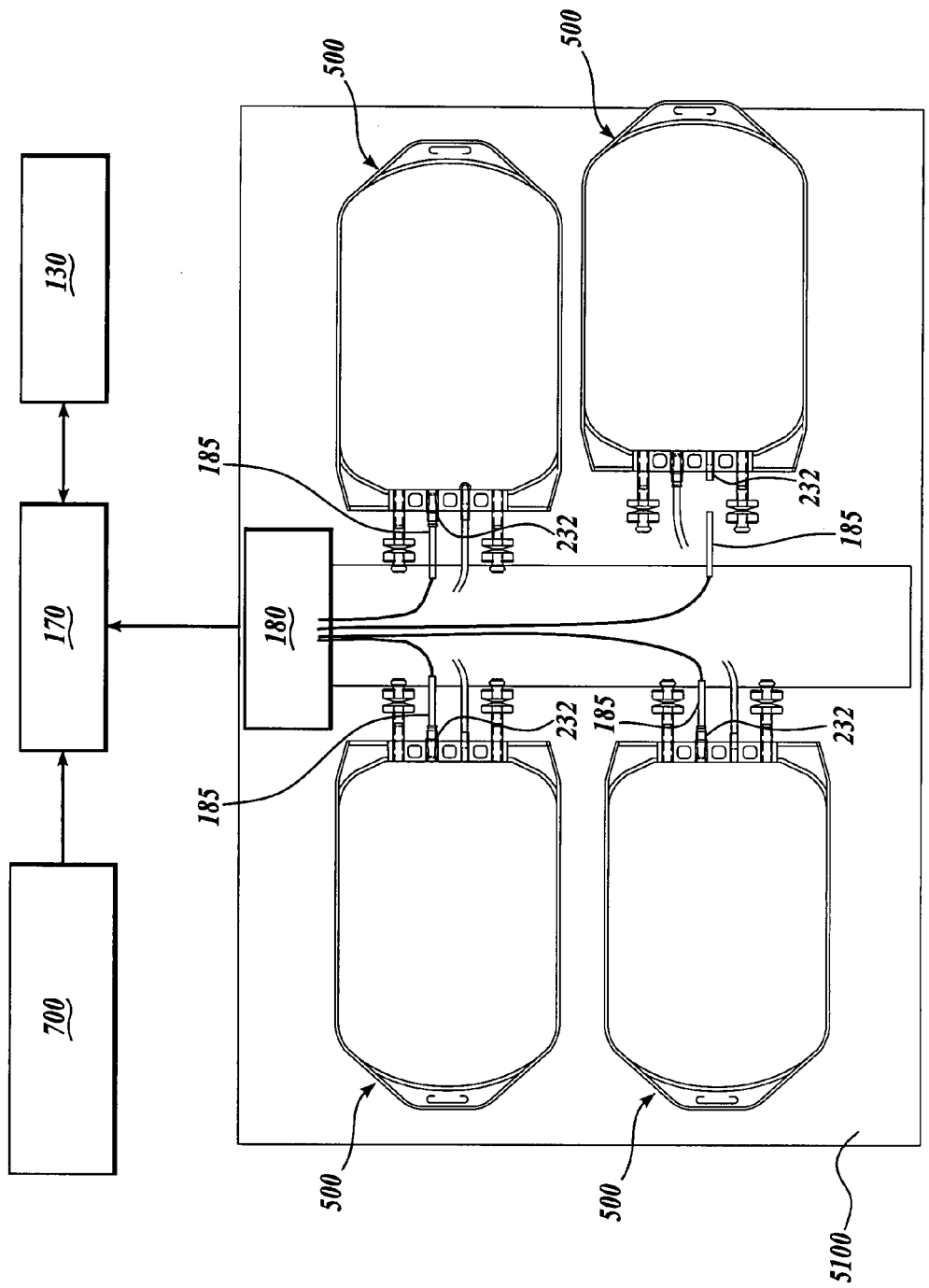
FIG. 13 is a schematic illustration of a multi-fiber reader.

In another embodiment, a single reader incubator is configured with multiple fiber bundles. Referring to FIG. 13, multiple bags 500 with sensors are each connected to separate probes 185 by a user and left attached to the probes. Separate probes 185 are connected to optical platform 180 by optical fibers (light guides). Optical platform 180 is more fully described below (see FIG. 19). The fiber optics in the probes 185 convey excitation light to the sensor and fluorescent emissions back to the detector within the optical platform 180. The excitation light can be split from one light source and piped to multiple probes 185 and bag sensors by physically blocking the excitation fiber optics so the fiber optic for only one probe is excited.

For example, if four probes (1, 2, 3, and 4) are connected to a single excitation source a moving shutter blocks the light collection ends of probes 1, 2 and 3 to only allow light to travel to probe 4. Then the shutters are changed to block the ends of probes 2, 3, and 4 allowing excitation only to probe 1. Each of the dual emissions from the sensors are collected with light for each channel from all the probes focused on a single detector. For example, a system with four probes (1, 2, 3, and 4) and emission readings A and B for each probe, would have two detectors A and B. Detector A would have all the light from probe 1A, 2A, 3A, and 4A focused on it and likewise with detector B. Then depending on what probe was excited by means of the physical blocking, the emission readings can be tied to which probe was excited. A plurality of bags could be studied with a single excitation and emission system in this way also a plurality of these excitation and emission systems 700 could be incorporated into a single central processor 170, with output to user interface and display 130.

Figure 14:
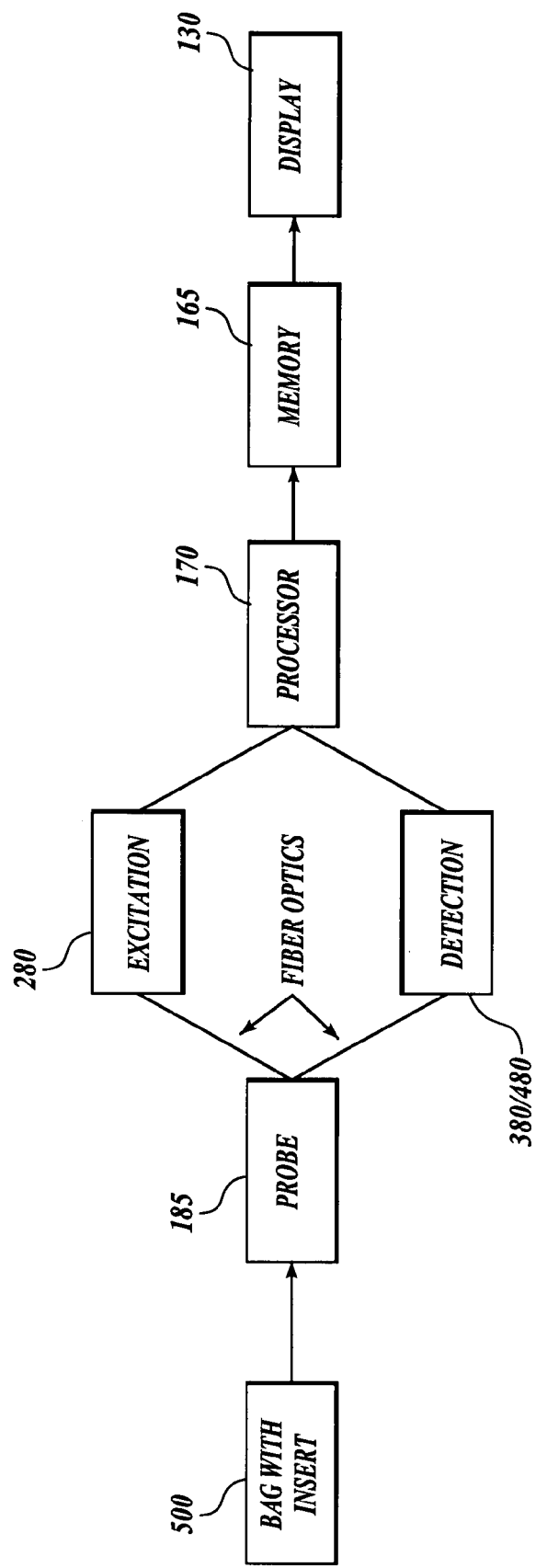
FIG. 14 is a schematic illustration of an incubator.

FIG. 14 is a schematic illustration for the incubators described in FIGS. 12 and 13. Referring to FIG. 14, the schematic illustration shows how the components of a representative system for carrying out the method of the invention are adapted and connected to make an incubator. System components include display 130 for determining the status of the system and viewing pH determination results; memory device 165 for storing test results and calibration data; signal processing electronics 170 for commanding the optical platform components and processing signals from the optical platform; and optical platform 180 including an excitation source 280, emission detectors 380 and 480, light guides, and associated lenses and filters. Optical platform 180 includes probe 185. Probe 185 is reversibly connectable to bag 500 with insert.

In one embodiment, an incubator machine may have one probe 185 that connects to multiple bags 500, as shown in FIG. 12. In another embodiment, an incubator machine may have multiple probes 185 and a single optical platform 180, as shown in FIG. 13. In yet another embodiment, an incubator machine may have multiple probes 185 with multiple excitation sources 280 and emission detectors 380 and 480. The basic structure for this embodiment is shown in FIG. 14.

To have practical utility, the parametric information (e.g., pH) obtained by the systems and methods of the invention need be stored and analyzed. There are several options for storing and analyzing the obtained data. Multi-read data can be stored for real-time analysis on a memory device, such as a chip, that is integrated into the storage bag (i.e., vessel) itself. The memory device is read/write capable in order to receive information and store it for later analysis. In this way, data are directly linked to the bag and follow the bag from one location to the next. For example, a bag may be transferred from a donor center to a research laboratory or hospital blood bank. Storing the data on a memory device that is integrated into the bag allows the data to be read directly from the storage bag prior to being analyzed.

In one embodiment, data of the pH and other analytes can be stored on a memory device attached to the platelet bag. A Texas Instruments S2000 RFID transponder and corresponding low-frequency RFID tags were employed as a proof of principle platform. The available RFID tags were limited in memory capacity, having at most 80 bits available for read/write operations. To overcome this memory limitation, pH values were encoded to have a range such that pH 6.2 and 7.8 corresponded to hexadecimal values zero (0) and fifteen (F), respectively. In binary representation each hexadecimal value requires four bits.

The representative system of the invention (BCSI pH1000, Blood Cell Storage, Inc., Seattle, Wash.) was coupled to the RFID system through a personal computer. An RFID antenna was fitted inside the pH1000 casing. Software was written in Matlab to integrate the functions of the pH11000 and S2000. When a transponder entered the antenna range, data was automatically read from the RFID tag and the user prompted to perform a reading. Subsequent to additional measurements on the pH1000; new data was appended to the RFID tag.

Bags can be identified and tracked by integrating an RFID chip in the bag itself as a means for writing data to the vessel containing the sample. Referring to FIGS. 1 and 2, the chip can be integrated in the label 130 of bag 500. Bags can also be identified and tracked by identifying each bag with a unique bar code. The bar code on the platelet storage bag can also be used for other identification information, for example, to identify the bag's position in the incubator. When data are stored on an RFID chip, there is no need to identify the bag position in the incubator.

Another data storage option is to store data on a central computer that is linked to the system for monitoring pH. When data are collected, they are transferred to a central computer where they are stored. The central computer is equipped to generate a pH profile using data that it has accumulated. Yet another option is to store data directly on the reader. Data can be processed on the reader to generate a pH profile, or can be transferred to a central computer that generates the pH profile.

To advise regarding the quality of the sample in the vessel interrogated by the systems and methods of the invention, pass/fail algorithms may be utilized that examine the rate of change in pH per unit of time over the course of the bag tracking in an automated fashion. A drop in pH greater than some threshold value as defined from examination of a plurality of data would constitute assignment and reporting of a FAIL value which will be associated with the particular bag being examined.

In one aspect of the invention, a method for monitoring pH of a sample is provided. In the method, pH is determined by comparing fluorescent emission intensities from a single fluorescent species having pH-dependent fluorescent emission. The fluorescent species having pH-dependent fluorescent emission has a first emission intensity at a first wavelength and a second emission intensity at a second wavelength, the first and second emission intensities being characteristic of pH in the environment of the fluorescent species. The ratio of the first and second emission intensities provides pH measurement. Calibration of the first and second emission intensities provides an intensity-based reference (ratio information) that is used to determine the pH of the environment of the fluorescent species.

In one embodiment, fluorescent signal analysis of the ratio of first and second emission wavelengths is used to calculate the resulting pH. Fluorescent signal analysis and analysis of the pH algorithm are performed as follows. The instrument collects the fluorescent intensities at 568 nm (fr) and at 600 nm (fp), and then calculates the ratio of the fp to fr signals. The pH has been found to be a function of the ratio and the fp value described as pH=f(ratio)+g(fp). The f(ratio) function is nonlinear while the g(fp) function is linear. The best description of the f(ratio) is Constant1*ln(ratio)+Constant2. The instrument then uses a lookup table, such as the lookup table in FIG. 15, to find the appropriate value for the f(ratio) function and then calculates the g(fp) adjustment and calculates a pH. Because the intensities of the fr and fp channels are dependent on optical path and the instrument hardware, the intensity values obtained from a single part are not identical for each instrument. However, the differences between these intensities are linearly related and thus it is possible to compare the results from one instrument to another as well as create the f(ratio) and g(fp) relationships on a different instrument than the instrument that the calibration of pH and fluorescent signal was performed on.

Figure 15:
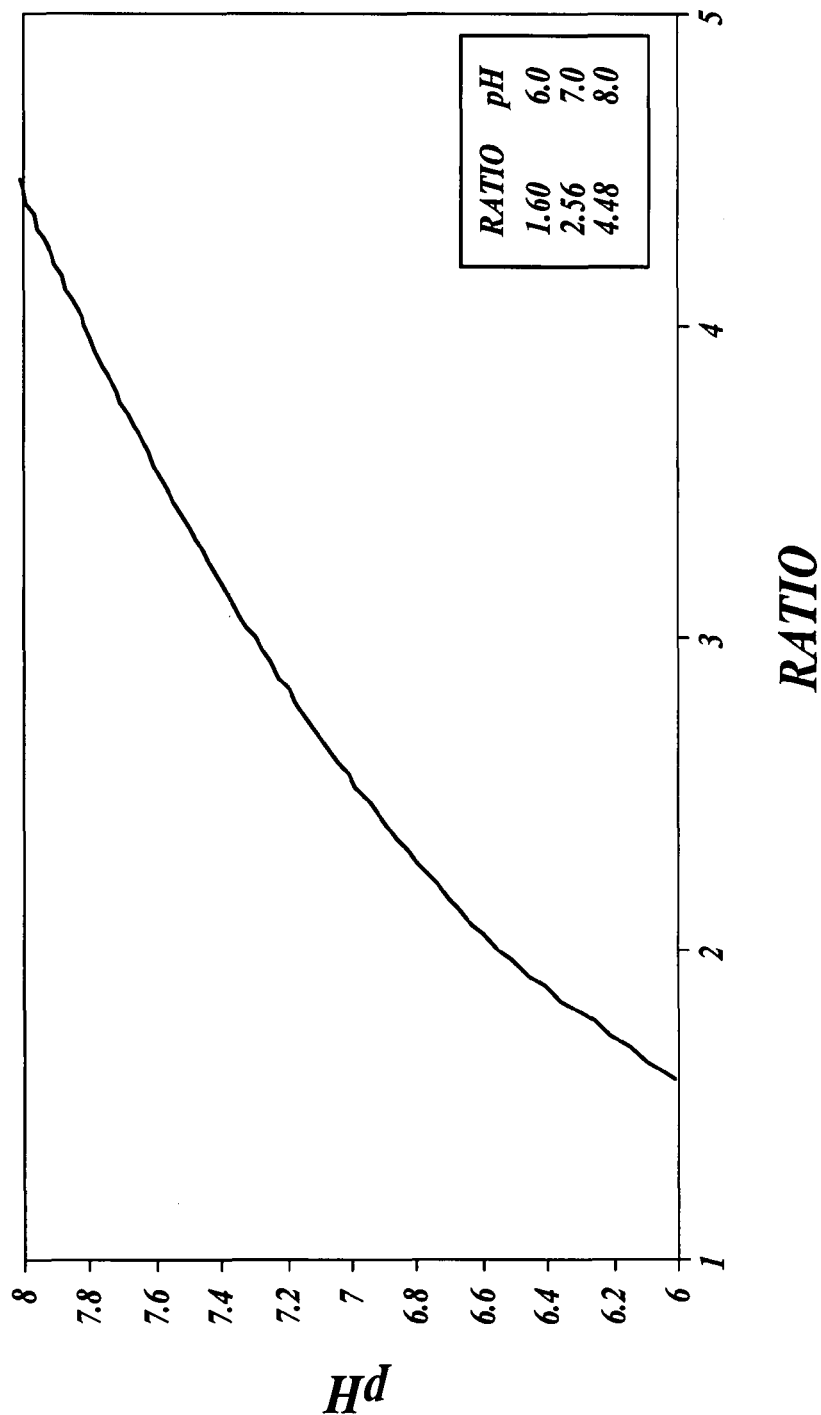
FIG. 15 is a graph relating fluorescent intensity ratio to pH of PCs.

FIG. 15 is a graph of a mathematical function of the ratio of first and second emission intensities as related to pH. This type of graph is also known as a lookup table, and is useful in the method and system of the present invention. For example, according to the lookup table in FIG. 15, a ratio of 1.6 corresponds to pH 6.0; a ratio of 2.56 corresponds to pH 7.0; and a ratio of 4.48 corresponds to pH 8.0.

Figure 16:
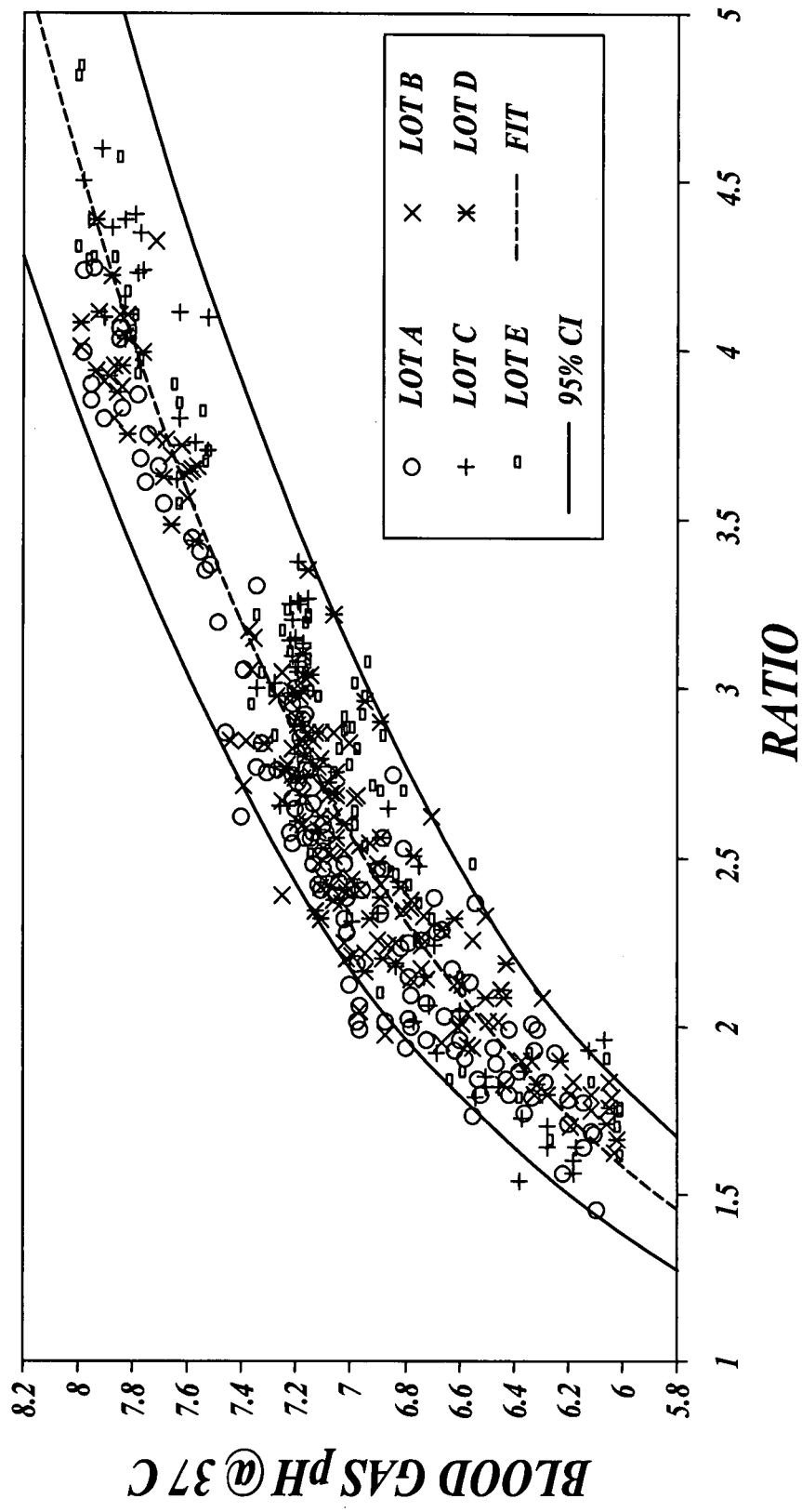
FIG. 16 is a graph relating fluorescence intensity ratios to blood gas pH of PCs.

The lookup table in FIG. 15 is generated from calibration data depicted in FIG. 16. FIG. 16 shows the data from calibration studies of five lots. Individual lookup tables are possible for each lot or as FIG. 16 demonstrates the lots when compared to one lookup table agree within +/−0.159 pH units. Calibration data is collected in the manner described in Example 7. Apheresis platelets and plasma are separated into large platelet bags rigged to resemble the small bag (see FIG. 2). Four groups are followed over time to give a suitable range of pH. The four groups are: (1) normal—standard fill of 12-15 mLs to generate pH decline over the shelf life of the platelets, (2) plasma—to generate high pH range, (3) underfills—fill of only 7 mLs, and (4) bacterially spiked—standard fill with the addition of 100 CFU/mL of *Klebsiella oxytoca* after the 24 hour read to generate very low pH. Readings are initially performed after 4 hours of equilibration, then twice daily through four days and once daily for the remainder of 7-10 days.

Figure 17:
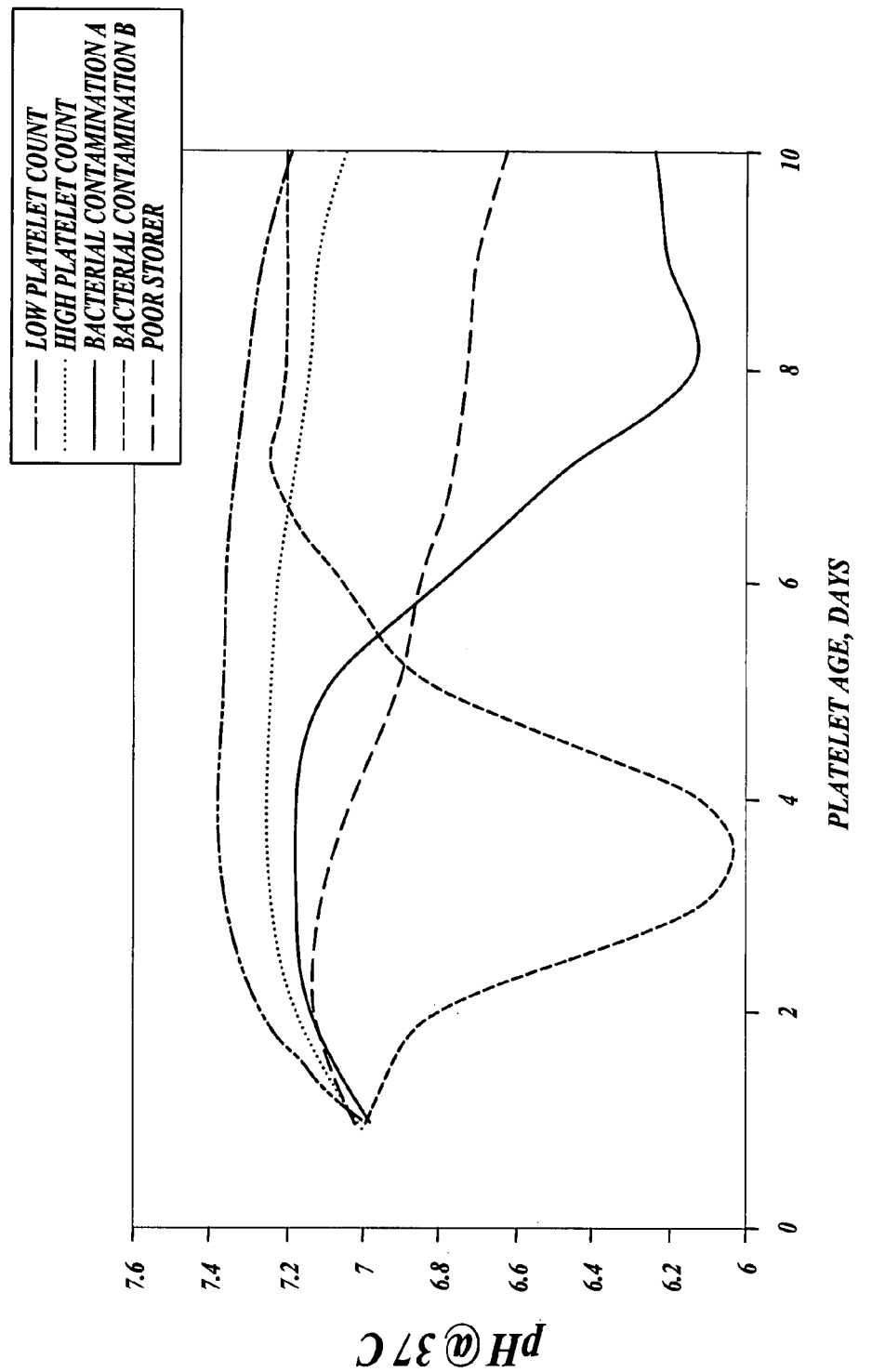
FIG. 17 is a graph comparing pH profiles of various types of platelet samples.

Platelet pH trends were analyzed to determine acceptable and unacceptable rates of change for stored platelets. The rate of change can be used to determine the quality of stored PC. Referring to FIG. 17, pH profiles were generated for 5 types of platelets: PC sample with a low platelet count, PC sample with a high platelet count, two PC samples with bacterial contamination, and PC sample that is a "poor storer." After an initial rise in pH attributable to $CO_2$ off gassing, pH rates of change can be described as follows. PC samples with a high platelet count had a pH drop of about 0.02 pH units per day. PC samples with a low platelet count had a pH drop of about 0.04 pH units per day. pH drops in this range are characteristic of good quality PCs that are usable. In comparison, poor storing PCs had a pH drop of about 0.08 pH units per day, and bacterially-contaminated PCs had a pH drop of about 0.2 pH units per day. pH drops in this range are characteristic of poor quality PCs that are unusable.

To further understand the systems and methods of the invention, the following detailed description is provided.

In one embodiment, the fluorescent species having pH-dependent fluorescent emission is immobilized on a substrate in contact with the sample such that the fluorescent species is in contact with the sample. The immobilized fluorescent species in contact with the sample is located in the sample such that the fluorescent species can be interrogated. The fluorescence measurement is made by irradiating the fluorescent species at a wavelength sufficient to elicit fluorescent emission, which is then measured. Because of the pH-dependent nature of the fluorescent species' emission profile (i.e., first and second fluorescent emission intensities measured at first and second emission wavelengths, respectively) the measurement of the fluorescent emission profile yields the pH of the fluorescent species' environment (i.e., sample pH).

In one embodiment, the sample for which the pH is to be determined is contained in a sealed vessel. As noted above, this method is suitable for measuring pH of blood and blood products sealed in a conventional blood storage vessel.

In another embodiment, the sample for which the pH is to be determined is contained in an open vessel. As used herein, the term "open vessel" refers to a vessel that is not sealed. In this method, the probe is cleaned and/or sterilized and is used once and discarded. This method is suitable for measuring the pH of materials used in food, pharmaceutical, or biological research where the vessel containing the material is not sealed (i.e., open). Such a "lab-use" system includes a tip (see description below) placed onto the probe. The pH measurement is made by immersing the tip into the sample and measuring pH. The tip is removed from the sample, removed from the probe, and discarded.

In the method for measuring the pH of a contained sample, the fluorescent species (e.g., substrate-immobilized fluorescent species) is introduced into the vessel either before or after the sample is placed in the vessel. The sealed vessel prevents the contents of the vessel from contact from, for example, liquids, gases, or contaminants outside of the vessel. The sealed vessel also prevents the contents of the vessel from escaping the vessel.

The vessel can be manufactured to include the substrate-immobilized fluorescent species as a component of the vessel. In such an embodiment, the substrate-immobilized fluorescent species is incorporated into the vessel during manufacture to provide a vessel into which a sample can be later introduced and its pH measured. The manufacture of a vessel incorporating the substrate-immobilized fluorescent species is described in Example 1.

Alternatively, the substrate-immobilized fluorescent species can be introduced into the vessel after the sample has been introduced into the vessel. In such an embodiment, the substrate-immobilized fluorescent species is introduced into the vessel by a process in which the vessel is first punctured (or spiked) to introduce the substrate-immobilized fluorescent species and then resealed to provide a sealed vessel including the sample now in contact with the substrate-immobilized fluorescent species. The process for introducing the substrate-immobilized fluorescent species into a sealed vessel is described in Example 2.

As noted above, the vessel including the substrate-immobilized fluorescent species in contact with the sample is sealed before, during, and after interrogation. Interrogation of the fluorescent species requires excitation of the species at a wavelength sufficient to effect fluorescent emission from the species and measurement of that fluorescent emission. In the method of the invention, interrogation is accomplished through a window in the sealed vessel. The fluorescent species is excited by irradiation through the window, and emission from the fluorescent species is collected from the fluorescent species though the window. The window is a component of the sealed vessel and allows for interrogation of the fluorescent species in contact with the sample. The window is sufficiently transparent at the excitation and emission wavelengths to permit interrogation by the method. The substrate-immobilized fluorescent species is positioned in proximity to the window sufficient for interrogation: proximity sufficient to effectively excite the fluorescent species and to effectively collect emission from the fluorescent species. It will be appreciated that for epifluorescence applications, a single window is used. However, other methods and devices of the invention can include other optical paths, such as straight-through or right angle optical paths, where more than one window can be used.

The method of the invention includes irradiating the fluorescent species, which in one embodiment is contained along with a sample in a sealed vessel, at a wavelength sufficient to effect emission from the fluorescent species and to measure that emission. Exciting light and fluorescent emission pass through the sealed vessel's window. In one embodiment, the sealed vessel further includes a port for receiving a housing that holds the excitation light guide and emission light guide. In one embodiment, the excitation light guide includes one or more optical fibers that transmit the excitation light from a light source to the fluorescent species. In one embodiment, the emission light guide includes one or more optical fibers that transmit the emission light from the fluorescent species to a light detector. The port receiving the housing is positioned in proximity to the window sufficient for interrogation: proximity sufficient to effectively excite the fluorescent species and to effectively collect emission from the fluorescent species.

As with all optical fluorescent methods, the method of the invention includes a light source for exciting the fluorescent species and a detector for measuring the emission of the fluorescent species. Light sources, wavelength selection filters, and detectors are selected based on the absorbance and emission profiles of the fluorescent species used in the method.

Suitable light sources provide excitation energy at a wavelength and intensity sufficient to effect fluorescent emission from the fluorescent species. The light source can provide relatively broad wavelength band excitation (e.g., ultraviolet or white light sources) or relatively narrower wavelength band excitation (e.g., laser or light-emitting diode). To enhance excitation efficiency and emission measurement, relatively broad wavelength band exciting light from the source can be selected and narrowed through the use of diffraction gratings, monochromators, or filters to suit the fluorescent species. Suitable light sources include tungsten lamps, halogen lamps, xenon lamps, arc lamps, LEDs, hollow cathode lamps, and lasers.

Suitable detectors detect the intensity of fluorescent emission over the emission wavelength band of the fluorescent species. To enhance emission measurement, fluorescent emission from the fluorescent species source can be selected and narrowed through the use of diffraction gratings, monochromators, or filters to suit the fluorescent species. Suitable detectors include photomultiplier tubes and solid state detectors, such as photodiodes, responsive to the wavelength emission band of the fluorescent species. Other suitable detectors are photovoltaic cells, PIN diodes, and avalanche photodiodes.

Through the use of filters, all of the excitation light that reflects off the target is filtered out before reaching the detector. This can be achieved by using filters in both the excitation and emission optical paths. In certain instances, reflected excitation light (which is many orders of magnitude more intense than the emission light) that reaches the detector can swamp the specific signal. Generally, 10E5 ($10^5$) or greater out-of-band rejection is appropriate in each of the filter sets. Reduction of excitation light can also be achieved by using an angled window so that reflected light is directed away from the emission detector. However, such an optical path is not as effective as filter sets.

Excitation light from the source can be directed to the fluorescent species through the use of a light guide, such as one or more optical fibers. Similarly, emission from the fluorescent species can be directed to the detector through the use of a light guide, such as one or more optical fibers.

Figure 18:
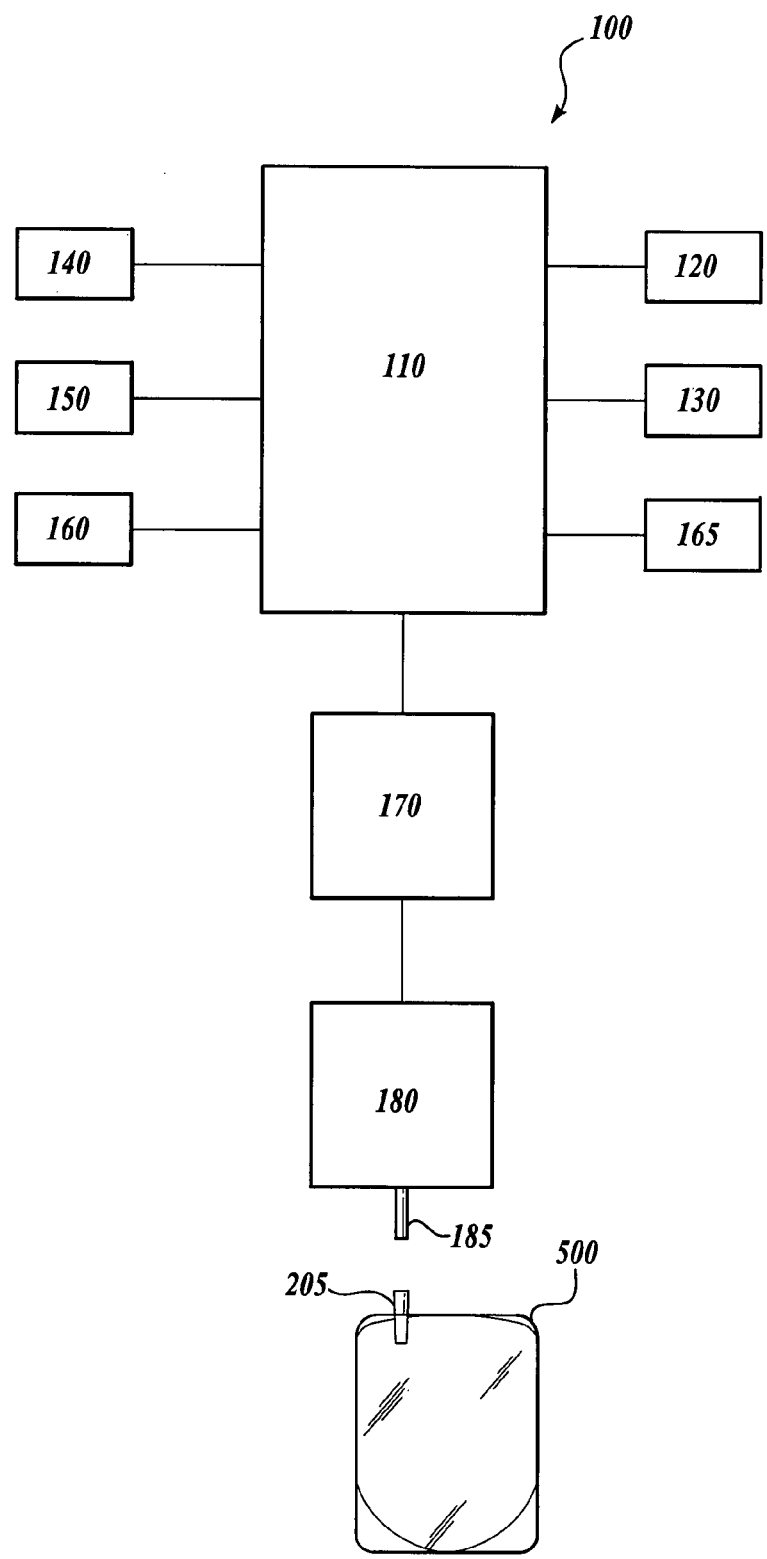
FIG. 18 is a schematic illustration of a representative system of the invention for measuring pH.

A representative system for carrying out the method of the invention is illustrated schematically in FIG. 18. Referring to FIG. 18, system 100 includes controller 110 that controls and operates the system components. System components include keypad 120 for inputting information including system commands; display 130 for determining the status of the system and viewing pH determination results; barcode reader 140 for inputting information to the system including the identification of the sample, the pH of which is to be measured by the system; printer 150 for printing system status and pH determination results; battery (or wall plug and power adapter) 160 for powering the system; memory device 165 for storing test results and calibration data; signal processing electronics 170 for commanding the optical platform components and processing signals from the optical platform; and optical platform 180 including an excitation source, emission detectors, light guides, and associated lenses and filters. Optical platform includes probe 185 housing one or more excitation light guides and two or more emission light guides. FIG. 19A also illustrates sealed vessel 500 including port 205 for receiving probe 185.

Figure 19:
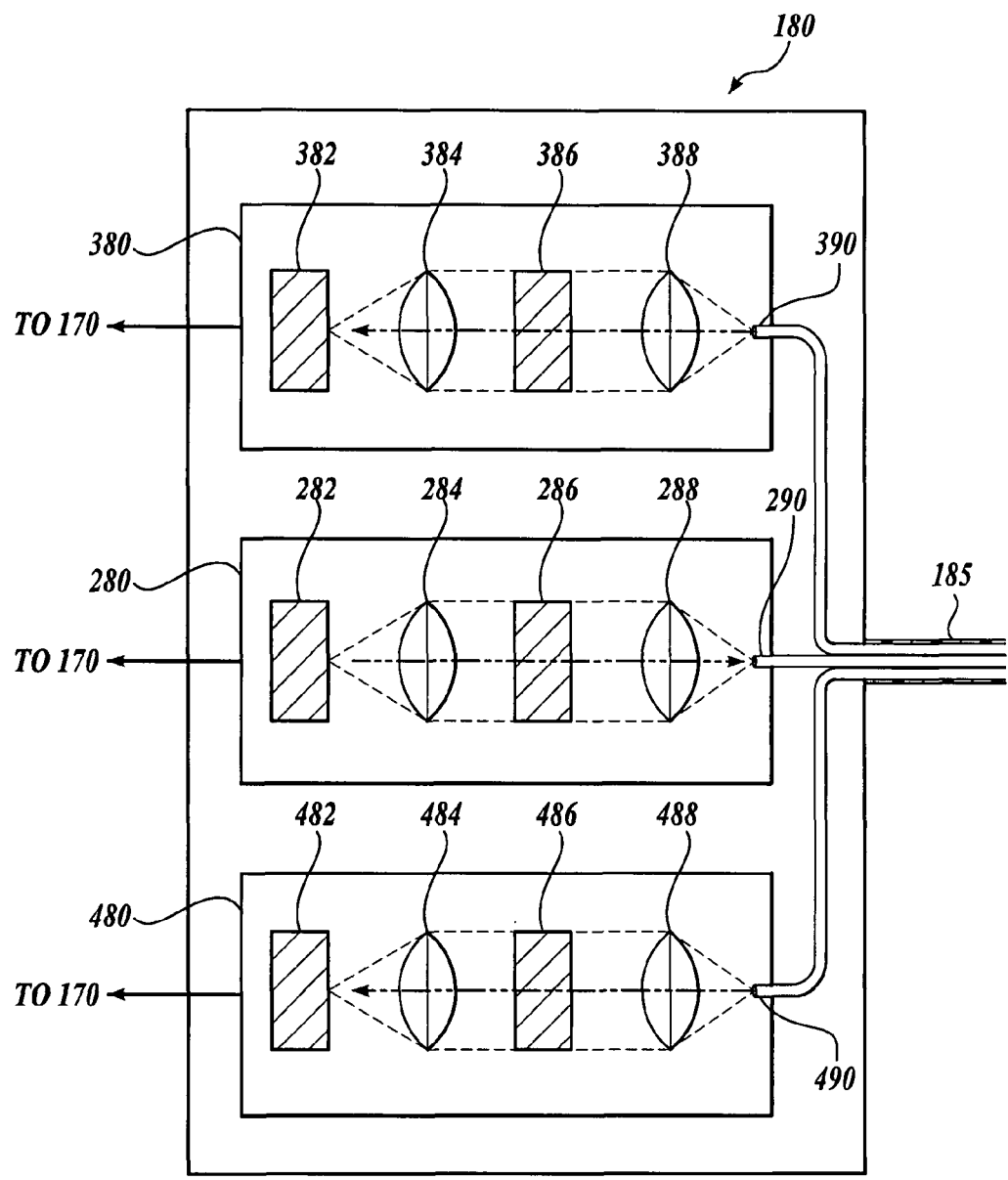
FIG. 19 is a schematic illustration of an optical platform useful in the system of the invention for measuring pH.

FIG. 19 is a schematic illustration of an optical platform useful in the system of the invention for measuring pH. Referring to FIG. 19, optical platform 180 includes excitation optics 280, first emission optics 380, and second emission optics 480. Excitation optics 280 include light source 282, collimating lens 284, filter 286, focusing lens 288, and excitation light waveguide 290. First emission optics 380 include detector 382, focusing lens 384, filter 386, collimating lens 388, and first emission light waveguide 390. Second emission optics 480 includes detector 482, focusing lens 484, filter 486, collimating lens 488, and second emission light waveguide 490. Excitation light guide 290, first emission light waveguide 390, and second emission light waveguide 490 are housed in probe 185.

The system's light source is effective in exciting the fluorescent species. Suitable light sources include light-emitting diodes, lasers, tungsten lamps, halogen lamps, xenon lamps, arc lamps, and hollow cathode lamps. In one embodiment, the light source is a light-emitting diode emitting light in the range from 500 to 560 nm. A representative light-emitting diode useful in the system of the invention is a green ultrabright Cotco 503 series LED commercially available from Marktech, Latham N.Y.

The collimating lens directs light (e.g., excitation light from the light source or first and second emission light from the emission light waveguides) to the bandpass filter. Suitable collimating lenses include Biconvex glass lenses and Plano-convex glass lenses. Representative collimating lenses useful in the system of the invention are the Tech Spec PCX lenses commercially available from Edmund Optics, Barrington, N.J. The excitation collimating lens is 12×36 (diameter by effective focal length in mm) and the first and second emission collimating lenses are 12×18.

The focusing lens focuses light from the bandpass filter to the excitation light waveguide or from the bandpass filter to the detector. Suitable focusing lenses include Biconvex glass lenses and Plano-convex glass lenses. Representative focusing lenses useful in the system of the invention are the Tech Spec PCX lenses commercially available from Edmund Optics, Barrington, N.J. The excitation focusing lens is 12×18 and the first and second emission focusing lenses are 12×15.

Filters are used in the optical platform to narrow the bandwidth of transmitted light.

Suitable excitation filters include bandpass filters, shortpass filters, longpass filters, or a combination of short and long pass filters. In one embodiment, the system uses a shortpass filter that passes light in the range from about 370 nm to 540 nm. A representative excitation shortpass filter useful in the system of the invention is 540ASP commercially available from Omega Optical, Brattleboro, Vt.

Suitable first emission filters include bandpass, shortpass, longpass, or a combination of short and longpass filters. In one embodiment, the bandpass filter passes light in the range from about 595 to 605 nm and has a full width at half height of 10 nm. A representative first emission bandpass filter useful in the system of the invention is 600DF10 commercially available from Omega Optical, Brattleboro, Vt.

Suitable second emission filters include bandpass, shortpass, longpass, or a combination of short and longpass filters. In one embodiment, the bandpass filter passes light in the range from about 562 to 573 nm and has a full width at half height of 10 nm. A representative second emission bandpass filter useful in the system of the invention is 568DF10 commercially available from Omega Optical, Brattleboro, Vt.

The excitation light waveguide transmits excitation light from the light source through the probe to the fluorescent species. In one embodiment, the excitation light waveguide includes one or more optical fibers. In one embodiment, the excitation waveguide is a single optical fiber. A representative fiber optic useful in the system of invention is RO2-534 commercially available from Edmund Optics, Barrington, N.J.

The first and second emission light waveguides transmit fluorescent emission from the fluorescent species through the probe to the first and second emission detectors, respectively.

In one embodiment, the first emission light waveguide includes one or more optical fibers. In one embodiment, the first emission light waveguide includes a plurality of optical fibers. In one embodiment, the first emission light waveguide includes four optical fibers. A representative fiber optic useful in the system of invention is RO2-533 commercially available from Edmund Optics, Barrington, N.J.

In one embodiment, the second emission light waveguide includes one or more optical fibers. In one embodiment, the second emission light waveguide includes a plurality of optical fibers. In one embodiment, the second emission light waveguide includes four optical fibers. A representative fiber optic useful in the system of invention is RO2-533 commercially available from Edmund Optics, Barrington, N.J.

Suitable optical fibers useful in the system of the invention include glass or plastic optical fibers from 0.2 to 2 mm diameter.

The system's first and second emission detectors are effective in measuring the first and second fluorescent emissions from the fluorescent species. Suitable detectors include photodiodes, PIN diodes, and photomultiplier tubes. In one embodiment, the first and second emission detectors are photodiodes responsive in the range from 400 to 800 nm. Representative photodiodes useful in the system of the invention include BPW34 commercially available from Vishay Intertechnology, Malvern, Pa.

A representative probe housing excitation and emission light guides useful in the system of the invention is illustrated schematically in FIG. 20. As shown in FIG. 20, the light guides are optical fibers. Referring to FIG. 20, probe 185 houses excitation light guide 290, a plurality of first emission light guides 390, and a plurality of second emission light guides 490. In the representative probe shown in FIG. 20, there are four first emission light guides 390, and four second emission light guides 490. The four first emission light guides can be considered to be a first channel (e.g., measuring the first fluorescent emission from the fluorescent species) and the four second emission light guides can be considered to be a second channel (e.g., measuring the second fluorescent emission from the fluorescent species). In the illustrated representative probe, the fibers from each of the two sets of fibers alternate (i.e., alternating fibers 390 and 490) around the central fiber (290). This configuration provides for evening out of "hot spots" so that light collected by the first set is similar to the light collected by the second set.

The relationship between the probe housing the excitation/emission light guides and the sealed vessel port is illustrated schematically in FIG. 21. Referring to FIG. 21, probe 185 is received by port 205. Port 205 includes window 210, which is transparent to excitation and emission wavelengths used in the fluorescent measurement. Excitation light emanating from light guide 290 passes through window 210 and interrogates substrate 220 on which the fluorescent species is immobilized and which, in the operation of the method of the invention, is in contact with the sample contained in sealed vessel 200. Irradiation of substrate 220 results in excitation of the substrate-immobilized fluorescent species and fluorescent emission from the fluorescent species. Emission from the fluorescent species is received by and transmitted through light guides 390 and 490 to detectors 382 and 482, respectively (see FIG. 19B). As noted above, the fluorescent species' first emission intensity and the second emission intensity will depend on the pH of the sample.

Figure 22:
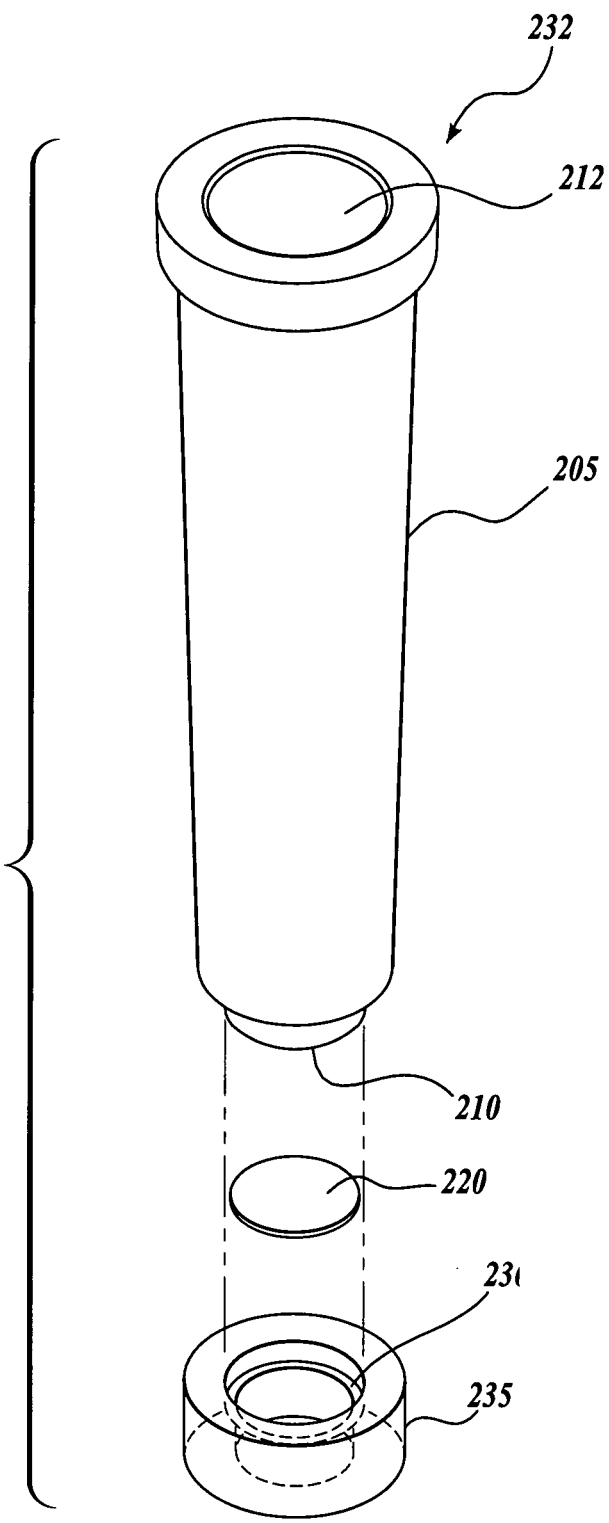
FIG. 22 is a representative port assembly useful in the manufacture of a sealed vessel.

A representative port assembly useful for incorporation into a sealed vessel during manufacture is illustrated in FIG. 22. Referring to FIG. 22, port assembly 232 includes port 205 and tip 235. Port 205 is a cylinder terminating with window 210 and having opening 212 for receiving probe 185 (not shown). In one embodiment, port 205 tapers from opening 212 to window 210 such that the depth of insertion of probe 185 into port 205 is predetermined by the probe's diameter. When inserted in the port, the face of probe 185 and window 210 are substantially parallel. Port 205 and tip 235 are adapted such that the port and tip are reversibly connectable. In one embodiment, port 205 includes annular inset 214 and tip 235 includes opening 216 defined by annular lip 218 for receiving inset 214. In this embodiment, inset 214 has a diameter less than opening 216. It will be appreciated that the connecting relationship between the port and tip can be reversed (i.e., port having annular lip for receiving tip having inset). Lip 218 defines bed 222 for receiving substrate 220, which is secured in port assembly 202 when port 205 is connected to tip 235. Tip 235 includes aperture 224 in bed 222. Aperture 224 provides for contact of substrate 220 with a liquid sample contained in the sealed vessel.

Fluorescent Species Having pH-Dependent Emission.

In one embodiment, the method and system of the invention for measuring pH uses a fluorescent species having pH-dependent fluorescent emission. The fluorescent species has a first emission intensity at a first wavelength and a second emission intensity at a second wavelength, the first and second emission intensities being characteristic of pH in the environment of the fluorescent species. The ratio of the first and second emission intensities provides pH measurement. It is appreciated that fluorescent emission occurs as a wavelength band having a band maximum that is referred to herein as the emission wavelength.

In one embodiment, the separation between the first wavelength and the second wavelength is at least about 40 nm. In one embodiment, the separation between the first wavelength and the second wavelength is at least about 30 nm. In one embodiment, the separation between the first wavelength and the second wavelength is at least about 20 nm. Using 10 nm HBW filters, the separation is at least about 30 nm. Preferably, the system of the invention achieves fluorescence signal separation by removing any emission band overlap by 10E5 or more.

The method and system of the invention for measuring pH are not limited to any particular fluorescent species, nor any particular pH range. The method and system of the invention is operable with any fluorescent species having pH-dependent properties that can be excited and its emission measured. The range of pH measurable by the method and system of the invention can be selected and is determined by the pH-dependent properties of the fluorescent species.

In addition to their pH-dependent properties noted above, suitable fluorescent species include those that can be substantially irreversibly immobilized on a substrate. The fluorescent species can be covalently coupled to the substrate or non-covalently associated with the substrate.

Suitable pH-dependent fluorescent species include those known in the art. Representative fluorescent species having suitable pH-dependent properties include fluorescein derivatives including naphthofluorescein compounds, seminaphthofluorescein compounds (e.g., SNAFL compounds), and seminaphthorhodafluor compounds (e.g., SNARF compounds). These compounds have advantages associated with their long wavelength emission, which is less susceptible to potential interfering light absorbing substances in blood. These compounds also have relatively long wavelength absorbance making them particularly suitable for excitation by commercially available LED light sources. Another compound having suitable pH dependent behavior is HPTS, 8-hydroxy-1,3,6-pyrenetrisulfonic acid. Although the compound has desired ratiometric pH properties, excitation is optimal at short wavelength (403 nm) where strong LED light sources are not commercially available. Representative SNAFL and SNARF compounds useful in the method and system of the invention are described in U.S. Pat. No. 4,945,171. Molecular Probes (now Invitrogen, Eugene, Oreg.) sells CNF, SNAFL, SNARF fluors with conjugatable carboxylic acid linker groups, see, for example, Molecular Probes Handbook (Ninth Edition) by R. P. Haugland, Chapter 21 "pH indicators" pages 829-847. Epoch Biosciences (now Nanogen, Bothell, Wash.) sells EBIO-3 with a propanoic acid linker. Whitaker et al. (Anal. Biochem. (1991) 194, 330-344) showed the synthesis of a number of SNAFL compounds. Wolfbeis et al. (Mikrochim Acta (1992) 108, 133-141) described the use of CNF and aminocellulose conjugates. The earliest reference to the SNAFL family of compounds is Whitaker et al. (1988) Biophys. J. 53, 197a. A related dye in the CNF family is VITA-BLUE, a sulfonenaphthofluorescein derivative (Lee et al. (1989) Cytometry 10, 151-164) having a pKa of 7.56. A CNF analog with bromine substituents at each carbon adjacent to a phenol (pKa 7.45) has a pKa that is 0.54 pKa units lower than their measured pKa for CNF (pKa 7.99). Lee et al. note that "true" pKa values are difficult to determine for these compounds. A method for pKa determination is described in Example 12. SNAFL-1 (literature pKa ~7.8) free acid had a pKa of 7.6 in that fluorescence-based assay. Other suitable fluorescent species include the compounds described in U.S. Patent Application Publication No. US 2006/0204990 A1, published Sep. 14, 2006 (Ser. No. 11/357,750).

The structures of seminaphthofluorescein compounds (SNAFL-1 and EBIO-3) useful in one embodiment of the method and system of the invention are illustrated below.

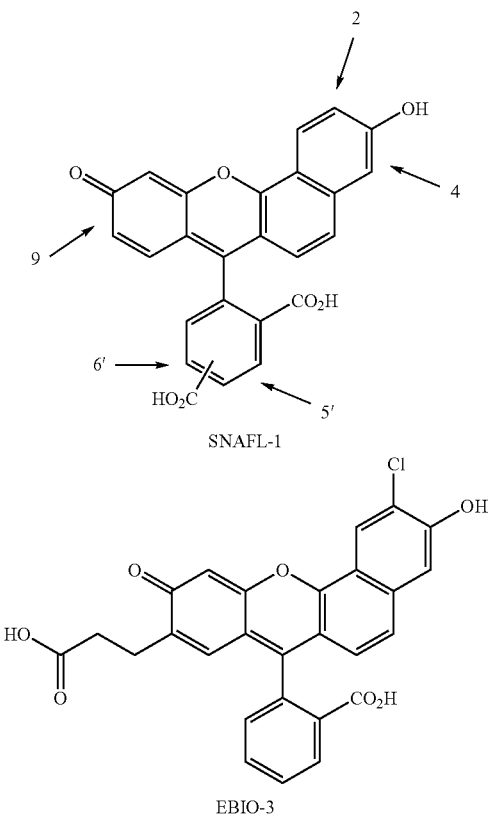

SNAFL-1

EBIO-3

The numbering scheme describes position of attachment of linker molecules. These compounds have carboxylate linking groups suitable for conjugation to carrier proteins, as described below. For conjugation, the reactive N-hydroxysuccinimide (NHS) ester of SNAFL-1 (commercially available from Molecule Probes, Inc., Eugene, Oreg.) can be used. Conjugation to lysine residues in human serum albumin (HSA) gave desired SNAFL/HSA conjugates. Carbodiimide activation of EBIO-3 gave a reactive intermediate that was efficiently conjugated to human serum albumin.

Representative seminaphthofluorescein compounds useful in a method and system of the invention are illustrated in FIGS. 23A-23E.

The SNAFL compounds are commercially available from Molecular Probes, Inc., Eugene, Oreg. The SNAFL compounds can be readily synthesized according to general procedures that have been published (see, for example, U.S. Pat. No. 4,945,171).

The preparation of a representative 2-chloro substituted SNAFL compound is shown below.

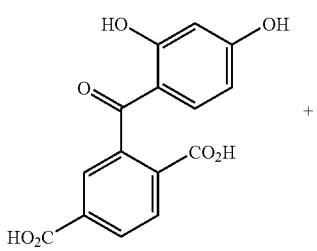

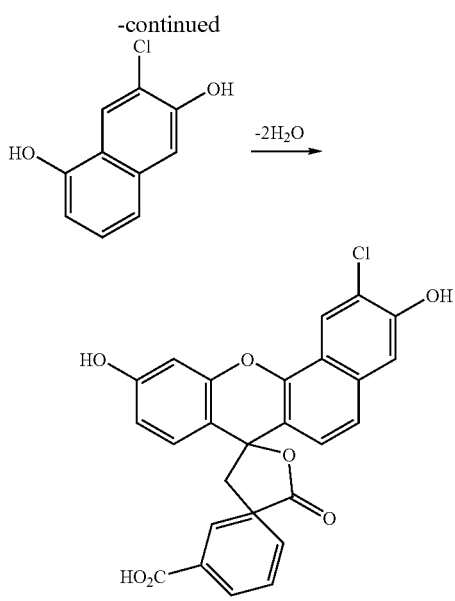

The compound can be prepared by condensation of 1,6-dihydroxynaphthalene with the diacid substituted 4-acylresorcinol in the presence of a dehydrating acid or Lewis acid catalyst, such as zinc chloride.

The preparation of SNAFL compounds having propionic acid linkers is described in U.S. patent application Ser. No. 11/022,039, incorporated herein by reference in its entirety. A representative SNAFL compounds having a propionic acid linker, EBIO-3, is commercially available from Nanogen, Bothell Wash.

Figure 24:
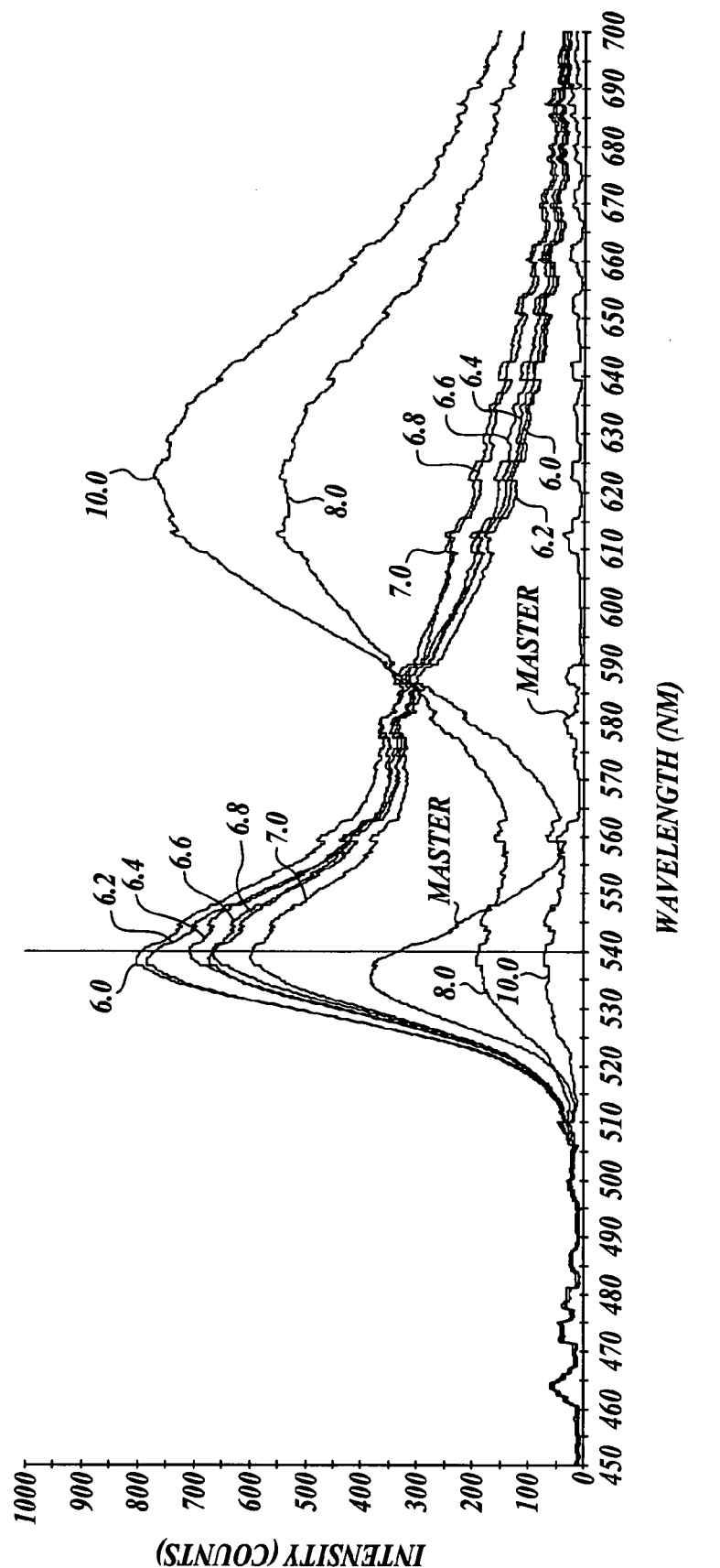
FIG. 24 illustrates the emission spectra as a function of pH of a representative fluorescent species (SNAFL-1) useful in the method and system of the invention.
Figure 25:
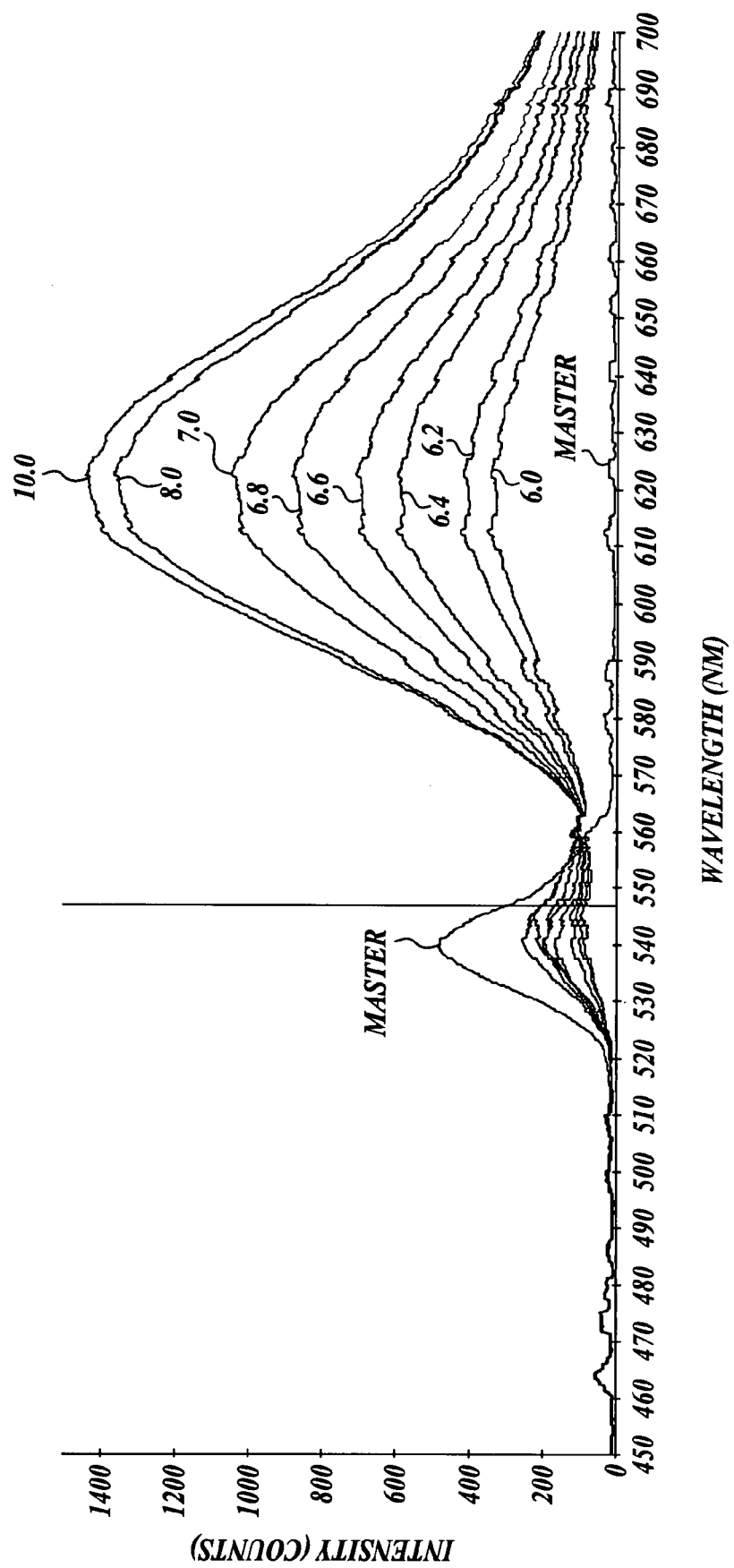
FIG. 25 illustrates the emission spectra as a function of pH of a representative fluorescent species (EBIO-3) useful in the method and system of the invention.

The emission spectra as a function of pH of representative fluorescent species (i.e., SNAFL-1 and EBIO-1) useful in the method and system of the invention are illustrated in FIGS. 24 and 25, respectively. FIG. 24 illustrates the emission spectra of SNAFL-1 in 50 mM potassium phosphate buffer as a function of pH (pH 6.0 to 10.0) (excitation at 540 nm). Referring to FIG. 24, the response at pH 6-7 is relatively poor (pKa=7.6). FIG. 25 illustrates the emission spectra of EBIO-3 in 50 mM potassium phosphate buffer as a function of pH (pH 6.0 to 10.0) (excitation at 545 nm). Referring to FIG. 25, the response at pH 6-7 is relatively good (pKa=6.6). Spectral properties and pKa data for the SNAFL analogs illustrated in FIGS. 23A-23E are summarized in Table 1.

TABLE 1 pH-Sensitive absorbance and emission of SNAFL analogs.

| Compound | Absorbance λmax (acid) | Absorbance λmax (base) | Emission λiso | Emission λmax (base) | pKa |
|---|---|---|---|---|---|
| SNAFL-1 | 482, 510 nm | 540 nm | 585 nm | 620 nm | 7.6 |
| SNAFL-2 | 485, 514 | 547 | 590 | 630 | 7.6 |
| EBIO-1 | 496, 519 | 545 | 560 | 620 | 6.5 |
| EBIO-2 | 506, 538 | 572 | 590 | 645 | 7.8 |
| EBIO-3 | 480, 509 | 534 | 560 | 610 | 6.6 |

Referring to Table 1, absorbance and emission spectra were obtained at 10 μM SNAFL analog. Absorbance was measured at pH 6, 8, and 10: acid (pH 6) gave two bands of similar absorbance; pH 10 gave a single λmax (base). The emission spectra were determined by excitation at the absorbance λmax (base). The wavelength where emission spectra crossed is reported as λiso. The emission λmax was measured at pH 10. pKa was determined from fluorescence emission spectra. EBIO-1 and EBIO-3 were more sensitive to changes at pH ~6.5. The other analogs were more sensitive at pH ~8.

Fluorescent Species Conjugates for Substrate Immobilization.

For use in a method and system of the invention, the fluorescent species may be immobilized on a substrate such that the fluorescent species is in contact with the sample, the pH of which is to be measured. The fluorescent species can be immobilized on the substrate through the use of a material (e.g., macromolecular spacer material) having a strong associative interaction with the substrate. The spacer material allows covalent conjugation of the fluorescent species and provides large surface area needed for efficient non-covalent immobilization to the substrate surface. In one embodiment, the spacer material is human serum albumin (HSA) having ~44 lysine residues available for covalent conjugation. HSA's densely charged molecular structure has a passivating effect when adsorbed to biomaterials. Other advantages include reduced fluorescence quenching, uniform environment for the conjugated fluorophore, and availability in recombinant form (from yeast) so there is no chance of infection (as with HSA from donors). HSA conjugates are easily purified by ultrafiltration methods and form stable solutions that are easily characterized by absorbance and fluorescence assays to determine the number of fluorophores per protein.

In one embodiment, the fluorescent species is immobilized on the substrate through the use of a protein or protein fragment. Suitable proteins include those that can be substantially irreversibly immobilized on the substrate. The protein can be covalently coupled to the substrate or non-covalently associated with the substrate. Suitable proteins include proteins to which the fluorescent species can be substantially irreversibly immobilized. The fluorescent species can be covalently or non-covalently associated with the protein.

Suitable proteins include human serum albumin (HSA), bovine serum albumin (BSA), von Willebrand's factor, kininogen, fibrinogen, and hemoglobin (no iron). Suitable proteins include proteins having available lysine residues (for conjugation to the fluorophore) and molecular weight sufficient to allow for immobilization efficiency to the blot membrane. Other functional groups in the protein (like cysteine) could presumably be used for covalent bonding to suitably reactive solid supports.

In one embodiment, the fluorescent species is immobilized on the substrate through the use of a polysaccharide. Suitable polysaccharides include those that can be substantially irreversibly immobilized on the substrate. The polysaccharide can be covalently coupled to the substrate or non-covalently associated with the substrate. Suitable polysaccharides include proteins to which the fluorescent species can be substantially irreversibly immobilized. The fluorescent species can be covalently or non-covalently associated with the polysaccharide.

Suitable polysaccharides include dextrans, aminodextrans, heparin, and lectins.

In another embodiment, the fluorescent species is immobilized on the substrate through the use of dendrimeric structures. Suitable dendrimeric structures include those that can be substantially irreversibly immobilized on the substrate. The dendrimeric structures can be covalently coupled to the substrate or non-covalently associated with the substrate. PAMAM dendrimers are commercially available as are other structural types and sizes.

In one embodiment, the fluorescent species is covalently coupled to a protein to provide a fluorophore-protein conjugate that can be immobilized on a substrate. In one embodiment, the fluorophore-polysaccharide conjugate is non-covalently associated with the substrate.

Figure 26:
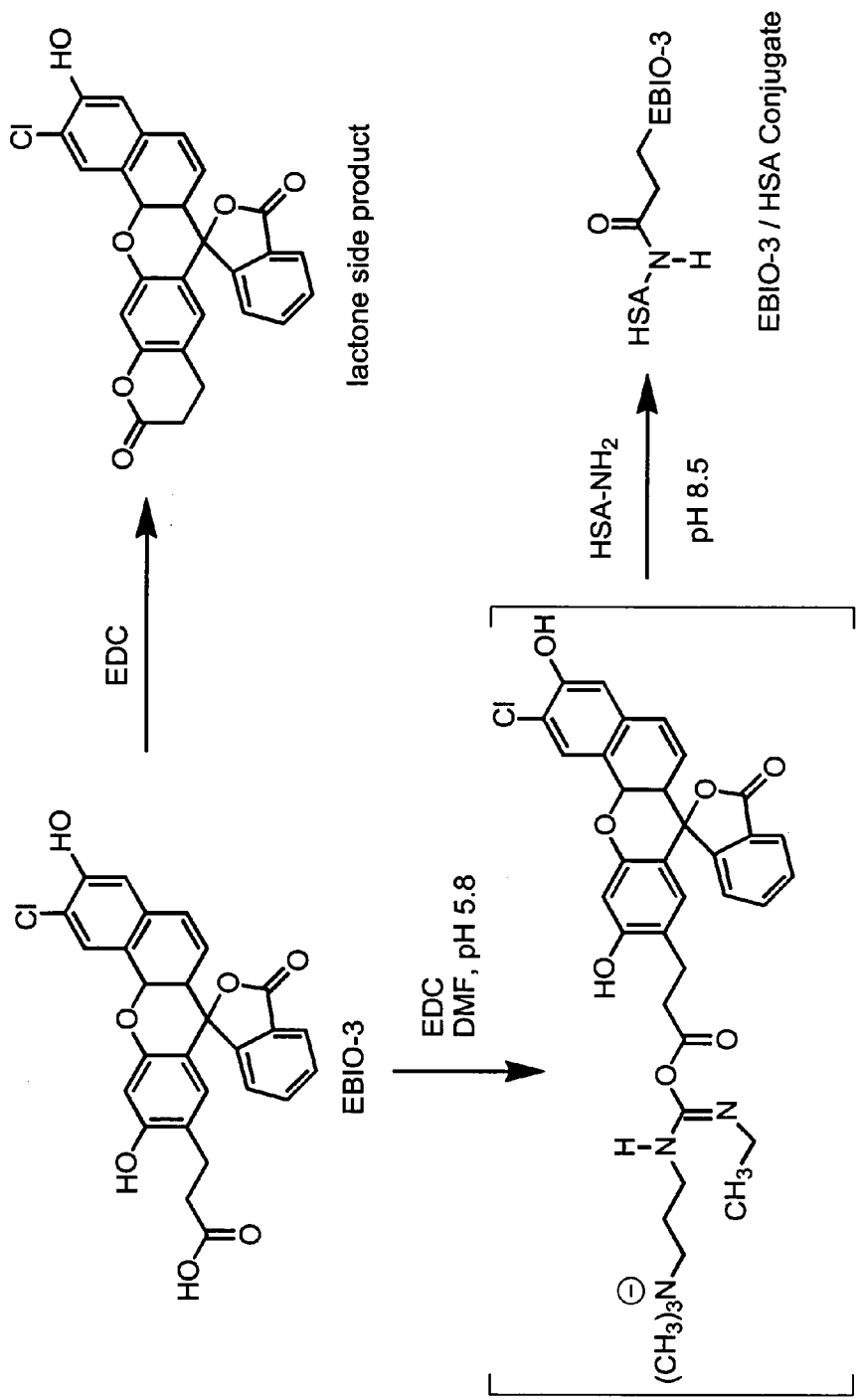
FIG. 26 is a schematic illustration of the preparation of a representative fluorophore-protein (EBIO-3/HSA) conjugate useful in the method and system of the invention.

In one embodiment, a fluorophore-protein conjugate is immobilized on a substrate. In one embodiment, the fluorescent species is a seminaphthofluorescein and the protein is human serum albumin. In one embodiment, the seminaphthofluorescein is SNAFL-1. The preparation of SNAFL-1/HSA conjugates is described in Example 13. The fluorescent properties of SNAFL-1/HSA conjugates are described in Example 14. In one embodiment, the seminaphthofluorescein is EBIO-3. The preparation of EBIO-3/HSA conjugates is described in Example 1. A schematic illustration of the coupling of EBIO-3 to HSA is illustrated in FIG. 26. The fluorescent properties of EBIO-3/HSA conjugates are described in Example 15.

Figure 27:
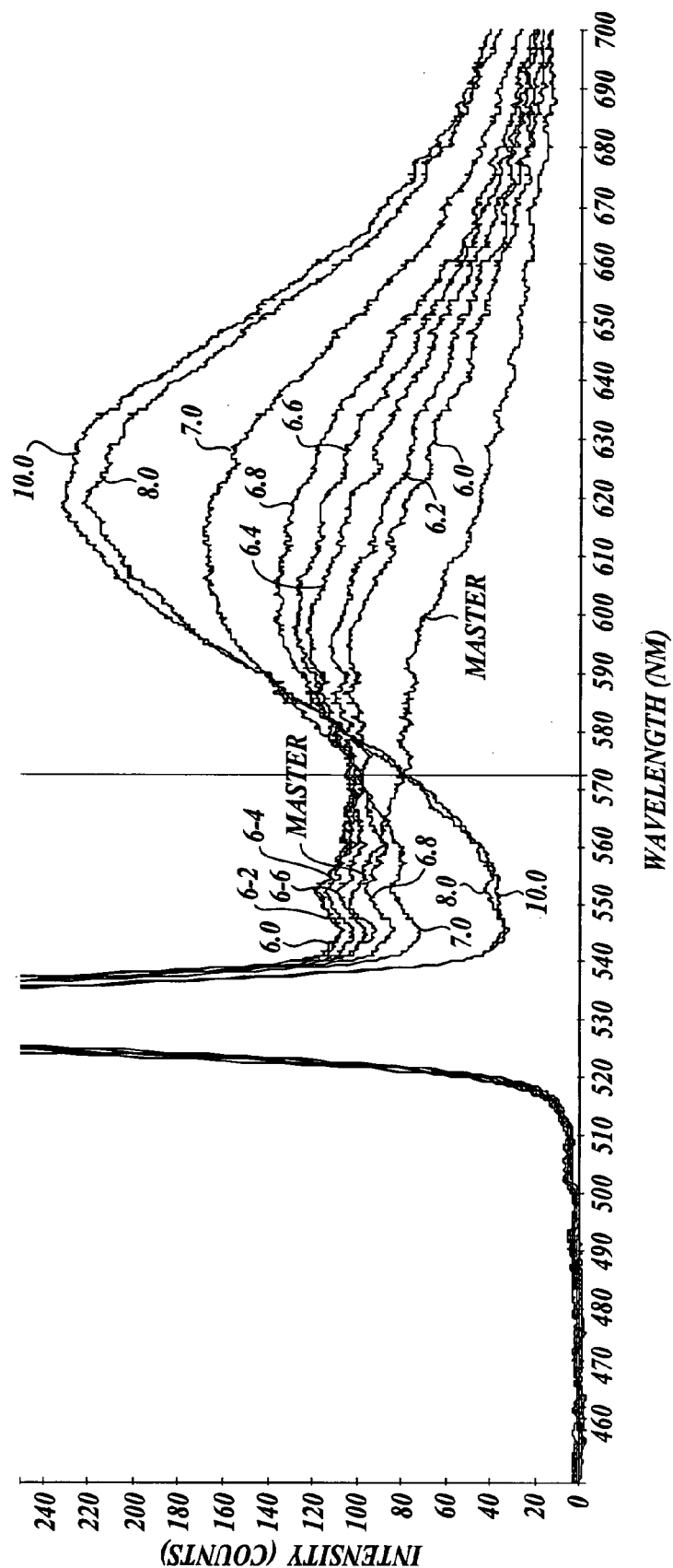
FIG. 27 illustrates the emission spectra as a function of pH of a representative fluorophore-protein conjugate (SNAFL-1/HSA) useful in the method and system of the invention.

The fluorescent emission spectra as a function of pH (6.0 to 10.0) of a representative fluorophore-protein conjugate (SNAFL-1/HSA, 1.6 fluorophores per HSA) useful in the method and system of the invention are illustrated in FIG. 27.

Figure 28:
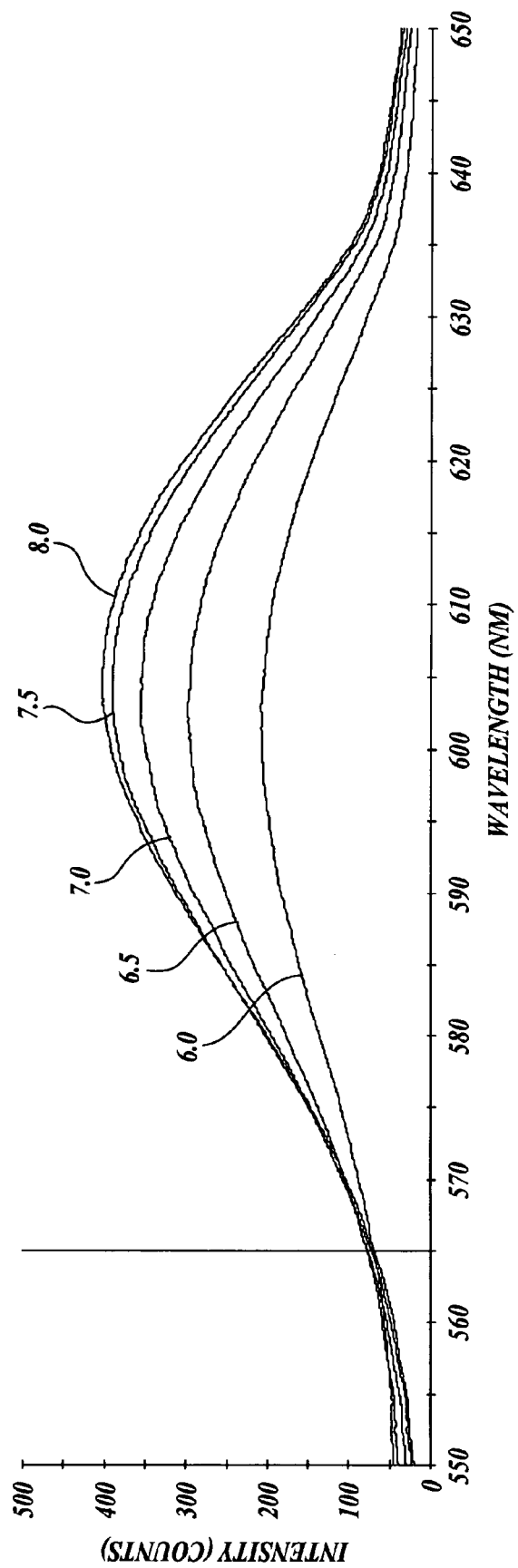
FIG. 28 illustrates the emission spectra as a function of pH of a representative fluorophore-protein conjugate (EBIO-3/HSA) useful in the method and system of the invention.

The fluorescent emission spectra as a function of pH (6.0 to 10.0) of a representative fluorophore-protein conjugate (EBIO-3/HSA, 1.92 fluorophores per HSA) useful in the method and system of the invention are illustrated in FIG. 28.

For the fluorophore-protein conjugate, the optimum fluorophore loading will vary depending on the particular fluorophore.

For SNAFL-1/HSA conjugates the fluorophore loading can vary from about 0.01 to about 38 SNAFL-1/HSA. Low signal at 0.01 and fluorescent quenching at 40 fluorophores/HSA. In one embodiment, the SNAFL-1 conjugate includes about 2 SNAFL-1/HSA.

For EBIO-3/HSA conjugates the fluorophore loading can vary from about 0.01 to about 40 EBIO-3/HSA. In one embodiment, the EBIO-3 conjugate includes about 2 EBIO-3/HSA.

Substrates for Fluorescent Species Immobilization.

In the method and system of the invention, the fluorescent species is immobilized on a substrate. As noted above, the fluorescent species can be directly immobilized on the substrate covalently or by non-covalent association or, alternatively, through the use of a material (e.g., fluorophore-protein conjugate) that can be immobilized on the substrate covalently or by non-covalent association.

Suitable substrates substantially irreversible immobilized the fluorescent species. In the method of the invention, suitable substrates also do not inhibit the contact of the liquid sample with the fluorescent species and do not impair or alter the pH measurement.

Figure 38:
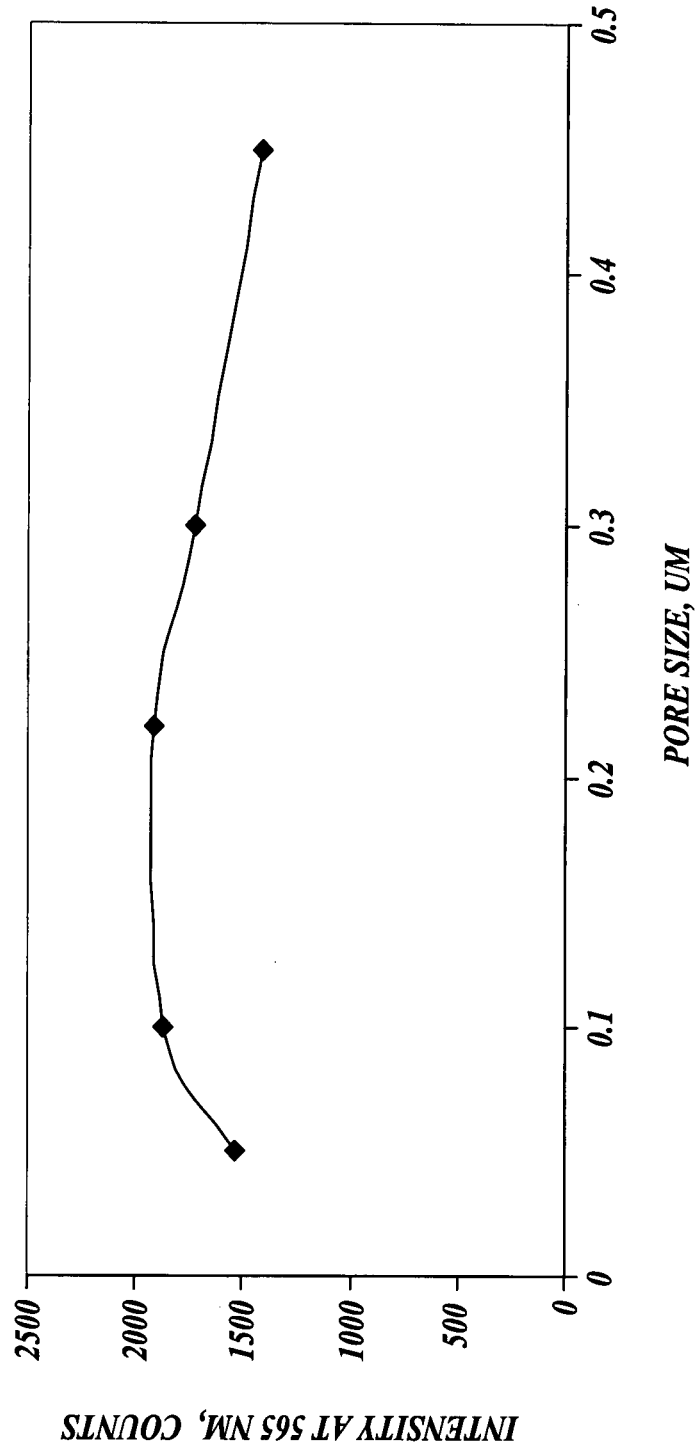
FIG. 38 illustrates the effect of membrane pore size on fluorescent intensity in measuring pH in accordance with the invention.

Representative substrates include membranes, such as microporous membranes made of cellulose, nitrocellulose, mixed esters of nitrocellulose and cellulose acetate, polyethylene terephthalate, polycarbonate, polyvinylidene fluoride and polyimide. Such materials are available commercially from Whatman S&S, Florham Park, N.J. and Millipore, Billerica Mass. Suitable membranes include membranes in which the microporous structure is created by ion beam penetration such as membranes commercially available from Oxyphen Gmbh, Dresden, Germany under the designation OXYPHEN. Charged nylon surfaces (Nytran) can also be used. Suitable membranes include plastic membranes in which the microporous structure is made by injection molding the micropores into the plastic such as the processes used by Åmic, Stockholm, Sweden. Emission intensity of SNAFL-1/HSA at pH 7 immobilized on various pore size mixed ester nitrocellulose cellulose acetate membranes is shown in FIG. 38.

Immobilization of representative fluorophore protein conjugates on membranes is described in Examples 16 and 2. Example 16 describes the immobilization of SNAFL-1/HSA conjugates. Example 17 describes the fluorescent properties of immobilized SNAFL-1/HSA conjugates. Example 2 describes the immobilization of EBIO-3/HSA conjugates. Example 18 describes the fluorescent properties of immobilized EBIO-3/HSA conjugates.

Figure 29:
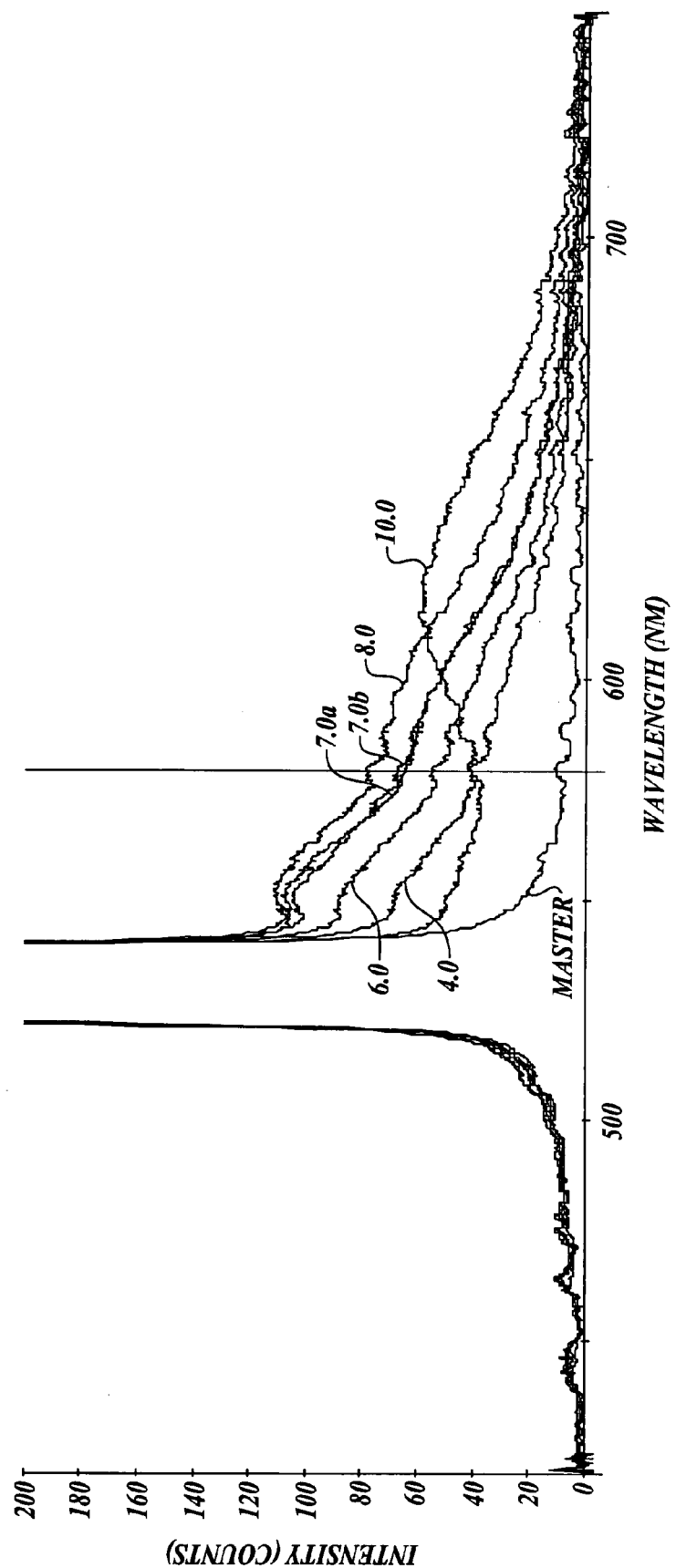
FIG. 29 illustrates the emission spectra of a representative substrate-immobilized fluorophore-protein conjugate (SNAFL-1/HSA) as a function of pH (Oxyphen)
Figure 30:
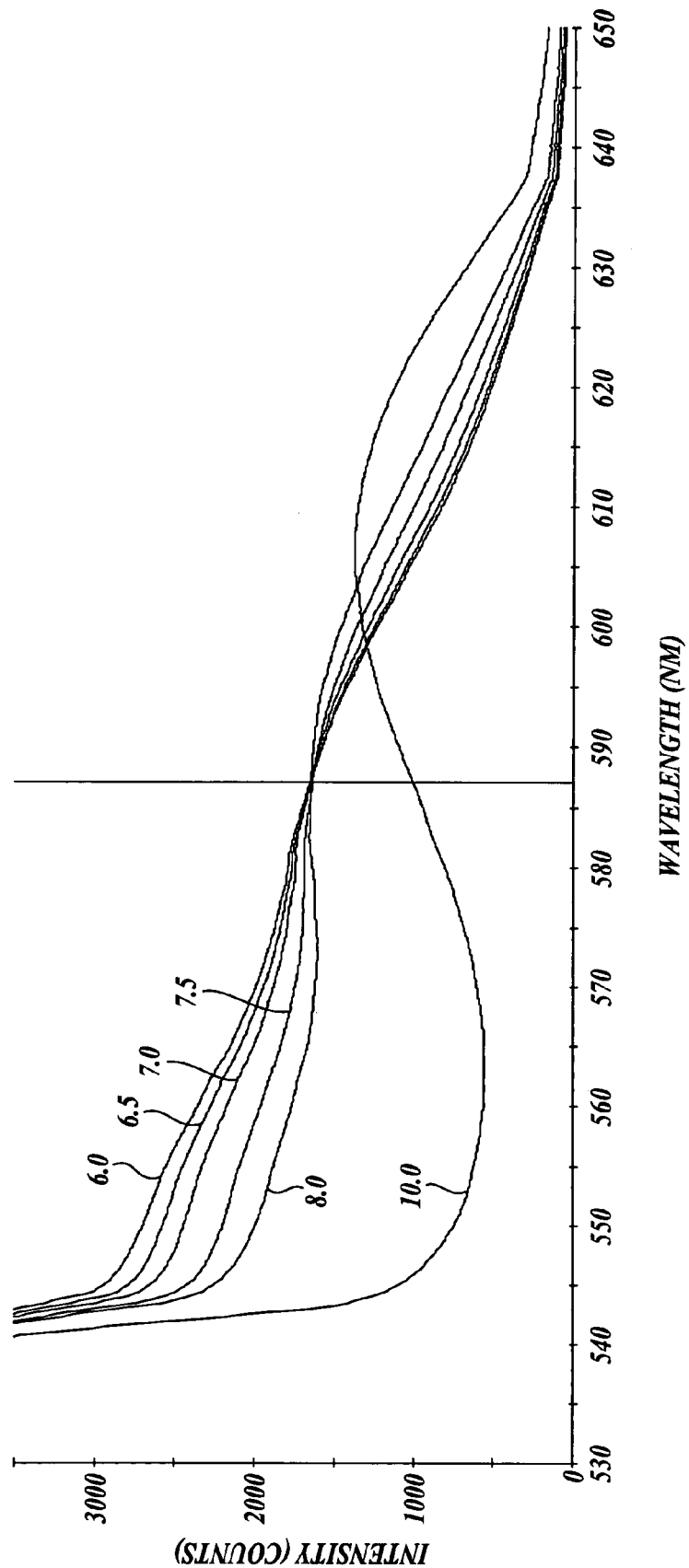
FIG. 30 illustrates the emission spectra of a representative substrate-immobilized fluorophore-protein conjugate (SNAFL-1/HSA) as a function of pH (nitrocellulose)

The emission spectra of a representative fluorophore-protein conjugate (SNAFL-1/HSA, 3.6:1) immobilized on Oxyphen and nitrocellulose as a function of pH (pH response), as measured by the microwell assay described in Example 17, are illustrated in FIGS. 29 and 30, respectively.

Figure 31:
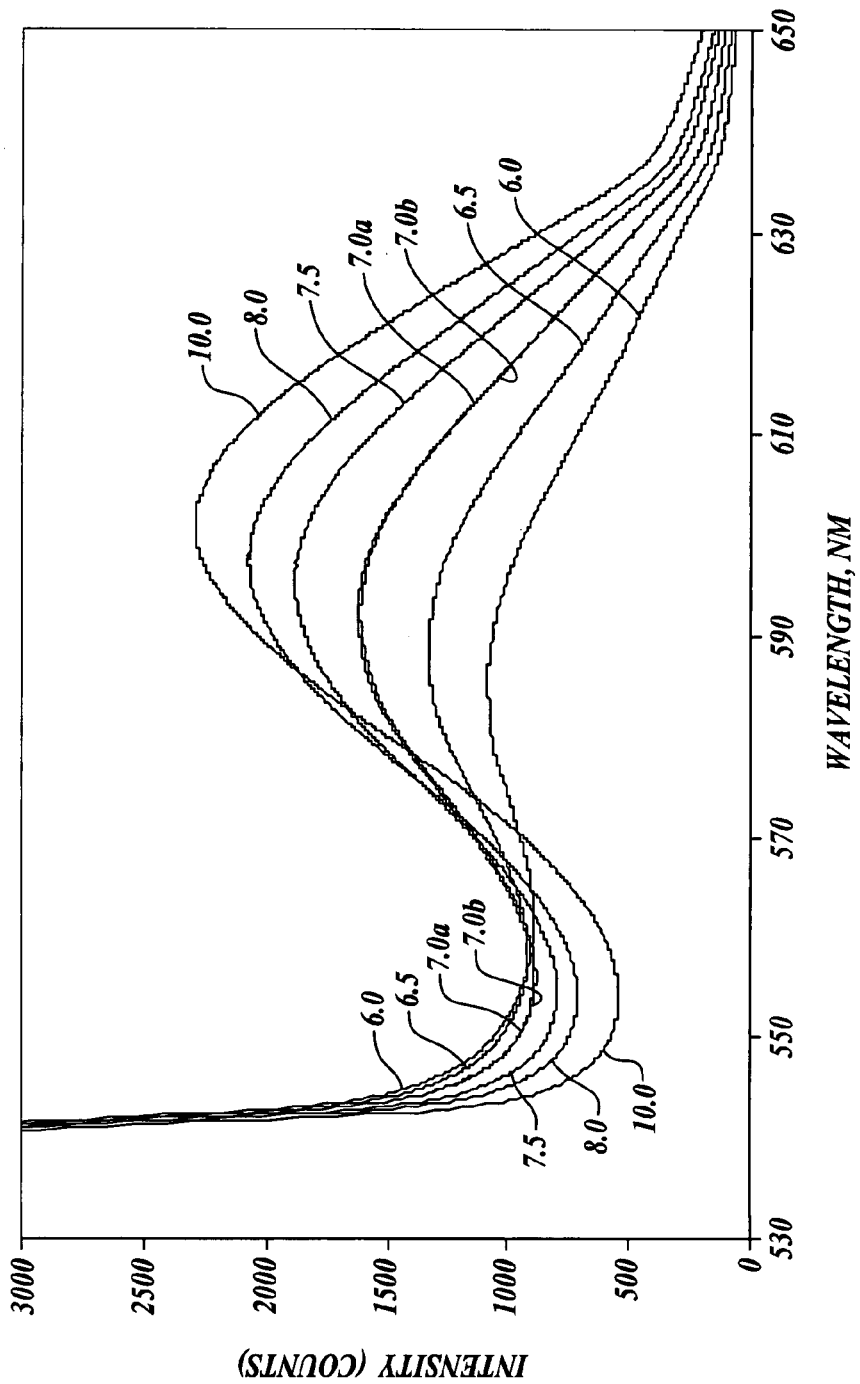
FIG. 31 illustrates the emission spectra of a representative substrate-immobilized fluorophore-protein conjugate (EBIO-3/HSA) as a function of pH (nitrocellulose)

The emission spectra of a representative fluorophore-protein conjugate (EBIO-3/HSA, 2.0:1) immobilized on nitrocellulose, as described in Example 16, as a function of pH (6.0, 6.5, 7.0, 7.5, 8.0, and 10.0), as measured by the telescoping tube insert assay described in Example 18, are illustrated in FIG. 31. The large spread of emissions at 600 nm for the pH 6 to 8 range indicates good fluorescence verses pH response.

Ratiometric pH Method and System.

In one embodiment, the method of the invention is a fluorescent wavelength-ratiometric method. In the method, the first and second fluorescent emission intensities of the fluorescent species measured at first and second emission wavelengths, respectively, are ratioed to provide pH information. The first emission wavelength varies with pH while the second emission wavelength is constant with pH and gives an internal control for the fluorescent intensity. In one embodiment, a lookup table is used to lookup a combination of the measured ratio, first and second emission wavelength and determines its corresponding pH. In one embodiment, a mathematical function of the ratio, first and second emission wavelength is used to calculate the resulting pH. FIG. 15 is a lookup table that correlates the ratio of the two emission intensities to pH. FIG. 16 is an example of data from calibration studies that are used to generate a lookup table such as the one in FIG. 15.

Figure 32:
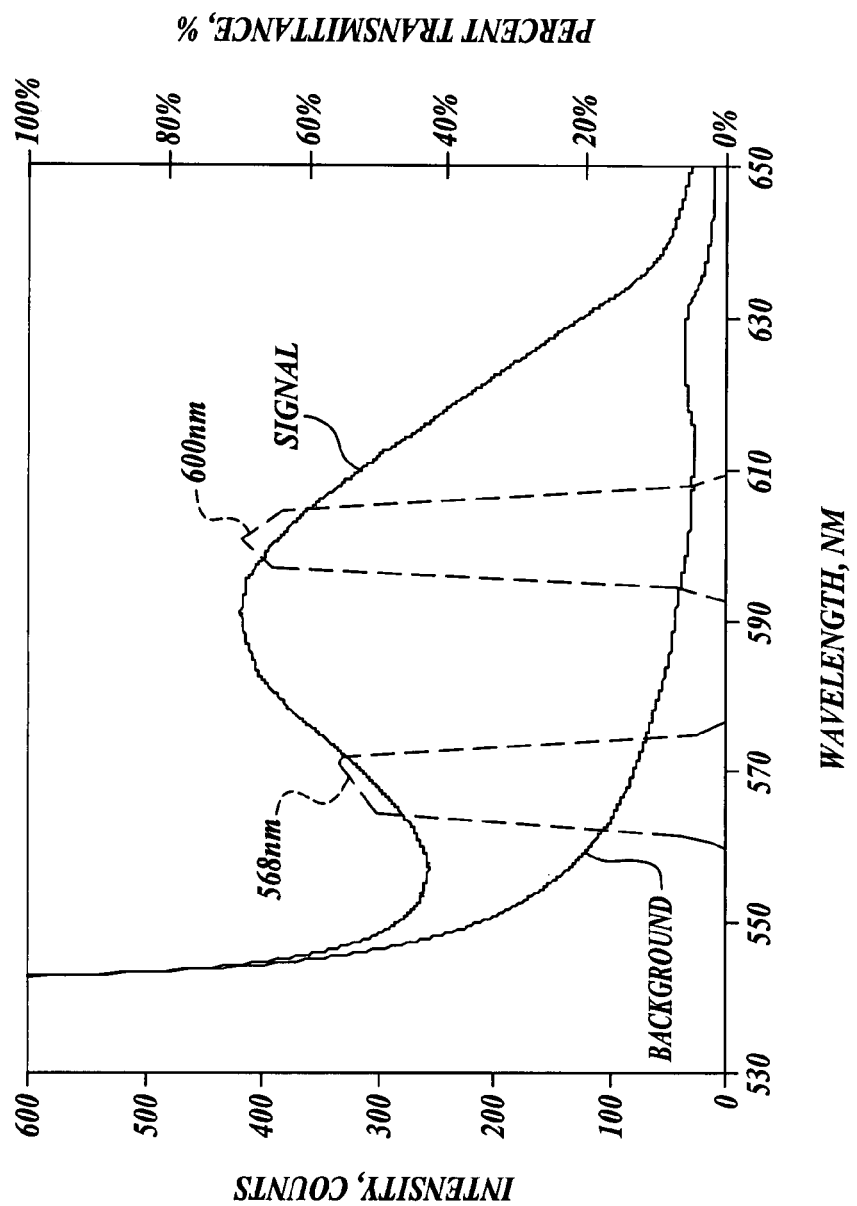
FIG. 32 illustrates the data used in the method of the invention for measuring pH.

FIG. 32 illustrates the data used in the method of the invention for measuring pH. The emission spectra of a representative fluorophore-protein conjugate (EBIO-3/HSA, 2:1) immobilized on nitrocellulose at pH 7.0 is shown as measured by the telescoping tubing insert assay. In this setup, the excitation bandpass filter was unable to completely remove the excitation light in the emission region as illustrated by the background signal measured on a blank nitrocellulose disc. The full spectrum corrected for the background was multiplied by the transmittance of the first and second hypothetical filters at each wavelength and the area under the resultant curve was calculated to give a signal for the first and second wavelength. The center wavelengths and bandwidths of hypothetical filters were chosen such that the ratiometric properties of the conjugate had the strongest relationship to the pH in the region of interest.

Figure 33:
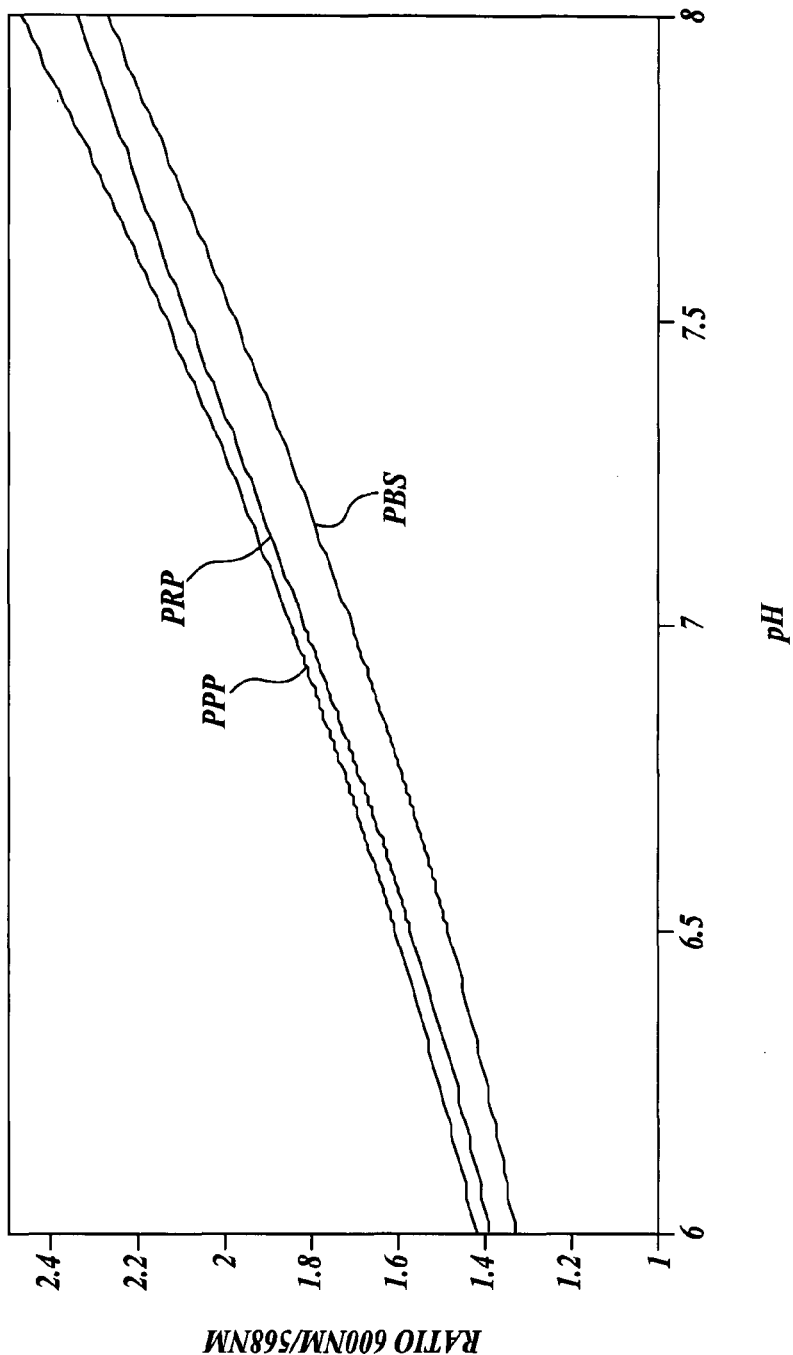
FIG. 33 illustrates the results of the method of the invention for platelet rich plasma.

FIG. 33 illustrates the results of the method of the invention for phosphate buffered saline (PBS), platelet poor plasma (PPP), and platelet rich plasma (PRP) as measured by the telescoping tubing insert assay described in Example 18. The three curves represent the best fit relationship between the measured pH and ratios for the three different liquids.

Figure 34:
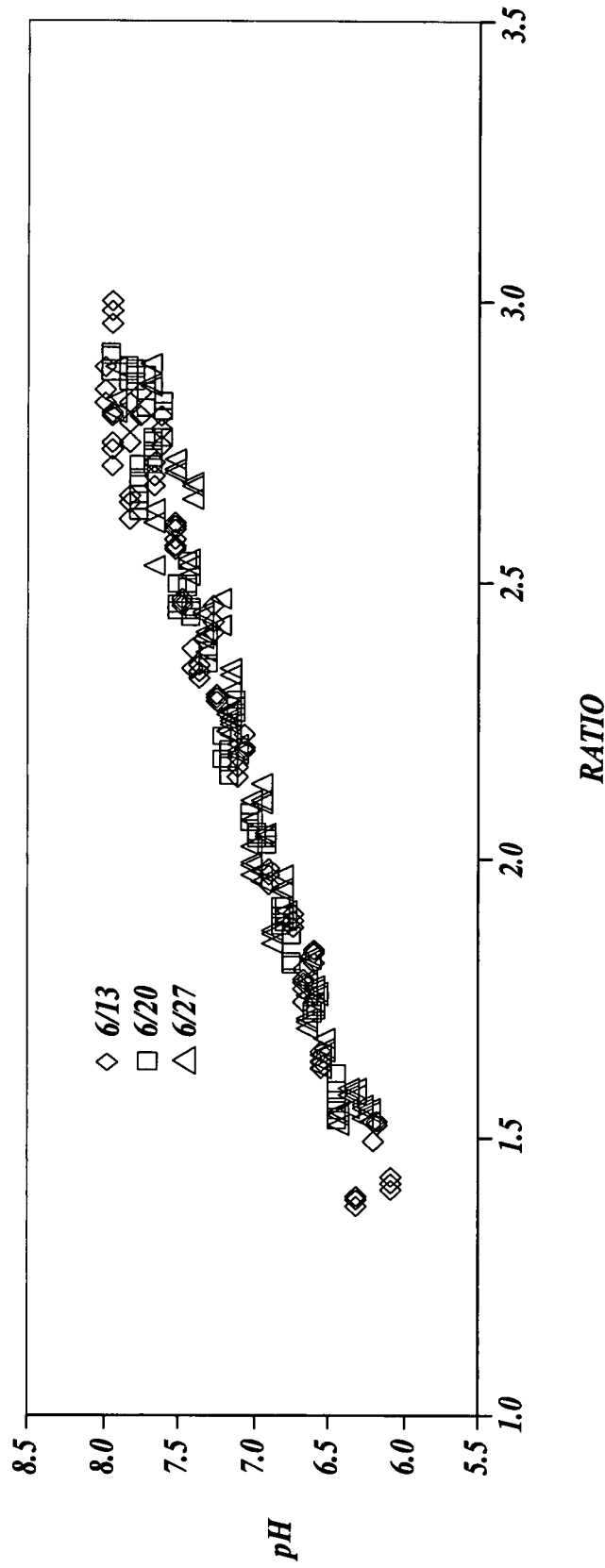
FIG. 34 illustrates the correlation of pH results for platelet rich plasma obtained by the method and system of the invention.

FIG. 34 illustrates the correlation of pH results for three different plasma samples obtained by the method and system of the invention as measured by the injection molded insert PVC tube assay described in Example 18. The relationship between the fluorescent signal and the pH has an accuracy of about 0.1 pH units.

Figure 35:
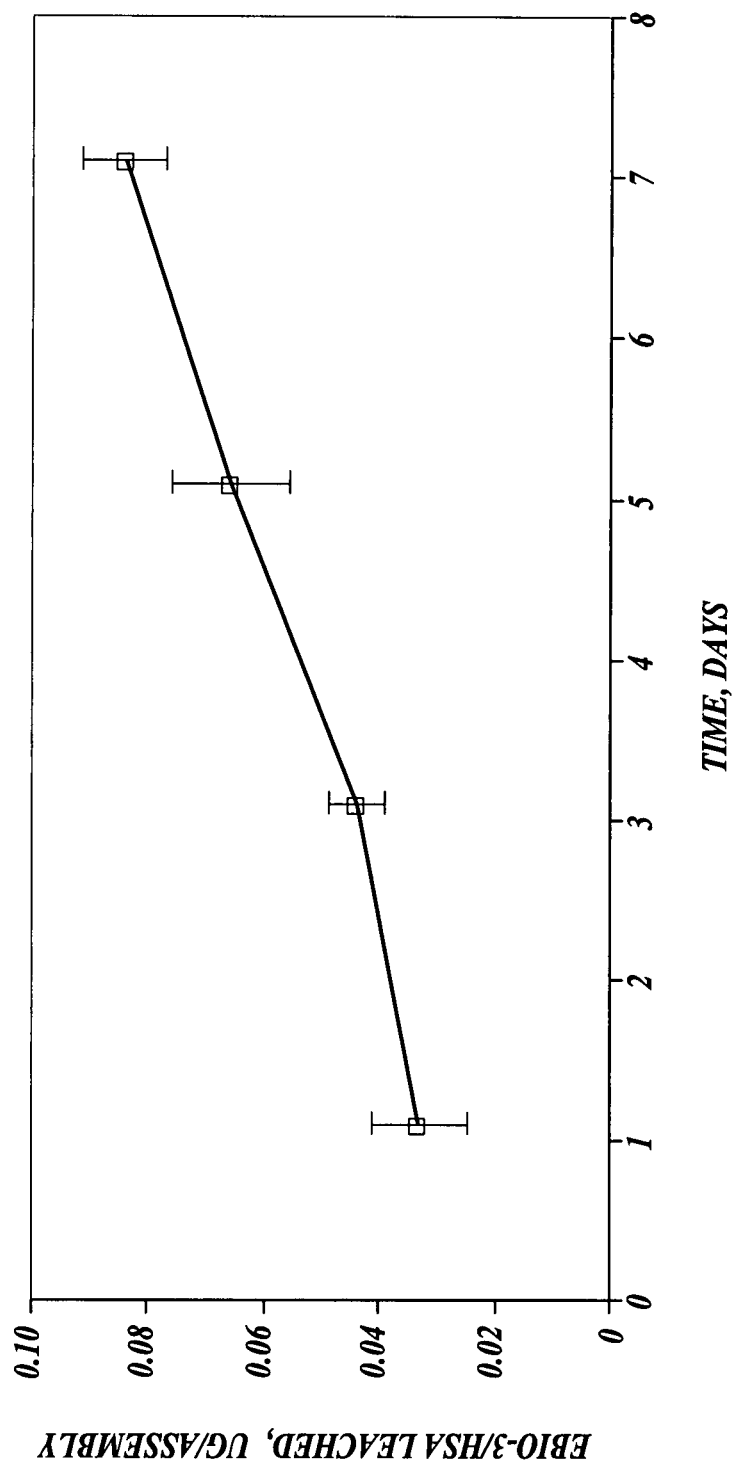
FIG. 35 illustrates stability of a representative substrate-immobilized fluorophore conjugate of the invention.

FIG. 35 illustrates stability of a representative substrate-immobilized fluorophore conjugate of the invention (EBIO-3/HSA, 2:1) on mixed ester nitrocellulose and cellulose acetate prepared by the soaking method and as measured by the leaching assay described in Example 2. The low level of leaching is far below the toxic level for any compound.

Carbon Dioxide Measurement.

In another aspect, the present invention provides a device and method for measuring carbon dioxide concentration in a liquid sample. The carbon dioxide measuring method utilizes the pH measuring method and system described above. In the carbon dioxide measuring method and device, a substrate-immobilized fluorescent species as described above is in contact with a solution, the pH of which is responsive to carbon dioxide level. In addition to being in contact with the substrate-immobilized fluorescent species, the solution having pH responsive to carbon dioxide level is in contact with a liquid sample for which the level of carbon dioxide is to be measured. The solution having pH responsive to carbon dioxide level is isolated from the liquid sample for which the level of carbon dioxide is to be measured by a selectively permeable membrane. The membrane is permeable to gases (e.g., carbon dioxide) and impermeable to other materials (e.g., liquids). Using the method of measuring pH described above, the pH of the solution responsive to carbon dioxide concentration in contact with the substrate-immobilized fluorescent species is measured and correlated with the carbon dioxide level of the sample in contact with that solution.

The solution having pH response to carbon dioxide level is an aqueous solution that includes an agent that is reactive toward carbon dioxide and changes the pH of the solution in response to carbon dioxide concentration. Suitable agents that are reactive toward carbon dioxide and change the pH of the solution in which they are dissolved include bicarbonates, such as sodium bicarbonate.

The selectively permeable membrane isolates the solution having pH responsive to carbon dioxide level from the liquid sample containing carbon dioxide. The membrane is permeable to carbon dioxide and impermeable to liquids and other solutes. In the method, carbon dioxide from the liquid sample passes from the liquid sample through the membrane and into the aqueous solution thereby reacting with the carbon dioxide reactive agent to alter the pH of the aqueous solution. Suitable selectively permeable membranes include membranes made from silicone and PTFE.

Figure 36:
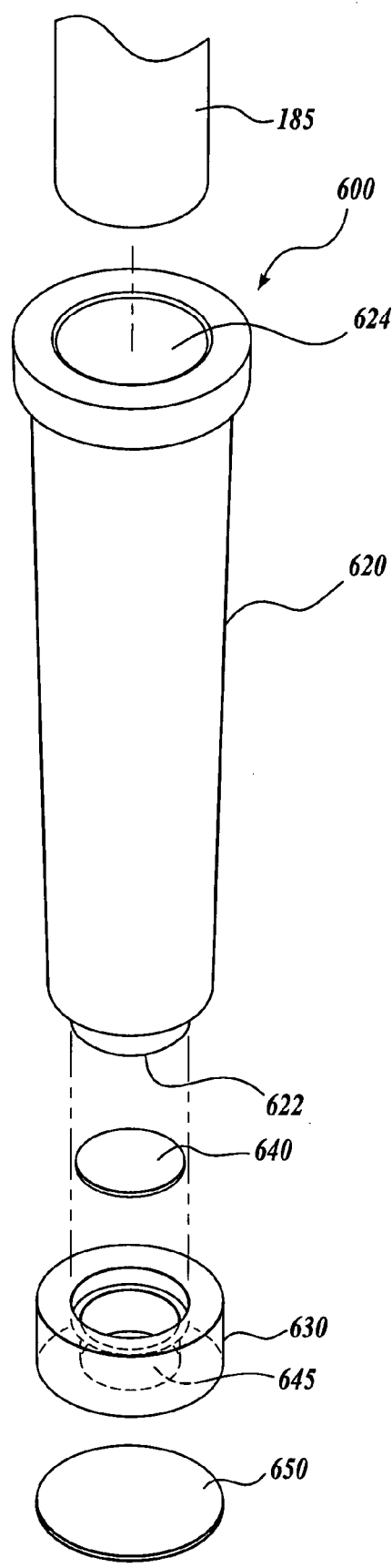
FIG. 36 illustrates a representative device of the invention for measuring carbon dioxide in a sealed vessel.
Figure 37:
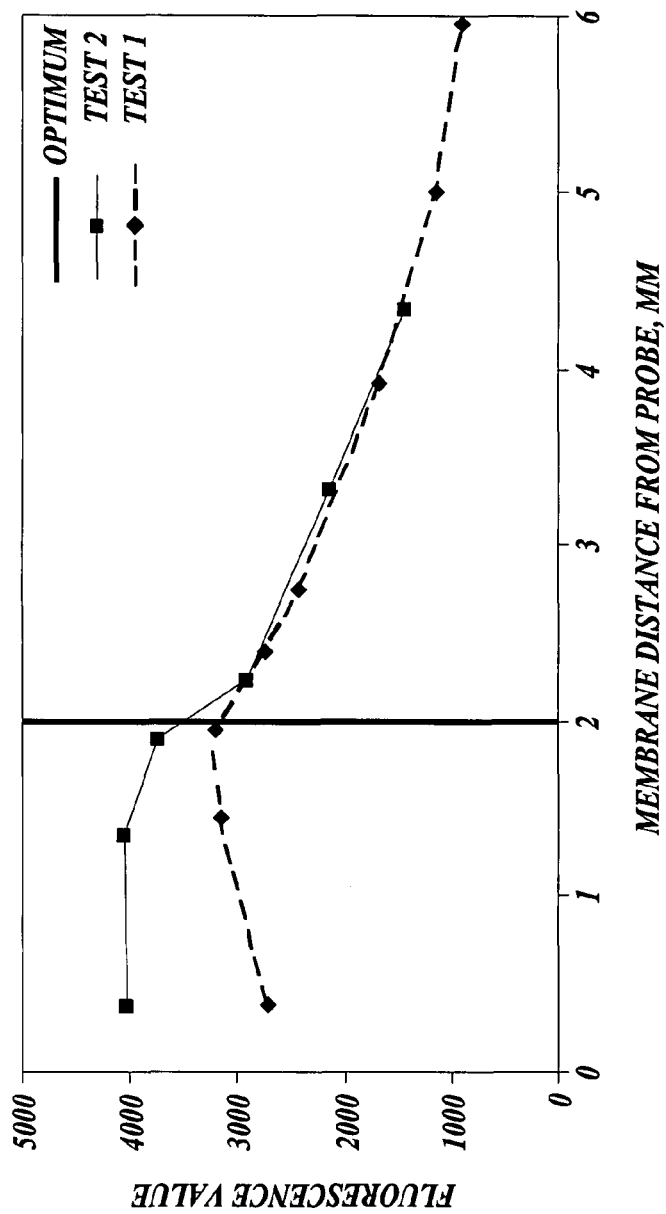
FIG. 37 illustrates the effect of probe position on fluorescent intensity in measuring pH in accordance with the invention.

FIG. 36 illustrates a representative device of the invention for measuring carbon dioxide in a sealed vessel. Referring to FIG. 36, device 600 includes port assembly 610 including port 620 and tip 630. Port 620 is a cylinder terminating with window 622 and having opening 624 for receiving probe 185. When inserted in the port, the face of probe 185 and window 622 are substantially parallel. Port 620 and tip 630 are adapted such that the port and tip are reversibly connectable. Substrate 640 including immobilized fluorescent species is secured within port 620 and tip 630. Tip 630 includes a chamber 645 for receiving a solution having pH responsiveness to carbon dioxide. Chamber 645 is defined by window 622, tip 630, and selectively permeable membrane 650. Chamber 645 includes substrate 640, which is interrogated by probe 185.

A device for measuring carbon dioxide was assembled as described above with the membrane containing immobilized EBIO-3/rHSA conjugate (rHSA is recombinant HSA). A layer of PARAFILM M, a blend of olefin-type materials, was added under the membrane towards the tip. The membrane was hydrated with 5 ul of 35 mM carbonate buffer (pH 7.4), which was sealed within the assembly by the PARAFILM M and remained hydrated throughout the assay. The assembly was subjected to 100% carbon dioxide gas by connection to the gas source with tubing and a "Y" adapter to bleed off the pressure. The assembly was subjected to the carbon dioxide for an allotted period of time, allowed to acclimate to ambient air conditions, and repeated. The fluorescence was measured at each stage at 568 nm and 600 nm after being excited at 525 nm. The results are summarized below in Table 2 and reflect changes in fluorescence due to the change in carbon dioxide concentration demonstrating that the fluorometric ratio method of the invention can also be used to calculate carbon dioxide concentration. The PVC storage bags that are used for platelet storage are somewhat gas permeable, and carbon dioxide is directly related to the measurement of pH.

TABLE 2

Carbon dioxide sensing results.

| Environmental Conditions | Emission at 568 nm | Emission at 600 nm | Ratio (600/568) |
|---|---|---|---|
| 15 min. at ambient CO$_2$ | 753 | 2184 | 2.9 |
| 5 min. at 100% CO$_2$ | 1179 | 2234 | 1.894 |
| 15 min. at ambient CO$_2$ | 833 | 2175 | 2.611 |
| 8 min. at 100% CO$_2$ | 1161 | 1930 | 1.662 |
| 60 min. at ambient CO$_2$ | 765 | 2184 | 2.854 |

The present invention provides a fluorescence-based pH indicator that can be easily inserted into the sampling ports of designed blood storage bags and interrogated using a fiber optic-based LED light source and photodiode measurement system. In one embodiment, this solid state system uses a "ratiometric" calibration method that accounts for variability in fluorescent signal strength due to interfering substances in blood that may interfere with the amount of excitation light that hits the indicator dye. The ratio of fluorescence intensities are measured at two wavelengths, one to detect the acid (protonated) isomer of the dye and one to detect the base (deprotonated) isomer.

To develop an accurate pH detector for platelet rich plasma, compounds having pKa of ~6.6 are suitable, for example, 2-chloro substitution of SNAFL compound lowers the pKa of the phenol from 7.6 to ~6.6. Conjugates of these compounds can be immobilized to various solid supports to provide sensing pH membranes.

The present invention provides an inexpensive, easy to manufacture pH sensing membrane that gives accurate measurement of pH in platelet storage bags at pH 6.5-7.5. In one embodiment, the invention uses a protein conjugate (human serum albumin) of a 2-chloro substituted ratiometric fluorescent compound. The fluorophore:HSA ratio was optimized for performance when immobilized to a nitrocellulose blot membrane. After drying on the membrane, the fluorophore:HSA conjugate has very low leaching rates. Discs of this material are easily assembled into holders for insertion into the sampling ports of platelet storage bags. The fluorescent membrane materials showed good pH response using a green LED based fluorometer. In the method, two emission wavelengths for ratiometric pH detection are measured with properly filtered photodiodes with an accuracy of ~0.1 units at the desired low pH threshold of 6.5.

Fluorescent probe molecules can be designed to be sensitive to a variety of environments. The method and system of the invention describes the use of pH-sensitive fluorophores. However, other environments can be interrogated by the method and system of the invention modified to include environment-sensitive fluorophores other than pH-sensitive fluorophores. A variety of fluorescent probes that change fluorescent properties as the molecular environment changes are commercially available. See, for example, Molecular Probes Handbook (9$^{th}$ Ed.) by R. P. Haugland. Probes can be linked to albumins or other proteins and used to prepare substrates for interrogation as described in herein or using other fluorescent-based methods. Examples of environment-sensitive fluorophores, systems, and methods include the following.

Nucleic acid detection: nucleic acid binding dyes change fluorescent properties in the presence of DNA or RNA.

Enzyme substrates: proteins or peptides can be labeled with fluorescent dyes and fluorescent quenching molecules such that a fluorescent signal is generated in the presence of particular enzymes such as proteases (FRET detection).

Probes for lipids: lipophilic dyes can change fluorescent properties in the presence of cell membranes or other lipid rich analytes.

Probes for oxygen: in addition to pH detection and carbon dioxide detection, certain fluorescent molecules are sensitive to changes in oxygen concentration, for example, tris(2,2'-bipyridiyl)ruthenium(II) dichloride (RTDP).

Indicators for metal ions: fluorescent dyes that bind metals can change fluorescent properties upon binding calcium, magnesium, zinc, sodium, potassium, among other.

Glucose detection: certain lectins such as ConA bind glucose, and suitably labeled lectins can be prepared as probes for glucose.

One object of the invention is to at least measure the parameters described above in order to solve some of the problems associated with platelet storage in sealed sterile containers. There are several problems or disadvantages described hereinafter that may be solved by the current invention as multiple parameters are monitored over time within the environment of the sealed platelet storage device. The additional advantages, objects, or computational features of the invention described herein will become apparent to those having some skill in the art upon examination or practice of the invention. The advantages and objects of the invention may be attained as particularly pointed out in the appended claims.

The following examples are provided for the purposes of illustrating, not limiting, the invention.

EXAMPLES

Example 1

The Preparation of Representative Fluorophore-Protein Conjugates

EBIO-3/HSA

Method A.

A 0.1 M stock solution of EDC (Sigma/Aldrich Chemical Co., St. Louis Mo.) was prepared by dissolving 6.2 mg of EDC in 0.2 mL of DMF and 0.123 mL of 50 mM phosphate buffer (pH 5.8). 1.0 mg of EBIO-3 acid (Nanogen, Bothell, Wash.) was dissolved in 0.102 mL of DMF to give a 20 mM solution. 3.0 mg (0.045 micromoles) of HSA (Sigma/Aldrich Chemical Co., St. Louis, Mo.) was dissolved in 0.3 mL of pH 8.5 sodium bicarbonate in each of two 1.7 mL Eppendorf tubes. 0.1M EDC (0.045 mL) was added to 20 mM EBIO-3 (0.045 mL, 0.9 micromoles) in a separate Eppendorf tube and this was added to one of the HSA tubes to give an EBIO-3:HSA offering ratio of 20:1. An offering ratio of 5:1 was used in the other HSA tube by adding a premixed solution of 0.0225 mL of EDC (0.1 mM) and 0.0225 mL of EBIO-3 (20 mM). The homogeneous dark red HSA conjugate solutions were incubated at room temperature in the dark. After 21 hours, each of the HSA conjugates was purified on a G15 Sephadex column as described above for the SNAFL conjugates (Example 13). Some unreacted EBIO-3 acid remained at the top of the column (especially for the 20:1 offering ratio), but was cleanly separated from the desired protein conjugate that eluted first as a pink fraction in ~0.5 mL of pH 7.4 buffer. Each of the purified conjugates was diluted to 0.75 mL with pH 7.4 PBS to give 4 mg/mL solutions (0.06 mM). The red solutions were stored refrigerated and protected from light. 1 micromolar solutions of each EBIO-3/HSA conjugate were prepared at pH 7.4 and analyzed by UV-vis spectra using a Beckman DU640B spectrometer. The free EBIO-3 acid (10 micromolar) spectrum had absorbance maximum at 534 nm, the 20:1 conjugate had absorbance at 538 nm and the 5:1 conjugate had maximum at 545 nm. The spectra showed the expected increase in absorbance with increasing EBIO-3:HSA offering ratio. Using this EBIO-3 acid as a standard, the 20:1 conjugate had 5.07 EBIO-3:HSA and the 5:1 offering had 1.92 EBIO-3:HSA. The coupling efficiency was somewhat lower than for the SNAFL/HSA conjugates of Example 4 (the 20:1 conjugate had 11.2 fluors/HSA and the 5:1 offering had 4.1 fluors/HAS). The EDC coupling method was suitably efficient and reproducible.

Method B.

A 0.1 M solution of EDC (Sigma/Aldrich Chemical Co., St. Louis, Mo.) is prepared by dissolving 6.0 mg of EDC in 0.194 mL of DMF and 0.118 mL of 50 mM PBS (pH 7.4). 3.0 mg of EBIO-3 acid (Nanogen, Bothell, Wash.) is dissolved in 0.306 mL of DMF to give a 20 mM solution. The two solutions are combined in the EBIO-3 solution container and incubated at room temperature for one hour in the dark. 75.0 mg (1 micromole) of liquid recombinant HSA (rHSA) from yeast (Delta Biotechnology, Ltd., Nottingham, UK) is mixed with 7.5 mL of pH 8.5 sodium bicarbonate in a 15 mL conical tube. The entire contents of the EBIO-3/EDC solution are combined with the rHSA solution and incubated at room temperature in the dark for 15-20 hours. The rHSA/EBIO-3 conjugate is purified using the Amicon stirred ultrafiltration cell system and a YM10 membrane (Millipore, Bedford, Mass.). A 50 mM PBS (pH 7.4) is used as the wash solution. After purification, the protein concentration of the conjugate is measured using the BCA™ Protein Assay (Pierce, Rockford, Ill.). An aliquot of the conjugate is diluted to 1 mg/mL with 50 mM PBS (pH 7.4) based on its BCA determined protein concentration. The 1 mg/mL aliquot of conjugate, the last milliliter of PBS effluent, an aliquot of the 50 mM PBS (pH 7.4), and an aliquot of the EB3 Standard (15 mM EBIO-3 solution in DMF and 50 mM PBS (pH 7.4)) are analyzed via an absorbance scan utilizing Bio-Tek's Synergy HT plate reader. The scan is taken on 300 microliters of each of the above mentioned samples in a black, 96-well, clear, flat bottom plate, scanned from 450 nm to 650 nm. Their max peaks are recorded and used to determine purity and quality of the conjugate.

Example 2

Immobilization of Representative Fluorophore-Protein Conjugates

EBIO-3/HSA

Spotting Immobilization Method.

EBIO-3/HSA conjugate was prepared as described in Example 1 at a ratio of 2:1. Nitrocellulose membranes were obtained from Schleicher and Schuell under the trade name PROTRAN. The discs were treated in the same way as the general immobilization method described in Example 14 using a 4 mg/mL solution of EBIO-3/HSA.

Soaking Immobilization Method.

EBIO-3/HSA conjugate was prepared as described in Example 1 at a ratio of 2:1. Mixed ester nitrocellulose and cellulose acetate membranes were obtained from Millipore under the product series TF. The EBIO-3/HSA conjugate is diluted to 0.2 mg/mL and 45 mL is added to a 9 cm disc of the membrane. The disc is agitated overnight at room temperature and protected from light. The unbound conjugate is removed and the disc is washed with two 1 hour washes and one overnight wash all with agitation. The disc is then desiccated and stored dry. Smaller discs are punched from the 9 cm disc for studies.

Example 3

The Manufacture of a Vessel Incorporating a Representative Substrate-Immobilized Fluorescent Species PVC material is compounded with a number of additives, for example, plasticizers, stabilizers, and lubricants. The formulation is used for making bags and tubes. The compounded PVC is extruded through a die or calendered in a press for converting the plasticized material into sheet form. The extruded sheet, after slitting, is cut into the desired size and sent to the welding section. The donor and transfer tubings are made by extrusion of similar PVC compounds. The tubes are then cut to the appropriate length and sent to the welding section. The components, such as transfusion ports, needle covers, and clamp, are produced by injection molding. The components are ultrasonically cleaned and dried in a drying oven.

Welding. The blood bags are fabricated by a high frequency welding technique. Sized PVC sheets are placed between electrodes and high frequency at high voltage is applied. PVC gets heated very rapidly and sealing takes place between electrodes. Transfusion ports and donor and transfer tubing are kept in the appropriate position with the bag and welded to form an integral part of the blood bag system. For the manufacture of a vessel incorporating a representative substrate-immobilized fluorescent species, an open tube is welded to provide port 510A. The tube can be made of colored PVC to provide light protection for the immobilized fluorescent species. Welded bags are trimmed. The port assembly 232 (FIG. 22) is manufactured from injection molded Lexan parts (205 and 235) and a 3.53 mm (9/64 inch) diameter nitrocellulose disc with immobilized fluorescent species (220). The port assembly is held together by friction fit or can be glued in place. The port assembly is inserted in the open tube of port 510A. The port assembly is held in the port by friction fit or can be glued in place. The assembled bag and port assembly is sterilized and labeled for ultimate storage of platelet concentrates.

Example 4

The Incorporation of a Representative Substrate-Immobilized Fluorescent Species into a Sealed Vessel The port assembly is manufactured from injection molded Lexan parts and a 3.53 mm (9/64 inch) diameter nitrocellulose disc with immobilized fluorescent species. The port assembly is held together by friction fit or can be glued in place. The port assembly is inserted through the septum seal inside port 510A by puncturing the seal with the spiked tip. Alternatively, the seal can be pre-punctured with a separate spike tool. The insertion of the port assembly can be performed on either empty or platelet filled bags, but in either case, aseptic methods should be used to avoid possible contamination of the bag contents. The port assembly is held in the port by friction fit or can be glued in place. The vessel remains sealed (leakproof) after insertion of the port assembly in the port.

Example 5

Assembly of Inserts and Bags

The methods described in Examples 3 and 4, above, were followed with the following exceptions: an altered version of the injection molded insert tip 235, shown in FIG. 22, was used. After friction fit assembly, the shaft, tip and membrane disc were pushed into an opaque blue sleeve of PVC tubing (Natvar, City of Industry, Calif., durometer 80 Shore A, dimensions=ID 0.216", OD 0.291", L 1.15") until the flange contacted the tubing. The prongs just reach the other end of the tubing. This friction fit assembly was fit inside the assembled large bag as shown in FIG. 1.

Assembly of Inserts into Bags.

The bags were welded with large diameter PVC tubing (inner diameter slightly smaller than the outer diameter of the blue insert assembly, ¼ inch shorter than the blue insert assembly). The blue insert assembly was held into the larger diameter PVC tube in the bag by friction fit or by solvent welding with cyclohexanone. The blue sleeve protrudes from the flush cut bag tubing by ¼ inch, thus providing a space for the "clip" on the instrument.

Preparation of Small Bags.

Method A.

The small bag shape shown in FIG. 2 was welded from previously assembled large bags (with no inserts or twist off sample ports). One of the tubing ports for the sample ports is discarded along with much of the citrate PVC film. The blue pH reading insert assembly, pigtail tubing and sample ports were carefully assembled with cyclohexanone solvent welding and packaged for sterilization.

Method B.

Two sheets of breathable citrate PVC film (Solvey-Draka) are RF welded together using a steel tool that contacts the film in the outer shape of the bag in FIG. 2. PVC tubes on steel rods are also placed between the two layers of the film before the RF welding. This forms a leak proof seal with the tubes and film. After the RF welding the steel rods are removed so that twist off ports, pigtails and sensors can be placed in the PVC tubes. These features are solvent bonded or fixed in another way into the tubes.

Ethylene Oxide Sterilization of Bag/Insert Assembly.

The bags were individually wrapped and sterilized using a standard ethylene oxide cycle used for other platelet storage bags. The overwrapped bags were packaged in boxes and unwrapped just prior to use.

Example 6

Protocol Description for Large Bag pH and Platelet Health

An in vitro evaluation of PCs during storage in representative large and small platelet storage containers with integrated pH probes was performed. The evaluation determined that the integrated pH device had no negative impacts on in vitro quality of platelets during storage, either during storage in standard platelet containers or during storage in down-scaled containers for research purposes. The following example refers to the data presented in FIGS. 3-7.

Platelet Storage Containers

A. 4 large experimental PVC-citrate storage containers (lot number m4340) with integrated pH probe (for storage of about 300 mL PC), ETO sterilized.

B. 4 large approved PVC-citrate storage containers (brand Fresenius, T2110, batch H10211011) (for storage of about 300 mL PC), steam sterilized.

C. 4 small experimental PVC-citrate containers with integrated pH probe (for storage of about 17 mL PC), ETO sterilized.

D. 4 small PVC-DEHP (so-called buffy coat bags; 100-150 mL nominal volume), steam sterilized.

All other materials are standard materials used by the Sanquin Blood Centre Region North West for blood collection and by the SR-BTT laboratory for blood processing and testing.

A representative system of the invention (serial number PH05100007, firmware version 2.00, Blood Cell Storage, Inc., Seattle, Wash.) was used for non-invasive fluorescence measurements of the storage containers with integrated pH probes. For the data presented in FIGS. 3-10 and 16, each bag was positioned on a representative system (device) of the invention and the fluorescent ratio was determined from which pH was calculated. Readings/samplings were done at 4 hours post set-up then every 6-12 hours later over a period of 7 to 11 days. The volume in the small storage containers was to about 15 mL.

The first two PC were combined, and then two small bags were filled with each about 15 mL, followed by distribution of the remaining volume in two equal volumes over the two types of large storage containers.

In order to ascertain a good starting quality of the platelets, a measurement of CD62P expression on day 1 of storage was included.

The number of platelets positive for PAC-1 (fibrinogen binding site on glycoprotein IIb/IIIa) was not determined, because the test was shown to be influenced by the presence of plasma.

Blood Collection

Standard blood collection systems (manufactured by Fresenius HemoCare, Emmer-Compascuum, the Netherlands) were filled with approximately 500 mL of blood during blood collection at the Sanquin Blood Centre Region NorthWest (Sanquin Blood Supply Foundation, Amsterdam, the Netherlands) from non-enumerated, informed donors. The day of blood collection was designated as day 0 of the study.

Blood collections were performed under standard conditions, with the aid of calibrated blood collection balances equipped with a mixing platform allowing mixing at regular intervals, monitoring of blood flow and bleeding time, a final check of the weight of the donation and cooling of the blood to 20° C. immediately after collection. At least 40 donations (20 from A-Rh(+) and 20 from 0-Rh(+) donors) meeting the criteria of volume (500±50 mL of blood) and bleeding time (<15 min) were selected by the Blood Centre for further processing to plasma, red cell concentrate in SAG-Mannitol and buffy coat 12 to 16 h after the blood collection (on day 1 of the study). After centrifugation and Compomat G4 separation of the whole blood, at least 40 buffy coats were delivered to the BTT laboratory. In addition, per set of 5 buffy coats a plasma unit from one of the corresponding 5 donations was delivered.

Preparation of Pooled Platelet Concentrates

The 40 buffy coats were used to prepare 6 pools, each consisting of 5 buffy coats and one unit of plasma. Pools consist of units of the same blood group. From these buffy coat pools, platelet concentrates were prepared after a second centrifugation step (Hettich Roto Silenta/RP, 5 min at 1700 rpm, 905×g, brake 3). Conditions for these separations are selected in such a way that from each pool of buffy coats a platelet concentrate (PC) of ±320 mL volume with 1-1.5× 10e9 platelets/mL and a leukocyte contamination of less than 50×10e7 leukocytes per concentrate was obtained. During preparation of PC from the pooled buffy coats, the concentrates are filtered over a Compostop CS leukoreduction filter (Fresenius Hemocare, 50 $cm^2$, T3995) with a large PVC-citrate container connected to the outlet of the filter. For 4 PC this container was container A and for 4 PC this was container B (see Materials and Instruments; A and B were matched for blood group).

Pooling and Splicing of Platelet Concentrates

After preparation, a PC in container A was combined with a PC in container B (blood group matched) and after mixing two times 15 mL was transferred to a container C and a container D. Subsequently, the remaining volume was redistributed over the A and B containers in such a way that the volume was equal.

Storage of Platelet Concentrates

The filtered PC were stored for 8 days after preparation at 22° C.±2° C. horizontally shaking with 1 cycle per minute. Samples were taken under aseptic conditions after 1, 2, 3, 6, 7 and 8 days of storage (meaning day 2, 3, 4, 7, 8 and 9 of PC shelf-life) and analyzed for various platelet quality parameters.

Measurements

The following features of platelet quality were measured:

1. Morphological parameters (measured after 3 days, 6 days and 8 days of storage). The morphological parameters involve the screening of the swirling (resulting in a swirling score) and the microscopic characterization of the different forms of platelets, i.e. discoid, discoid with dendrites, balloons or spheres, resulting in a so-called Kunicki score.

2. Physical changes (measured after preparation and after 1, 2, 3, 6, 7 and 8 days). The physical changes are characterized by measurements of the pH, $P(O_2)$ and $P(CO_2)$ and the number of leukocytes (counted at day 0) and the number of platelets.

3. Changes in activation degree (measured after 3 days, 6 days and 8 days). The changes in degree of activation were measured with a monoclonal antibody, directed against activation-dependent antigen CD62P. Also the percentage of platelets expressing phosphatidyl-serine (PS, measured with AnnexinV) was determined.

4. Metabolic changes (measured after 3 days, 6 days and 8 days). The metabolic changes are characterized by the intracellular amount of adenine nucleotides, the extracellular concentration of glucose and lactate and the mitochondrial membrane potential (as measured with JC-1).

At the end of the storage period, the platelet concentrates in the large containers were checked for sterility.

A. Composition of the Platelet Concentrates.

During preparation of the platelet concentrates from the pooled buffy coats, no deviations from normal procedures were observed, with a filtration time over the in-line filter of about 6 min. The eight leukodepleted products were used to prepare 4 pools, which were subsequently distributed over the small containers (type C and D, each 15 mL) and the large containers (type A and B, about 300 mL each). Table 2 shows that the PC in type A and type B containers were very similar. After leukoreduction, the number of leukocytes was well below $1×10^6$ in all units (as determined by fluorescent Nageotte counting, with for every sample 0 counted). The total number of platelets in each pool exceeded $300×10^9$, and these numbers meet the requirements of the Council of Europe for leukocyte depleted PC.

TABLE 3

Composition of the platelet concentrates

| | | Type A | Type B |
|---|---|---|---|
| Volume PC | mL | 313 ± 5.8 | 308 ± 6.2 |
| Platelet conc. | ×10⁹/mL | 1172 ± 58.0 | 1172 ± 58.0 |
| Total platelets | ×10⁹ | 367 ± 16.8 | 361 ± 18.3 |
| Total WBC | ×10⁶ | 0.10 ± 0.08 | 0.09 ± 0.07 |

Values given are the mean ± SD of 4 concentrates.

B. Change in Morphological Parameters.

The viability of platelets after transfusion correlates fairly well with platelet morphology. The most discoid platelets have the best in vivo survival, whereas spherical platelets perform much less. A morphological index was introduced by Kunicki to predict viability of platelets after transfusion. The number of discs identified in a 100 cell count of fixed platelets under the microscope is multiplied by 4, spheres by 2, platelets with dendrites by 1, and balloons by 0, resulting in a maximal score of 400 for perfect discoid platelets.

The morphology scores and the percentage discoid platelets during storage of the PC pools are depicted in Table 2.

TABLE 4

Morphological parameters of platelet concentrates during storage

| Bag type | | Day 4 of shelf-life | | Day 7 of shelf-life | | Day 9 of shelf-life | |
|---|---|---|---|---|---|---|---|
| | | Kunicki score | % discoid | Kunicki score | % discoid | Kunicki score | % discoid |
| A | Mean | 295 | 50 | 279 | 44 | 248 | 31 |
| | SD | 20.4 | 8.2 | 11.8 | 4.8 | 8.7 | 2.5 |
| B | Mean | 288 | 46 | 263 | 38 | 228 | 24 |
| | SD | 22.5 | 9.5 | 15.5 | 6.5 | 8.7 | 2.5 |
| C | Mean | nd | nd | 268 | 39 | nd | nd |
| | SD | nd | nd | 5.0 | 2.5 | nd | nd |
| D | Mean | nd | nd | 263 | 36 | Nd | nd |
| | SD | nd | nd | 17.1 | 8.5 | Nd | nd |

Values given are the mean ± SD of 4 concentrates.
Days indicate the number of days after blood collection (day 0).
nd: not determined The first measurement, after 3 days of storage (day 4 of PC shelf-life indicated in the table), indicates a high quality of the platelets. During further storage the morphology score remains high, with only minimal differences between the two types of large containers tested. Also the values for the small containers, only determined on day 7, were very similar, indicating also good storage characteristics for these small containers.

Another method to judge morphology of platelets is the observation of the swirling pattern in the storage bag. The "silk-like" patterns are observed visually, after brief squeezing of the bag and the degree of inhomogeneity is scored according to the following scale:

3. Swirling inhomogeneity throughout the whole bag, with contrast observable as fine detail 2. Swirling inhomogeneity visible throughout the whole bag with good contrast 1. Some inhomogeneity visible, but only in a few places and with poor contrast 0. Turbid homogeneity, no effect of squeezing.

With this method for freshly prepared platelet concentrates a score is obtained of 3, whereas after storage for 6 days the score should be above 2.

Table 2A shows that during storage for up to 8 days (day 9 of shelf-life) the score in the large containers was above 2, with minimal differences between the two tested types of container. In the small containers the score was above 2 till day 6, whereas the swirling score was slightly lower in the small PVC-DEHP bag compared to the small PVC-citrate bag.

TABLE 5

Swirling scores of platelet concentrates during storage

| | Type | day 2 | day 4 | day 7 | day 8 | day 9 |
|---|---|---|---|---|---|---|
| Mean | A | 3.0 | 2.6 | 2.5 | 2.4 | 2.1 |
| SD | | 0.0 | 0.1 | 0.0 | 0.3 | 0.3 |
| Mean | B | 3.0 | 2.8 | 2.2 | 2.2 | 2.3 |
| SD | | 0.0 | 0.2 | 0.3 | 0.1 | 0.2 |
| Mean | C | 3.0 | 2.8 | 2.4 | 2.4 | 2.2 |
| SD | | 3.0 | 0.2 | 0.1 | 0.1 | 0.1 |
| Mean | D | 3.0 | 2.9 | 2.0 | 1.9 | 1.6 |
| SD | | 3.0 | 0.1 | 0.2 | 0.1 | 0.1 |

Values given are the mean ± SD of 4 concentrates.
Days indicate the number of days after blood collection (day 0).
nd: not determined C. Change in Physical Parameters.

When during storage of platelets the pH falls below 6.7 (measured at 37° C.), disc-to-sphere transformation occurs and morphology of the platelets becomes worse. This change becomes irreversible when the pH falls below 6.5 and therefore, at the end of storage, CE requirements prescribe a pH between 6.6 and 7.2 (measured at 37° C.) or between 6.8 and 7.4 (measured at 22° C.). The pH values during storage in the large containers type A and B and the values for $pCO_2$, $pO_2$ and bicarbonate are given in Table 3a. During storage the pH remains above 6.9 during 8 days (=9 days of shelf-life), with only minimal differences between the two container types tested. In the small containers (type C and D) the pH was only measured on day 6 of storage. Compared to the large containers the pH was slightly lower on this day, indicating slightly worse storage conditions in the small containers. $pCO_2$ and $pO_2$ showed the normal pattern during storage of platelet concentrates.

TABLE 6

Physical parameters during storage

| | | pH at 37° C. | | $pCO_2$ | | $pO_2$ | | $HCO_3^-$ | |
|---|---|---|---|---|---|---|---|---|---|
| Shelf-life | type | mean | SD | Mean | SD | mean | SD | mean | SD |
| Day 1 | A | 7.058 | 0.023 | 66.5 | 2.1 | 156.0 | 2.7 | 18.3 | 0.5 |
| | B | 7.058 | 0.023 | 66.5 | 2.1 | 156.0 | 2.7 | 18.3 | 0.5 |
| Day 2 | A | 7.196 | 0.013 | 43.8 | 0.5 | 80.6 | 6.6 | 16.6 | 0.5 |
| | B | 7.173 | 0.008 | 46.7 | 0.5 | 65.8 | 10.5 | 16.8 | 0.4 |
| Day 3 | A | 7.229 | 0.019 | 36.5 | 1.8 | 87.4 | 7.3 | 14.9 | 0.7 |
| | B | 7.200 | 0.006 | 39.1 | 1.6 | 73.2 | 4.7 | 14.9 | 0.7 |
| Day 4 | A | 7.229 | 0.010 | 33.4 | 0.6 | 84.3 | 8.8 | 13.6 | 0.4 |
| | B | 7.190 | 0.008 | 36.2 | 2.1 | 65.6 | 5.2 | 13.5 | 0.6 |
| Day 7 | A | 7.095 | 0.018 | 30.2 | 1.5 | 98.4 | 6.1 | 9.1 | 0.7 |
| | B | 7.077 | 0.010 | 32.1 | 1.7 | 84.6 | 5.6 | 9.2 | 0.3 |
| Day 7 | C | 7.052 | 0.089 | 19.5 | 1.3 | 153.4 | 7.7 | 0.8 | 5.4 |
| | D | 6.900 | 0.054 | 41.1 | 3.1 | 117.5 | 13.2 | 1.0 | 7.9 |
| Day 8 | A | 7.013 | 0.025 | 29.1 | 1.2 | 110.2 | 10.3 | 7.3 | 0.6 |
| | B | 7.004 | 0.006 | 31.3 | 0.9 | 91.3 | 4.1 | 7.6 | 0.2 |
| Day 9 | A | 6.921 | 0.027 | 30.1 | 1.7 | 107.4 | 4.5 | 6.1 | 0.7 |
| | B | 6.935 | 0.007 | 31.4 | 0.8 | 90.0 | 4.2 | 6.5 | 0.2 |

Values given are the mean ± SD of 4 concentrates.
Days indicate the number of days after blood collection (day 0).

During storage in the large containers the platelet concentration showed only minimal variation during storage, whereas for the small containers about 5% decrease was found at day 7 (Table 3b).

TABLE 7

Platelet concentration during storage

| | bag type | day 1 | day 3 | day 4 | day 7 | day 8 |
|---|---|---|---|---|---|---|
| Mean | A | 1172 | 1215 | 1221 | 1219 | 1233 |
| SD | | 58.0 | 68.9 | 55.1 | 67.1 | 79.3 |
| Mean | B | | 1202 | 1226 | 1250 | 1182 |
| SD | | | 69.1 | 65.5 | 64.9 | 46.0 |
| Mean | C | | | | 1163 | |
| SD | | | | | 109.0 | |
| Mean | D | | | | 1137 | |
| SD | | | | | 83.3 | |

Values given are the mean ± SD of 4 concentrates.
Days indicate the number of days after blood collection (day 0).

D. Changes in Metabolic Parameters During Storage.

The glucose concentration measured after 1 day of storage (day 2 of PC shelf-life) was similar as observed in most other studies with storage in plasma.

Glucose consumption during storage was also similar as previously observed (about 6 mM in 5 days) with a concomitant increase of lactate of about 10 mM, indicating a major role for aerobic glycolysis in glucose consumption. Hardly any differences were found between the tested types of large containers. The values for the small containers were also very similar, but the results indicated slightly more glucose consumption in the small containers compared to the large containers.

TABLE 8

Glucose and lactate in supernatants of PC's during storage

| | | Day | | | | | | |
|---|---|---|---|---|---|---|---|---|
| | | 1 | 2 | 3 | 4 | 7 | 8 | 9 |
| Bag A | glucose | 20.7 | 20.0 | 18.8 | 17.3 | 14.1 | 13.7 | 10.4 |
| | lactate D | 6.6 | 7.9 | 10.1 | 10.2 | 17.0 | 18.1 | 19.1 |
| Bag B | glucose | 20.7 | 20.3 | 19.2 | 17.7 | 14.3 | 14.2 | 11.0 |
| | lactate D | 6.6 | 8.3 | 10.4 | 10.2 | 16.3 | 17.3 | 17.4 |
| Bag C | glucose | 20.7 | | | | 12.1 | | |
| | lactate D | 6.6 | | | | 21.3 | | |
| Bag D | glucose | 20.7 | | | | 13.1 | | |
| | lactate D | 6.6 | | | | 18.3 | | |

Values given are the mean ± SD of 4 concentrates, paired study.

The metabolic state of platelets is well characterized by the intracellular amounts of nucleotides on the various days. A correlation between ATP content and in vitro survival was found by Holme et al. Platelets contain two pools of nucleotides, a metabolic pool with an ATP:ADP ratio of about 10, and a storage pool (in the dense granules) with an ATP:ADP ratio of about 1, resulting in an overall ratio of about 2 in a total platelet extract. It was found in earlier studies that during storage the storage pool is depleted in favor of the metabolic pool, reflected by a slightly increased ATP/ADP ratio.

The results for the nucleotide analyses (Table 9) showed no differences between the two tested containers and overall the results are similar to results found with other studies using the B-type container at SR-BTT. The results for the small containers at day 7 (not shown) were very similar to the data found at day 7 for the large containers.

TABLE 9

Nucleotide content in PC's during storage

| | units | day 4 | day 7 | day 9 |
|---|---|---|---|---|
| A-series | | | | |
| ATP | pmol/$10^6$ | 51.4 ± 1.22 | 46.4 ± 4.83 | 41.9 ± 1.72 |
| ADP | pmol/$10^6$ | 27.7 ± 1.00 | 22.7 ± 2.25 | 19.2 ± 0.86 |
| AMP | pmol/$10^6$ | 4.3 ± 0.31 | 3.1 ± 0.45 | 2.8 ± 0.20 |
| ATP:ADP | | 1.85 ± 0.02 | 2.04 ± 0.01 | 2.19 ± 0.09 |
| B-series | | | | |
| ATP | pmol/$10^6$ | 51.2 ± 4.04 | 45.1 ± 1.37 | 42.1 ± 2.00 |
| ADP | pmol/$10^6$ | 27.4 ± 2.61 | 21.4 ± 1.04 | 18.4 ± 0.86 |
| AMP | pmol/$10^6$ | 3.5 ± 0.32 | 3.6 ± 1.20 | 2.6 ± 0.24 |
| ATP:ADP | | 1.87 ± 0.03 | 2.11 ± 0.06 | 2.28 ± 0.07 |

Values given are the mean ± SD of 4 concentrates, paired study.

The mitochondrial membrane potential ($\Delta\Psi$) was measured with the fluorescent dye JC-1. This dye accumulates in the mitochondrial matrix in response to the membrane potential across the mitochondrial inner membrane and, above a critical concentration, J-aggregates are formed which show a red shift in emission characteristics as compared to the monomeric state. Therefore, the ratio of red (FL2) over green (FL1) fluorescence as measured in the flow cytometer is an indicator for the $\Delta\Psi$, with a high value indicating active mitochondria and a lower value indicative for mitochondrial damage. Table 10 shows that the FL2/FL1 ratio starts high on day 2 and remains high during storage, with only minimal differences between the two types of containers tested.

E. Change in Membrane Characteristics of the Platelets.

Changes in cell surface antigens are indicative for the degree of activation of platelets during storage of PC's at room temperature. These so-called activation antigens can be detected with monoclonal antibodies (MAb). In this study we used an antibody against CD62P. In resting platelets, the CD62P antigen is only present in the membranes of α-granules, whereas after activation this antigen is also expressed on the cell membrane.

Results for Large Containers

Table 10 shows the changes in expression (percentage positive cells) for CD62P from day 2 to day 9 of the PC shelf-life. The results show a moderate degree of activation, as is observed in all studies on platelet storage, whereas there are minimal differences between the two types of large containers tested.

TABLE 10

Changes in cell surface markers and JC-1 during storage of PC's

| | Series | CD62P mean % | SD | AnnexinV mean % | SD | JC-1 mean ratio | SD |
|---|---|---|---|---|---|---|---|
| Day 2 | B | 7.6 | 1.0 | nd | | Nd | |
| Day 4 | A | 11.2 | 1.4 | 7.3 | 0.9 | 2.9 | 0.5 |
| Day 4 | B | 10.9 | 1.4 | 6.6 | 0.9 | 3.0 | 0.3 |
| Day 7 | A | 13.2 | 1.4 | 14.2 | 1.6 | 3.2 | 0.3 |
| Day 7 | B | 12.5 | 1.9 | 14.8 | 1.2 | 3.0 | 0.2 |
| Day 9 | A | 19.9 | 2.0 | 16.7 | 2.2 | 3.0 | 0.2 |
| Day 9 | B | 16.7 | 1.7 | 17.3 | 1.6 | 2.8 | 0.2 |

Values given are the mean ± SD of 4 concentrates (paired study);
%: percentage positive platelets.

In addition to the measurement of the cell surface expression of the CD62P antigen, the percentage of cells expressing phosphatidyl-serine (PS) was measured. Under normal conditions platelets exhibit an asymmetric distribution of phospholipids in the membrane. The choline-containing phospholipids, phosphatidyl choline and sphingomyelin, predominantly reside in the outer leaflet, while the aminophospholipids, phosphatidyl-ethanolamine (PE) and PS, are found mainly in the inner leaflet. PS-exposure can be measured with Annexin-V and a high expression is generally thought to be a signal for removal of cells from the circulation. Table 6a shows the percentage of platelets positive for Annexin-V binding on the various days during storage, indicating that initially a very low percentage of cells are positive for PS-exposure. During storage some increase is found, but the mean value at day 9 is still low, indicating a good in vitro quality. Moreover, the values found for the two types of container tested are very similar in the paired study.

Results for Small Containers

Table 11 shows the changes in expression (percentage positive cells) for CD62P from day 2 to day 7 of the PC shelf-life for the two types of small containers tested. The results show a moderate degree of activation, slightly higher than that observed on day 7 in the large containers. Only minimal differences were seen between the small PVC-citrate bag with a representative probe (type C) and the small PVC-DEHP bag (type D). The JC-1 ratio on day 7 was similar to that found in the large containers.

TABLE 11

Changes in cell surface markers and JC-1 during storage of PC's

|  | Series | CD62P mean % | SD | AnnexinV Mean % | SD | JC-1 mean ratio | SD |
|---|---|---|---|---|---|---|---|
| Day 2 | B | 11.6 | 14.4 | Nd |  | nd |  |
| Day 7 | C | 17.6 | 1.5 | 16.8 | 1.6 | 3.2 | 0.3 |
| Day 7 | D | 18.5 | 1.2 | 16.3 | 3.8 | 3.6 | 0.5 |

Mean ± SD for n = 4, paired study.

F. Sterility at the of the Storage Period.

At the end of the storage period of 14 days (after day 9 some non-invasive fluorescent measurements were performed, separately reported), one PC (2A) was found to be positive after direct seeding in soybean-casein hydrolysate or fluid thioglycolate as substrate and incubation at 20-25° C. respectively 30-32° C., according to CLB protocol M 139 (title "Onderzoek op steriliteit"). Upon looking back to the individual data there was no reason to exclude 2A from the data set, most probably this was a contamination introduced in the final days of storage, due to the frequent sampling for blood gasses (normally the sample site coupler is used 3-4 times during a study, this study up to 10 times).

Conclusions

The platelet concentrates met the requirements of the research protocol and those of the European guidelines.

During storage under standard blood bank conditions, only minimal differences were found between the storage in the representative container compared to the control Fresenius container (both PVC-citrate, paired study with full-scale platelet concentrates in plasma).

During storage under standard blood bank conditions, the various measured in vitro parameters for both types of large containers tested, were similar to values observed in earlier platelet storage studies.

The values for the in vitro quality parameters at the end of study (8 days of storage, 9 days of shelf-life) predicted a good in vivo recovery and survival at the end of maximal (7 days) shelf-life.

Overall, the results of the present study indicate no harmful effect induced by the tested representative platelet storage containers with integrated pH probe.

The analysis of in vitro parameters on day 6 of storage in the small containers indicated that the storage conditions for the down-scaled approach were slightly worse than in the full-scale study. Therefore, it would be better to reduce the stored volume in the small containers to 13-14 mL, in order to mimic the full-scale conditions more closely.

Example 7

Bacterial Strains. The data in FIGS. 9 and 10 were obtained by measuring various parameters of PC samples inoculated with bacteria. Bacterial strains were cultivated from −80° C. frozen stocks by two consecutive overnight passages at 37° C. on 5% blood agar (PML, Wilsonville, Oreg.). All strains used were received as Microbiologics Kwik-Stiks purchased from PML except the *Escherichia coli* strain (CFT073) which was received from Dr. S. Mosely at the University of Washington, Seattle, Wash. The American Type Culture Collection strains used are *Staphylococcus aureus* ATCC 29213, *Klebsiella oxytoca* ATCC 43863, *K. pneumoniae* ATCC 13882, *Serratia marcescens* ATCC 43861 and *Pseudomonas aeruginosa* ATCC 27853. All strains except the *E. coli* were conditioned in plasma over three serial passages with incubation at 22° C. than frozen at −80° C.

Processing and Inoculation of Bacterial Strains.

The small platelet storage bag depicted in FIG. 2 was used for the bag tracking studies. A sampling port (Baxter Healthcare Corp., Deerfield, Ill.) is placed in each bag. Using a 20 mL syringe (Becton Dickinson ((BD)), Franklin Lakes, N.J.) and a 22G needle (BD), approximately 13-14 mL of platelet concentrate (PC) is removed from the apheresis unit received from Puget Sound Blood Center and aseptically transferred to the small bag for use as a normal or spiked sample. Underfilled samples were prepared with only 7 mL of PC. The inoculum for the spiked bags is obtained from an overnight subculture on blood agar of the desired strain at 37° C. without $CO_2$. A suspension of bacteria in sterile saline is adjusted to the turbidity of a 0.5 McFarland Standard which is roughly equivalent to 1E8 CFU/mL. This suspension is further diluted in sterile saline and spiked into the prepared bags to give a final concentration of approximately 10, 100 or 1000 CFU/mL.

Sampling for Analysis by Bayer Blood Gas Analyzer and One-Touch Ultra Glucose Meter.

Following transfer of PC and spiking of bacteria, small bags were placed in the Helmer incubator/shaker at 22° C. for 4 hours of equilibration. After initial equilibration the bags were removed, the sampling port was cleansed with 95% ethanol and a sample was removed using a 1 mL syringe (BD) with 22G needle. The sample was divided between culture for CFU/mL, glucose meter and blood gas analyzer (Bayer RapidLab model number 348. Bacterial spiked bags required a sample of ~0.4 mL for testing. Bags presumed to be sterile (normal or underfilled) required a sample of ~0.25 mL for testing as sterility checks were done instead of CFU/mL determinations.

CFU/mL determinations were performed by serial dilution (1 in 10) of 0.1 mL platelets. The amount plated on Tryptic Soy Agar (PML) was 0.1 mL platelets (and/or dilutions thereof), utilizing ~0.2 mL of sample. Plates were incubated at 37° C., colonies were enumerated after 24 hours and CFU/mL were calculated. The limit of quantitation is 10 CFU/mL. One drop of PC on sheep blood agar was used as a sterility check with the plates incubated at 37° C. for at least 4 days.

Approximately 0.15 mL of the sample was used for pH blood gas analysis (Bayer 348, Bayer HealthCare, Norwood, Mass.). Samples were run immediately after dispensing the amount necessary for CFU/mL or sterility determinations. Readings for pH, $pCO_2$ and $pO_2$ were obtained.

Glucose was determined utilizing the OneTouch Ultra meter and test strips (Lifescan, Milpitas, Calif.) following manufacturer's instructions. Sample utilized per reading was less than 10 µl and results were recorded in mg/dL.

Example 8

Fluorescence and pH Properties of Representative SNAFL Analogs pKa Determination Instrumentation.

Fluorescence versus pH of various SNAFL free acids were compared using an Ocean Optics USB2000 fiber optic spectrometer and a tungsten halogen light source (part number HL-2000 FHSA). The light source was equipped with a linear variable filter that allowed the wavelength and shape of the excitation beam to be adjusted. The excitation wavelength was adjusted by using a blank cuvette to the absorbance max of the fluorophore (see Table 1). A cuvette holder (part number CUV-FL-DA) was directly attached to the light source and a fiber optic cable directed emitted light to the spectrometer. Excitation conditions are reported for each fluorescence spectrum (3000 msec irradiation at the indicated wavelength). Spectral data were collected on a personal computer using the Ocean Optics software and overlays of different spectra were captured.

Sample Preparation.

SNAFL-1 was purchased as the free carboxylic acid from Molecular Probes in a 1 mg vial. 0.3 mL of isopropyl alcohol and 0.7 mL of water was added to make a 1 mg/mL solution. A molecular weight (MW) of 426 for SNAFL-1 was used to calculate molarity (SNAFL-1=2.35 mM). 4.25 uL of this solution was diluted to 1 mL with various 50 mM phosphate buffers to give 10 micromolar solutions with pH 6-10. 10 micromolar solutions of SNAFL-2 (MW=460) were prepared in a similar fashion. EBIO-1 (MW=523), EBIO-2 (MW=627), and EBIO-3 (MW=489) were obtained as bulk compounds from Epoch Biosciences. 1.6 mg of each solid powder was carefully weighed out and dissolved in 3.2 mL of 40% isopropyl alcohol to give 0.5 mg/mL solutions. Emission spectra were obtained for the various SNAFL and EBIO compounds at pH 6.0, 6.2, 6.4, 6.6, 6.8, 7.0, 8.0 and 10.0. Examples of overlayed fluorescence emission spectra are shown in FIG. 26 (SNAFL-1) and FIG. 27 (EBIO-3). All spectra showed an isosbestic wavelength where all emission spectra overlap (See Table 1). This is a characteristic of ideal ratiometric performance with no competing fluorescent structures other than those shown above (lactone, naphthol, naphtholate).

pKa Calculations.

The pH at which two molecular species (tautomers) are equally represented is defined as the pKa. There are many variables that can affect pKa and methods for measurement are difficult since the structures have overlapping absorbance. Therefore direct comparisons from the literature can vary slightly. The calculations contained herein are based on the assumption that, at pH 10, only the trianionic naphtholate structure is present. The intensity of fluorescence at the emission maxima is divided by 2, and pH of the intersecting pH curve is calculated by interpolation between the nearest 2 curves. The pKa of the 2-chloro substituted EBIO compounds is significantly lower than the other analogs as shown in Table 1.

Example 9

The Preparation of Representative Fluorophore-Protein Conjugates

SNAFL-1/HSA

Human serum albumin (HSA) was purchased from Sigma (catalog #A-8763) as 100 mg of lyophilized powder. SNAFL-1 NHS ester was purchased from Molecular Probes as a mixture of the 5 and 6 isomers. A solution of 10 mg (0.15 micromoles) of HSA in 1 mL of pH 8.56 sodium bicarbonate (0.1 M) was prepared. A solution of 1 mL (1.91 micromoles) of the NHS ester in 0.1 mL of dimethylsulfoxide was prepared. 0.3 mL aliquots of the HSA solution were transferred to a 1.6 mL Eppendorf tubes and various offering ratios of the NHS ester solution were added: tube 1, 11.8 microliters (5 equivalents); tube 2, 23.6 microliters (10 equivalents), tube 3, 47.1 microliters (20 equivalents). The deep red solutions were vortexed and allowed to stand in the dark for at least one hour. The 5:1 conjugate from tube 1 was purified by gel filtration chromatography on a 0.5×20 cm column packed with Sephadex G-15 and pH 7.4 phosphate buffered saline (PBS). The conjugate was isolated as a fast moving red/orange band in PBS and diluted to 0.75 mL with PBS to give a 4 mg/mL solution of the protein conjugate. Most of the color eluted with the conjugate, but some small molecular weight (orange) impurities remained on top of the column. The column was clean enough to be re-used for purification of the 10:1 and 20:1 conjugates. Each was eluted in PBS and diluted to 0.75 mL to give ~4 mg/mL solutions (60 micromolar based on HSA component). The red solutions were stored refrigerated and protected from light. 1 micromolar solutions of each SNAFL-1/HSA conjugate were prepared and analyzed by UV-vis spectra using a Beckman DU640B spectrometer. Each spectrum showed absorbance maxima at 490 and 521 nm at pH 7 as expected for the acid form of SNAFL-1 conjugates. The relative absorbance showed the expected change in absorbance with different SNAFL:HSA offering ratio. A 10 micromolar solution of SNAFL-1 acid (obtained from Molecular Probes) at pH 7 was used as a standard to more accurately determine the average loading of SNAFL-1 per each HSA conjugate preparation. Using this assay, the 5:1 conjugate had 4.1 fluors/HSA, the 10:1 conjugate had 6.4 fluors/HSA, and the 20:1 conjugate had 11.2 fluors/HSA.

Example 10

The Fluorescent Properties of Representative Fluorophore-Protein Conjugates

SNAFL-1/HSA

Relative fluorescence of various SNAFL-1/HSA conjugates and SNAFL-1 free acid were compared using an Ocean Optics USB2000 fiber optic spectrometer and a tungsten halogen light source (part number HL-2000 FHSA). The light source was equipped with a linear variable filter that allowed the wavelength and shape of the excitation beam to be adjusted. A cuvette holder (part number CUV-FL-DA) was directly attached to the light source and a fiber optic cable directed emitted light to the spectrometer. Excitation conditions are reported for each fluorescence spectrum (3000 msec irradiation at the indicated wavelength). Spectral data were collected on a personal computer using the Ocean Optics software and overlays of different spectra were captured. A comparison of various loading levels of SNAFL-1/HSA showed that 4.1 to 1.6 SNAFL-1 molecules gave about the same fluorescent signal. Higher loading or lower loading conjugates gave lower signals.

Emission spectra were obtained for 10 micromolar solutions in potassium phosphate buffer. Excitation was at 540 nm. Emission maximum at 620 nm was observed for the base form of SNAFL-1 (pH 10). As expected, intensity of 620 nm fluorescence decreased as pH decreased. An isosbestic point at 585 nm, where fluorescence remained constant at all pH, was observed. Response was good at about pH 8, but poor between pH 6-7.

Spectra obtained for a 2.5 micromolar solution of a representative SNAFL-1/HSA conjugate (1.6 SNAFL-1/HSA) showed improved pH response for pH 6-7 (see FIG. 29). The Ocean Optics halogen light source was equipped with a 532 nm interference filter (Edmund Optics, Barrington, N.J.) and this allowed the fluorescent isosbestic point at 572 nm for pH 6-7 to be detected. Emission maximum at 620 nm was observed for the base form of SNAFL-1 (see pH 10 curve). As expected, intensity of 620 nm fluorescence decreased as pH decreased. In comparison to the free SNAFL-1 carboxylic acid (see FIG. 26) improved response for pH 6-7 was observed for the HSA conjugate. A red shift of the pH 8 and 10 curves from the isosbestic wavelength was observed, indicative of other competing molecular structures involving the fluorescent species. This non-ideal behavior may be eliminated by use of a longer linker structure or a more hydrophilic linker structure between the fluorescent dye and the HSA spacer.

Example 11

The Fluorescent Properties of Representative Fluorophore-Protein Conjugates

EBIO-3/HSA

Fluorescence spectra were obtained for 2.5 micromolar solutions of the two EBIO-3/HSA conjugates prepared as described in Example 1 (Method A). The conjugates showed improved pH response for pH 6-7 (see FIG. 12 for overlayed spectra for the 1.92:1 EBIO-3/HSA conjugate). The Ocean Optics halogen light source was equipped with a 532 nm bandpass filter (Edmund Optics, Barrington N.J.) and this allowed the fluorescent isosbestic point at ~565 nm for pH 6-7 to be detected. Emission maximum at 605 nm was observed for the base form of SNAFL-1 (red trace, pH 10). As expected, intensity of 605 nm fluorescence decreased as pH decreased. In comparison to the SNAFL-1/HSA conjugate (see FIG. 29) improved response for pH 6-7 was observed for the EBIO-3/HSA conjugate. A red shift of the pH 8 and 10 curves from the isosbestic wavelength was observed, indicative of other competing molecular structures involving the fluorescent species, but was of smaller magnitude than for the SNAFL-1/HSA conjugate.

Example 12

Immobilization of Representative Fluorophore-Protein Conjugates

SNAFL-1/HSA

Fluorophore-protein conjugates and fluorophore-carbohydrate conjugates were immobilized on either nitrocellulose or capillary pore membranes using the following general method. Fluorescein labeled dextrans with "fixable" lysine residues were obtained from Molecular Probes. These dextrans had a molecular weight of about 10,000 1.8 fluorophores per conjugate, and 2.2 lysines per conjugate and are sold under the trade name "Fluoro-Emerald." Fluorescein labeled bovine serum albumin (BSA) was also obtained from Molecular Probes and had 4.5 fluors per conjugate. Various SNAFL-1/HSA conjugates were prepared as described in Example 13. Nitrocellulose membranes were obtained from Schleicher and Schuell under the trade name PROTRAN. Pore diameter was reported as 0.2 microns. Capillary pore membranes made from polyester films were obtained from Oxyphen in a variety of pore sizes. 0.1 micron and 1.0 micron pore size membranes were successfully used to immobilize fluorescein dextrans. Fluorescein/dextran, fluorescein/BSA and SNAFL-1/HSA conjugates were all successfully immobilized and the fluorescent properties of the SNAFL-1/HSA conjugates were fully characterized as described as follows.

General Immobilization Method.

SNAFL-1/HSA (2.5 SNAFL-1/HSA) on 0.1 micron pore diameter Oxyphen Membrane Discs. Fluorescent HSA conjugates with a 2.5:1 SNAFL-1:HSA offering ratio were prepared as described in Example 4 and diluted to provide concentrations of 0.05, 0.2, 1.0 and 4 mg/mL in phosphate buffered saline (PBS) (pH 7.4). 5 microliter drops were applied via a 20 microliter pipettor to the center of pre-punched porous discs (¼ inch diameter) that were laid on a bench top. The spotted discs were allowed to air dry (about 30 minutes) and then placed in separate desiccators overnight. The dried discs were washed in separate Eppendorf tubes with 2×1 mL of PBS and allowed to soak overnight in 1 mL of PBS. The washed discs were stable in PBS solution (no degradation after 30 days). Alternatively the discs could be re-dried in desiccators and stored dry. The wet or dry stored discs had comparable fluorescent properties. The discs had fluorescent signals that were proportional to the concentration of labeled macromolecule applied to each one as measured by the fluorescence assay described in Example 9.

Example 13

The Fluorescent Properties of Representative Immobilized Fluorophore-Protein Conjugates

SNAFL-1/HSA

Microwell Assay of Fluorescent Macromolecular Conjugates on Porous Membrane Discs Using a Fiber Optic Spectrometer.

Fluorescent discs prepared as described in Example 8 were examined for fluorescent properties using the Ocean Optics fiber optic spectrometer described in Example 14. The cuvette on the light source was replaced by a fiber optic reflectance probe which had 6 excitation fibers wrapped around a single fiber that picks up the emitted light from the sample and sends it to the spectrometer. The reflectance probe was threaded through a hole in a 12×12×18 inch black box with a lid on the front. The probe was clamped inside under a 1 cm square opening that allowed the tip of the probe to be positioned under a 96-well micro well plate (clear bottom black plate). The probe was tilted at a 30 degree angle to reduce reflected light entering the probe tip. The fluorescent disc of interest was placed in the bottom of a well and covered with 300 microliters of the analyte solution of interest. The excitation light source was turned on long enough to position the disc of interest over the tip of the reflectance probe, then the shutter was closed and the plate was covered with another box to shield the disc from ambient light. Unless otherwise mentioned, the Ocean Optics software was set to collect data with a 3000 msec integration time and 3 averages. A dark spectrum was captured with the shutter closed and used for all background subtracted readings during the assay. The shutter was then opened and fluorescent reading of the disc was started. The graphical display on the computer screen gave real-time spectra after each 3000 msec integration time. After the required 3 spectra were obtained (about 10 seconds) the graphical display showed only subtle changes. At this point a snapshot of the displayed spectrum was captured and saved to disc for future processing. The shutter was closed, and the next microwell experiment was set up. The same disc could be measured multiple times by exchanging the analyte solution in the microwells. Alternatively, different discs in different wells could be measured by re-positioning the microwell plate over the reflectance probe.

Fluorescent Loading of SNAFL-1/HSA Immobilized on Oxyphen Discs.

The microwell assay described above was used to compare the relative-fluorescence of SNAFL-1/HSA on Oxyphen discs. The excitation filters in the halogen light source were set to a wavelength of 532 nm and a "wide open" bandpass position to maximize sensitivity of the assay. Reflectance of the excitation beam back into the detector fiber was significant, and the wavelength position of the filter was adjusted to provide a "minimum" at 620 nm where the fluorescence from the base form of SNAFL-1/HSA is greatest. The various concentrations of SNAFL-1/HSA described in Example 16 were examined in separate microwells in pH 7 potassium phosphate buffer (50 mM) as described above. The spectra showed the ability to distinguish relative fluorescence intensity of 4, 1, 0.2 and 0.05 mg/mL membranes at pH 7. All had signal greater than background.

Relative Fluorescence Intensity of Various Amounts of SNAFL-1/HSA (2.5:1) Immobilized on Porous Oxyphen Discs at pH 7.

The fluorescent intensity was measured at 620 nm, the fluorescent maximum of the base form of the fluorophore. Excitation used a wide open setting on the halogen lamp that efficiently excites both acid and base forms of SNAFL-1. The reflected light from the source (unmodified disc) had the lowest intensity spectrum. The spectrum of the 0.05 mg/mL disc gave a small increase in fluorescence intensity. The 0.2 mg/mL disc, 1 mg/mL disc, and 4 mg/mL disc showed stepwise increases in fluorescence intensity. The fluorescence spectra of two 30 day PBS soaked sample (1 mg/mL) from a different batch of membranes were essentially the same and showed that membrane loading was reproducible from batch to batch, and that the SNAFL-1/HSA conjugates did not dissociate significantly from the disc surface in PBS solution.

pH Dependent Fluorescence of SNAFL-1/HSA Immobilized on Oxyphen Discs.

The 1 mg/mL SNAFL-1/HSA discs described above were examined for pH dependent response in the microwell assay. A single disc was examined in potassium phosphate buffers of pH 4, 5, 6, 7, 8, 9, and 10. The data showed that these membrane discs had a wide dynamic range of pH measurement, but had more sensitive response at pH>6. The time between buffer exchanges was 5 min, and there was no significant change in spectra after additional equilibration time. This showed that the response time for even dramatic changes in the pH environment of the immobilized SNAFL-1/HSA conjugates is rapid.

"Crossover Assay" for Fluorescence Measurement of pH Using SNAFL-1/HSA Oxyphen Discs.

The microwell assay described above was used to examine the fluorescent isosbestic properties of the discs. For this assay, the shutter assembly in Ocean Optics halogen light source (part number HL-2000 FHSA) was removed, and two 532 nm bandpass filters (Edmund Scientific) were inserted in the cavity using a special adaptor. This dramatically reduced the reflected background in the spectral region of interest (>550 nm). The data shown are for 4 mg/mL loading discs prepared with SNAFL:HSA (5:1) conjugate. The immobilized protein conjugate showed unusual pH vs. fluorescence properties in comparison to the solution phase data. Instead of a fluorescent isosbestic point at 575 nm, there was a stepwise increase in the fluorescent intensity as pH increased. The pH 10 spectrum showed the expected maximum at 620 nm, and crossed the overlaid spectral curves obtained in pH 4, 6, 7 and 8 buffers. These "crossover points" were used as the basis for a sensitive assay to determine pH of the membrane environment. Three different membrane discs were examined using this assay format on three different days. The crossover points were reproducible within 2 nm.

The 4 mg/mL discs (3.6:1 SNAFL-1:HSA) showed stepwise increase in pH 10 "crossover." The crossover was at 579 nm for pH 4. Three discs/three different days gave the same result ±2 nm. The crossover points were at 592 nm (pH 6), 600 nm (pH 7a,b), and 611 nm (pH 8). The fluorescent maximum at pH 10 was at 620 nm, similar to the solution phase properties.

Example 14

The Fluorescent Properties of Representative Immobilized Fluorophore-Protein Conjugates

EBIO-3/HSA

Telescoping Tubing Insert Assay of Fluorescent Macromolecular Conjugates on Porous Membrane Discs Using a Fiber Optic Spectrometer.

Fluorescent discs prepared as described in Example 2 were examined to relate the fluorescent properties to the liquid phase pH using the Ocean Optics fiber optic spectrometer described in Example 17 with the dual 532 nm filtered (Edmund Scientific) halogen light source (part number HL-2000 FHSA). A holder for a 5/32 inch membrane disc was crafted with 4 mm OD and 5 mm OD polystyrene telescoping tubing and an angled 0.015 in thick polystyrene window. The angled window was placed so that it held the membrane disc at a 60 degree angle relative to the tubing axis. This allows the fiber optic probe to be placed in one end of the tubing and interrogate the disc on the other side of the window which is contact with a liquid of a certain pH. Buffers of known pH values were placed in contact with the telescoping tubing inserts and discs made by the spotting immobilization method in Example 2 and fluorescent emissions recorded with the Ocean Optics software set to collect data with a 1000 msec integration time and 3 averages.

For liquids with unknown pH values, a stirred and light protected vessel containing 5 telescoping tubing inserts and discs made by the soaking immobilization method in Example 2, 50 mL of buffer or plasma, and a calibrated pH electrode (ROSS electrode/Orion 720a meter) was used to study the pH and fluorescent response of the fluorescent discs. Drops of 1 N HCl or 1 M NaOH were added to create a range of pHs from liquids studied. Fluorescent spectra were collected through Ocean Optics macros in Excel set to read for 1000 msec integration time and three averages. The spectra were analyzed using the modeled bandpass filters and ratiometric method in Excel to obtain calibration curves for PBS, platelet poor plasma and platelet rich plasma.

Injection Molded Insert Pvc Tube Assay of Fluorescent Macromolecular Conjugates on Porous Membrane Discs Using a Custom Optimized Fluorescence Based pH Detector.

Injection molded polycarbonate parts were fashioned to fix the fluorescent discs to the fluorescence pH detector probe as pictured in FIG. 22. Membranes were prepared as described in the soaking immobilization method in Example 2 and assembled into the plastic insert. A 1 in long and 3/16 in ID PVC tube was placed on the spike end of the insert such that 250 ul of liquid was placed in the tube and covered with parafilm to slow carbon dioxide desorption. A fluorescent measurement of the first and second wavelengths was taken and then the pH was read by a blood gas analyzer (Bayer 348). The pH of plasma samples were adjusted by acid and base additions as in the telescoping tubing insert assay to create the range of pH data.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for monitoring a parameter of a sample, comprising:
   (a) irradiating a fluorescent seminaphthofluorescein species having a first emission intensity at a first emission wavelength and a second emission intensity at a second emission wavelength, each emission intensity dependent upon a parameter, which excitation light emanating from a probe physically isolated from the fluorescent species to provide first and second emission intensities, wherein the fluorescent species is in liquid communication with a sample contained in a vessel;
   (b) measuring the first and second emission intensities to determine a first parameter reading of the sample; and
   (c) repeating step (a) after a pre-determined time and measuring the first and second emission intensities to determine a second parameter reading of the sample.

2. The method of claim 1, wherein step (c) is repeated to provide multiple parameter readings to monitor the parameter of the sample over time.

3. The method of claim 1, wherein the parameter is pH.

4. The method of claim 1, wherein the parameter is $CO_2$.

5. The method of claim 1 further comprising electronically writing parameter readings to the vessel containing the sample.

6. A method for monitoring the pH of a sample, comprising:
   (a) irradiating a fluorescent seminaphthofluorescein species in liquid communication with a sample contained in a vessel with excitation light emanating from a probe physically isolated from the fluorescent species, wherein the excitation light has a wavelength sufficient to effect fluorescent emission from the fluorescent species, wherein the fluorescent species exhibits a first emission intensity at a first emission wavelength and a second emission intensity at a second wavelength, the ratio of the first and second emission intensities being dependent upon pH, wherein the first and second emission wavelengths are not the same;
   (b) measuring the first and second emission intensities to determine a first parameter reading of the sample; and
   (c) repeating step (a) after a pre-determined time and measuring the first and second emission intensities to determine a second parameter reading of the sample.

7. The method of claim 6, wherein step (c) is repeated to provide multiple pH readings to monitor the pH of the sample over time.

8. The method of claim 6 further comprising electronically writing pH readings to the vessel containing the sample.

9. The method of claim 1, wherein the pre-determined time is from about 1 minute to about 1 day.

10. The method of claim 1, wherein the pre-determined time is from about 1 hour to about 12 hours.

11. The method of claim 2, further comprising obtaining a sample profile from the multiple readings.

12. The method of claim 11, further comprising determining sample quality from the profile.

13. The method of claim 6, wherein the probe is physically isolated from the fluorescent species by a window transparent to the excitation light and the fluorescent emission.

14. The method of claim 1, wherein the fluorescent species is a seminaphthofluorescein compound selected from the group consisting of 5'(and 6')-carboxy-3,10-dihydroxy-spiro[7H-benzo[c]xanthene-7,1'(3'H)-isobenzofuran]-3'-one and 2-(2-chloro-3-hydroxy-9-carboxyethyl-10-oxo-10H-benzo[c]xanthen-7-yl)benzoic acid.

15. The method of claim 1, wherein the fluorescent species is a conjugate of a fluorescent species and a macromolecule.

16. The method of claim 15, wherein the macromolecule is an albumin.

17. The method of claim 1, wherein the fluorescent species is a seminaphthofluorescein/human serum albumin conjugate.

18. The method of claim 1, wherein the sample comprises blood or a blood product.

19. The method of claim 1, wherein the vessel is a sealed vessel.

* * * * *